(12) United States Patent
Singh et al.

(10) Patent No.: US 9,535,052 B2
(45) Date of Patent: Jan. 3, 2017

(54) APPARATUS AND METHOD FOR ISOLATING LEUKOCYTES AND TUMOR CELLS BY FILTRATION

(71) Applicant: NESTEC S.A., Vevey (CH)

(72) Inventors: Sharat Singh, Rancho Santa Fe, CA (US); Xinjun Liu, San Diego, CA (US); Kelly D. Hester, San Diego, CA (US)

(73) Assignee: NESTEC S.A., Vevey (CH)

( * ) Notice: Subject to any disclaimer, the term of this patent is extended or adjusted under 35 U.S.C. 154(b) by 110 days.

(21) Appl. No.: 13/961,847

(22) Filed: Aug. 7, 2013

(65) Prior Publication Data

US 2013/0323711 A1 Dec. 5, 2013

Related U.S. Application Data

(63) Continuation of application No. PCT/US2012/025491, filed on Feb. 16, 2012.
(Continued)

(51) Int. Cl.
| | |
|---|---|
| *G01N 33/49* | (2006.01) |
| *G01N 1/40* | (2006.01) |
| *A61M 1/02* | (2006.01) |
| *A61M 1/34* | (2006.01) |
| *B01L 3/00* | (2006.01) |
| *A61M 1/36* | (2006.01) |

(52) U.S. Cl.
CPC ............ *G01N 33/491* (2013.01); *A61M 1/029* (2013.01); *A61M 1/3496* (2013.01); *B01L 3/5021* (2013.01); *G01N 1/4077* (2013.01); *A61M 1/02* (2013.01); *A61M 1/3633* (2013.01); *A61M 2202/0439* (2013.01); *B01L 2300/046* (2013.01); *B01L 2300/0681* (2013.01); *G01N 2001/4088* (2013.01)

(58) Field of Classification Search
CPC ................ G01N 33/491; G01N 1/4077; G01N 2001/4088; A61M 1/02; A61M 1/029; A61M 1/3496; A61M 1/3633; A61M 2202/0439; B01L 3/5021; B01L 2300/0681; B01L 2300/046
See application file for complete search history.

(56) References Cited

U.S. PATENT DOCUMENTS

| | | | |
|---|---|---|---|
| 4,915,848 A | | 4/1990 | Carmen et al. |
| 5,556,544 A | * | 9/1996 | Didier .......................... 210/436 |

(Continued)

FOREIGN PATENT DOCUMENTS

| | | |
|---|---|---|
| DE | 2125027 | 12/1971 |
| EP | 0 616 816 A2 | 9/1994 |

(Continued)

*Primary Examiner* — John Kim
(74) *Attorney, Agent, or Firm* — Kilpatrick Townsend & Stockton LLP

(57) ABSTRACT

The present invention provides novel apparatuses and methods for isolating or recovering a subset of blood cells such as leukocytes and/or circulating tumor cells from blood samples by filtration without changing the intracellular concentration of a therapeutic agent such as an anticancer drug. Contrary to the art, the apparatuses and methods of the present invention advantageously provide cell lysates from recovered cells such as leukocytes and/or circulating tumor cells without substantial dilution of a therapeutic agent such as an anticancer drug.

27 Claims, 41 Drawing Sheets

Related U.S. Application Data

(60) Provisional application No. 61/444,044, filed on Feb. 17, 2011, provisional application No. 61/489,998, filed on May 25, 2011.

(56) References Cited

U.S. PATENT DOCUMENTS

| | | | |
|---|---|---|---|
| 6,622,882 B2 * | 9/2003 | Smith | ........................ 220/259.1 |
| 2010/0012589 A1 | 1/2010 | Ribault et al. | |

FOREIGN PATENT DOCUMENTS

| | | |
|---|---|---|
| EP | 1 424 131 A2 | 6/2004 |
| EP | 2 260 943 A1 | 12/2010 |
| JP | 56-28663 A | 3/1981 |
| JP | 2005-525114 A | 8/2005 |
| JP | 2005-283356 A | 10/2005 |
| JP | 2008-503206 A | 2/2008 |
| JP | 2008-526255 A | 7/2008 |
| WO | 02/24256 A1 | 3/2002 |
| WO | 03/091407 A2 | 11/2003 |
| WO | 2005/115115 A2 | 12/2005 |

* cited by examiner

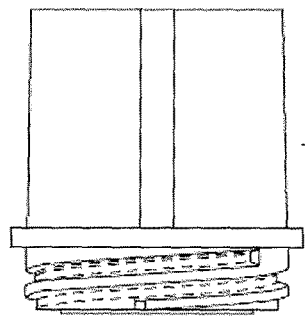
FIG. 2A
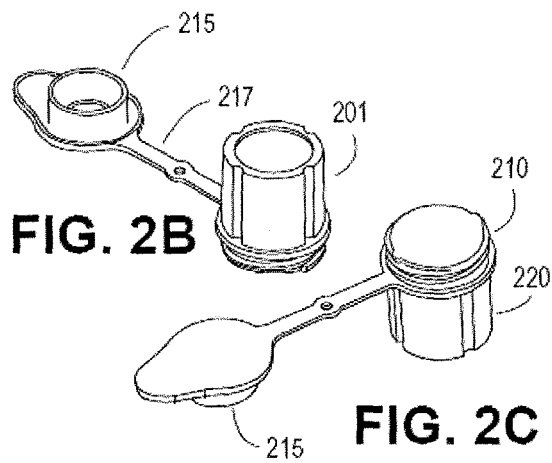
FIG. 2B
FIG. 2C
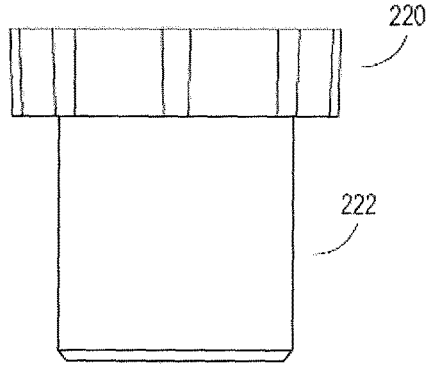
FIG. 2D
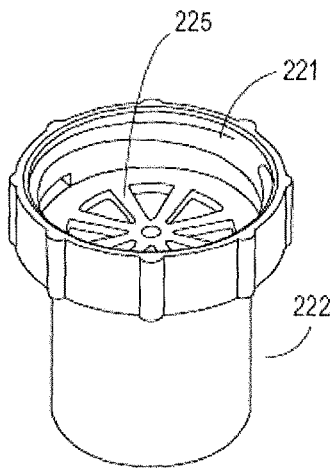
FIG. 2E
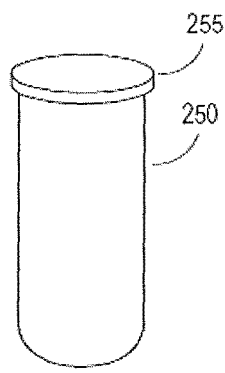
FIG. 2F
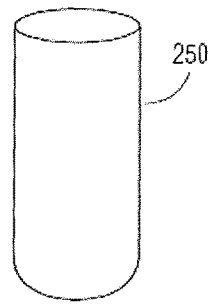
FIG. 2G

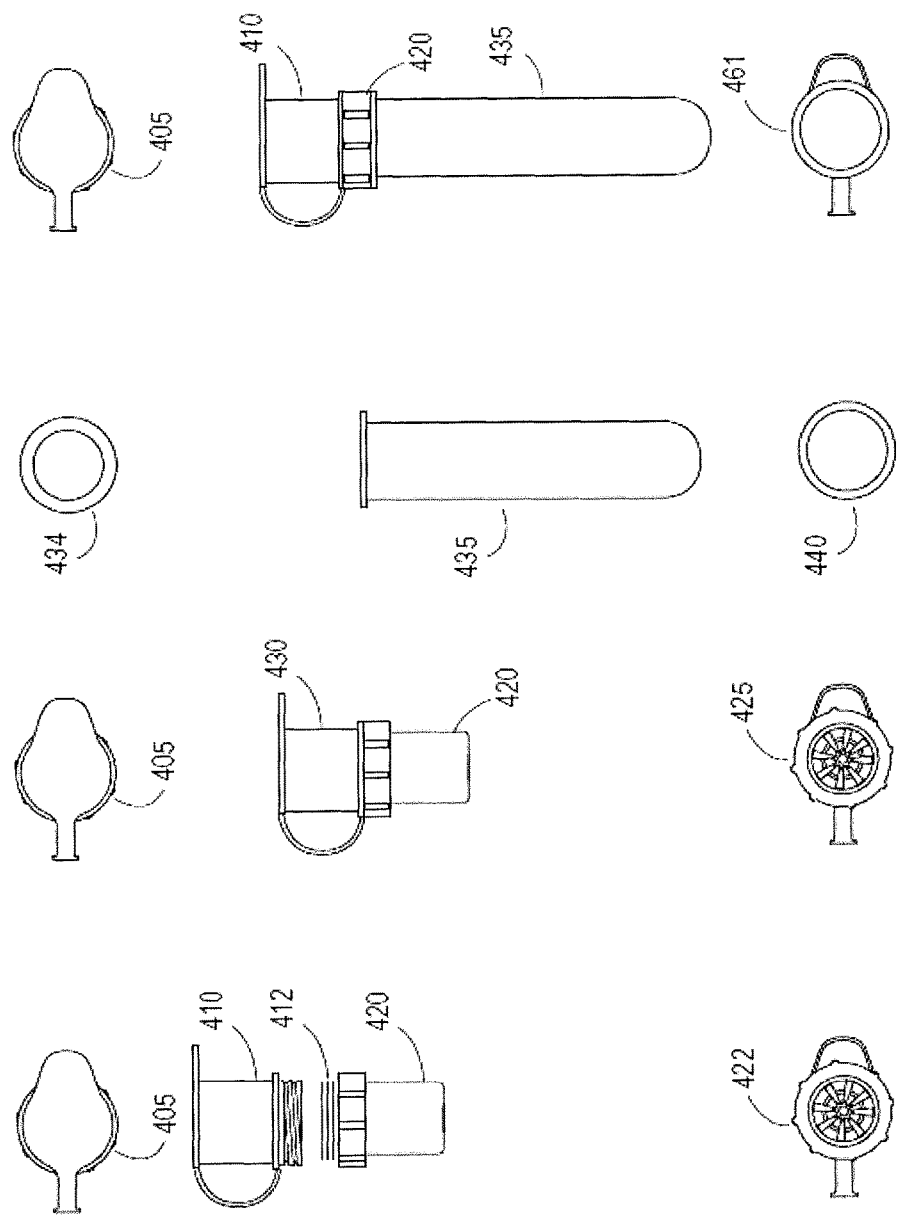

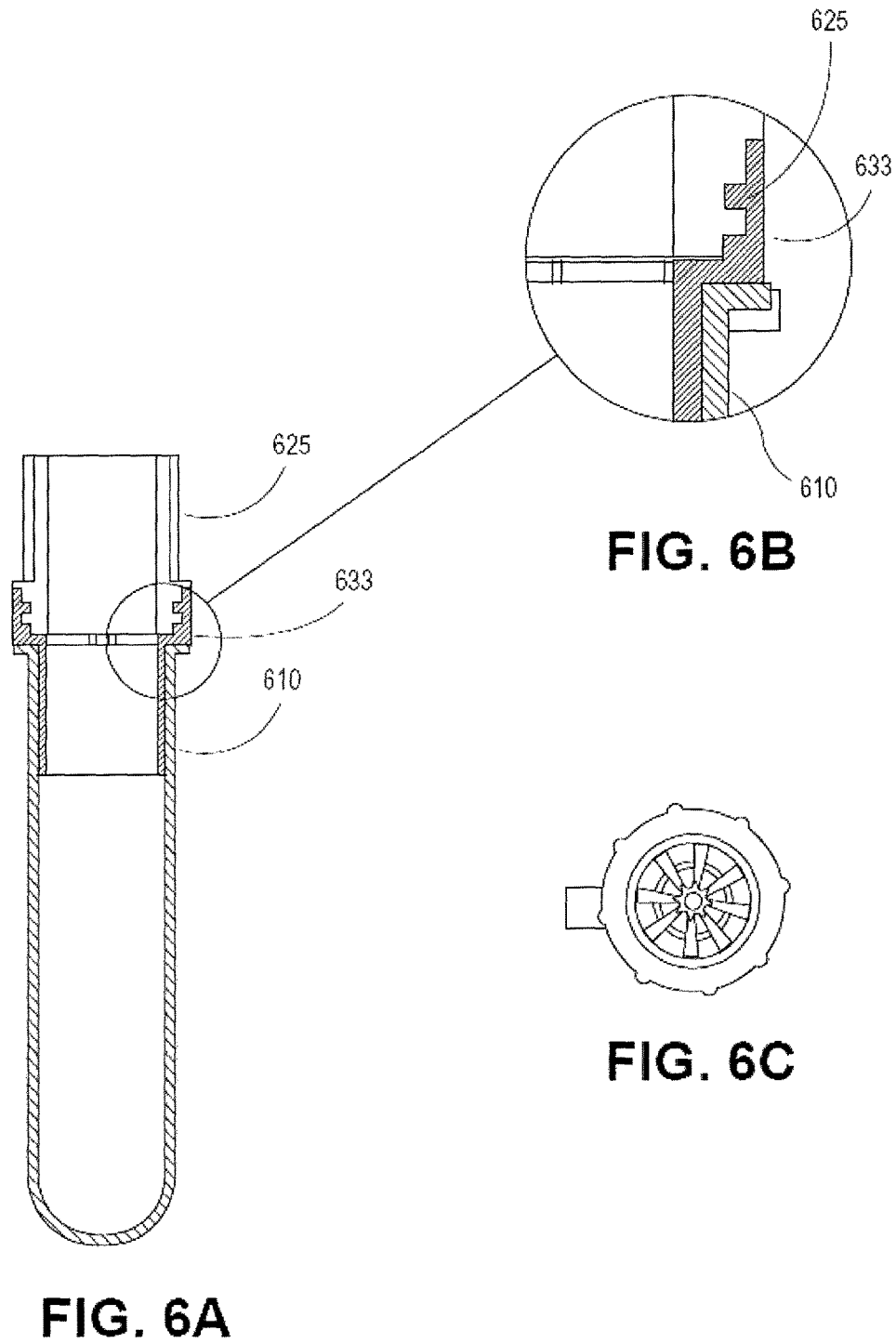

1,000,000 K562 cells spiked in 1ml of blood from normal donor

| Patient ID | 1 | 2 | | |
|---|---|---|---|---|
| Gender | Female | Male | Male | Male |
| Race | White | White | White | White |
| Smoking history | Current cigarette | Current cigarette | Current cigarette | Previous use |
| Alcohol history | No history | No history | No history | Current use |
| Primary diagnosis | CML | CML | CML | CML |
| Treatment status | Active | Active | Active | Active |
| Treatment | imatinib | imatinib | dasatinib | imatinib |
| Date of collection | 1/31 | 2/2 | 2/7 | 2/15 |
| WBC: Total cell count | 5,600,000 | 15,000,000 | 4,000,000 | ----- |
| WBC: Phospho BCR-ABL | 11,000 | 156,000 | ----- | ----- |
| Phospho signal with imatinib ratio | 0.0019 | 0.0124 | ----- | ----- |
| Assuming 90% inhibition | 0.019 | 0.124 | ----- | ----- |

*FIG. 10*

Without subtracted blood background

Phospho BCR-ABL Profile of Patient 1

| Sample | Average | CV% | Ratio |
|---|---|---|---|
| Standard 10,000 | 62316 | 0.18 | 77.77 |
| 1000 | 60249 | 1.16 | 75.19 |
| 100 | 6291.33333 | 0.81 | 7.85 |
| 10 | 1519.33333 | 6.65 | 1.90 |
| 0 | 801.333333 | 5.79 | 1.00 |
| 30 | 2157.66667 | 12.69 | 2.69 |
| 300 | 14526.3333 | 12.84 | 18.13 |
| 3000 | 62260.6667 | 0.07 | 77.70 |

| Sample | Average | CV% | Ratio |
|---|---|---|---|
| S1 1:20 | 2258.7 | 10.9 | 2.8 |
| S2 1:20 | 1146.3 | 7.9 | 1.4 |
| S3 1:20 | 1302.0 | 10.2 | 1.6 |
| S5 1:20 | 1602.3 | 3.7 | 2.0 |
| S4 1:20 | 1587.3 | 4.0 | 2.0 |
| S6 1:20 | 1538.7 | 2.2 | 1.9 |
| S8 1:20 | 1509.3 | 7.1 | 1.9 |
| S9 1:20 | 1885.0 | 3.4 | 2.4 |

| Sample | Average | CV% | Ratio |
|---|---|---|---|
| S1 1:5 | 6381.7 | 0.7 | 8.0 |
| S2 1:5 | 3411.3 | 15.5 | 4.3 |
| S3 1:5 | 3457.3 | 4.7 | 4.3 |
| S5 1:5 | 3622.0 | 14.1 | 4.5 |
| S4 1:5 | 5272.7 | 11.5 | 6.6 |
| S6 1:5 | 5877.3 | 8.3 | 7.3 |
| S8 1:5 | 4245.3 | 14.7 | 5.3 |
| S9 1:5 | 5130.3 | 11.2 | 6.4 |

*FIG. 12B*

After subtracted blood background

Phospho CRKL

Phospho AKT

Phospho STAT5

Phospho SRC

Phospho CRKL

Phospho AKT

Phospho STAT5

Phospho SRC

| Patient | Blood draws | Treatment | Notes |
|---|---|---|---|
| 1 | 3 | Gleevec | |
| 2 | 6 | Gleevec | Recent Diagnosis |
| 3 | 7 | Sprycel | |
| 4 | 4 | Gleevec | |
| 5 | 5 | Gleevec | |
| 6 | 12 | Gleevec | |
| 7 | 6 | Gleevec | |
| 8 | 5 | Possible Progression | Switched to Sprycel |
| 9 | 1 | Gleevec | |
| 10 | 3 | Gleevec | |
| 11 | 3 | Gleevec | |
| 12 | 3 | Gleevec | |
| 13 | 1 | Gleevec | |
| 14 | 9 | Sprycel | New Diagnosis |
| 15 | 1 | Gleevec | |
| 16 | 1 | Post-treatment | |
| 17 | 4 | Sprycel | |
| 18 | 5 | Posatinib | |
| 19 | 3 | Tasigna | New Diagnosis |
| 20 | 6 | Sprycel | New Diagnosis |
| 21 | 2 | Hydroxyurea | |
| 22 | 1 | Gleevec | |
| 23 | 2 | Gleevec | Recent Diagnosis |
| 24 | 1 | Gleevec | Recent Diagnosis |
| 25 | 3 | Tasigna | Recent Diagnosis |
| 26 | 1 | Gleevec | Recent Diagnosis |
| 27 | 1 | Gleevec | New Diagnosis |

*FIG. 24*

| Patient | Sample | Draw | Cell count | mRNA ratio | pBcr-Abl | p/WBC (%) | tBcr-Abl | t/WBC (%) | p/t | Notes |
|---|---|---|---|---|---|---|---|---|---|---|
| 2 | 2 | 2/2 | 1.49E+07 | 47.53% | 128,592 | 0.866 | not determined | 0.701 | 1.17 | Gleevec |
| | 5 | 3/2 | 6.00E+06 | 17.92% | 49,101 | 0.820 | 42,062 | 0.440 | 0.09 | |
| | 16 | 5/11 | 3.45E+06 | 0.00% | 1,517 | 0.044 | 15,177 | 0.180 | 0.33 | |
| | 20 | 6/1 | 5.55E+06 | 5.46% | 3,340 | 0.060 | 10,217 | 0.242 | 1.05 | |
| | 60 * | 10/12 | 6.75E+06 | 4.84% | 17,084 | 0.253 | 16,316 | 0.209 | 1.19 | |
| | 89 * | 12/21 | 5.50E+06 | 2.21% | 13,666 | 0.248 | 11,508 | | | |
| 3 | 3 | 2/7 | 4.00E+06 | 0.00% | 6,057 | 0.151 | 2,547 | 0.063 | 2.38 | Sprycel |
| | 9 | 4/4 | 8.50E+06 | 0.00% | 7,823 | 0.092 | 1,836 | 0.022 | 4.26 | |
| | 35 * | 7/25 | 7.65E+06 | 0.00% | 2,657 | 0.035 | 2,777 | 0.036 | 0.96 | |
| | 45 * | 8/22 | 4.90E+06 | 0.01% | 8,615 | 0.176 | 9,370 | 0.191 | 0.92 | |
| 4 | 4 | 2/15 | 6.30E+06 | 1.72% | 6,142 | 0.097 | 2,454 | 0.039 | 2.50 | Gleevec |
| | 7 | 3/22 | 4.40E+06 | 0.57% | 2,008 | 0.046 | 3,132 | 0.071 | 0.64 | |
| | 27 | 6/28 | 3.55E+06 | 0.19% | 7,011 | 0.197 | 5,770 | 0.1625 | 1.22 | |
| | 55 * | 9/27 | 3.00E+06 | 0.13% | 9,065 | 0.302 | 2,554 | 0.085 | 3.55 | |
| 8 | 18 | 5/18 | 6.90E+06 | 4.53% | 5,353 | 0.077 | 45,644 | 0.662 | 0.12 | Possible Progression |
| | 25 | 6/20 | 7.10E+06 | 1.32% | 4,360 | 0.061 | 33,809 | 0.476 | 0.13 | Sprycel |
| | 31 * | 7/18 | 3.40E+06 | 0.35% | 2,263 | 0.067 | 14,369 | 0.423 | 0.16 | |
| | 44 * | 8/18 | 5.50E+06 | 0.04% | 2,421 | 0.044 | 2,996 | 0.054 | 0.81 | |
| | 61 * | 10/13 | 7.50E+06 | 0.01% | 1,887 | 0.025 | 4,825 | 0.640 | 0.39 | |
| 14 | 28 | 6/28 | 1.36E+07 | 51.18% | 83,761 | 0.616 | 115,074 | 0.846 | 0.73 | Hydroxyurea |
| | 48 * | 8/29 | 5.25E+06 | 1.17% | 8,257 | 0.157 | 32,735 | 0.624 | 0.25 | Sprycel |
| | 57 | 10/3 | 6.75E+06 | 0.08% | 5,616 | 0.083 | 3,585 | 0.053 | 1.56 | |
| 18 | 38 * | 7/28 | 1.53E+07 | 36.19% | 123,992 | 0.810 | 447,903 | 2.930 | 0.28 | Tasigna |
| | 41 * | 8/11 | 1.65E+07 | 51.30% | 104,505 | 0.630 | 286,432 | 1.740 | 0.36 | |
| | 50 * | 9/7 | 2.60E+07 | 52.35% | 95,679 | 0.370 | 705,569 | 2.710 | 0.14 | |
| | 71 * | 11/9 | 5.25E+06 | 1.03% | 12,157 | 0.232 | 24,805 | 0.472 | 0.49 | Ponatinib |

FIG. 25

APPARATUS AND METHOD FOR ISOLATING LEUKOCYTES AND TUMOR CELLS BY FILTRATION

CROSS-REFERENCE TO RELATED APPLICATIONS

The present application is a continuation of PCT/US2012/025491, filed Feb. 16, 2012, which application claims priority to U.S. Provisional Patent Application Nos. 61/444,044, filed Feb. 17, 2011 and 61/489,998, filed May 25, 2011, the disclosures of which are herein incorporated by reference in their entireties for all purposes.

BACKGROUND OF THE INVENTION

Cancer is the second leading cause of death in the United States. There is an ever-growing need for accurate analysis of oncogenic markers for the diagnosis and prognosis of cancer. For example, detection of an array of oncogenic markers may allow physicians to detect early stage cancer and to monitor cancer progression. With knowledge of a patient's responsiveness to anticancer therapies prior to drug initiation, physicians could select the best course of treatment for each individual patient. Furthermore, routine analysis of drug effectiveness during the course of treatment may reveal a patient's unresponsiveness to specific anti-cancer drugs. This information could be used to improve the selection of drug treatment regimens.

Current methods for oncogenic marker analysis are based on interrogating malignant cells in a heterogeneous mixture of normal and cancer cells such as whole blood. Methods such as the LeukoLOCK Total RNA Isolation System (Ambion) capture circulating malignant cells from whole blood by passing a blood sample through disposable leukocyte depletion filters. Typically, these depletion filters are flushed with buffers such as PBS as the malignant cells are recovered. This wash step changes the intracellular concentration of anticancer drugs previously exposed to the cells, thereby possibly causing de novo signaling responses within the cells and altering expression of oncogenic markers. Consequently, expression of oncogenic markers in the analyzed sample could inaccurately reflect a patient's response to specific anticancer therapies. This could lead to incorrect diagnostic and/or prognostic evaluations. The present invention overcomes this potential source of error by providing methods and apparatuses for isolating a subset of blood cells without changing the intracellular concentration of an anti-cancer drug.

BRIEF SUMMARY OF THE INVENTION

The present invention provides apparatuses and methods for isolating, harvesting, and/or recovering a subset of blood cells such as normal leukocytes, diseased leukocytes, malignant leukocytes, leukemia cells, foam cells, and/or circulating tumor cells (CTCs) from a blood sample by filtration without changing the intracellular (in vivo) concentration of a therapeutic agent i.e., anticancer drug (e.g., a tyrosine kinase inhibitor). In certain aspects, the present invention provides cell isolation apparatuses comprising a filtration device and a collection tube.

In one aspect, the present invention provides an apparatus for isolating and separating leukocytes from red blood cells in a whole blood sample, the apparatus comprising:
a filtration device comprising an upper chamber, a lower chamber, and one or more stacked filter membranes between the upper and lower chambers, wherein the one or more stacked filter membranes are capable of retaining the leukocytes; and
a collection tube for collecting the red blood cells from the whole blood sample, wherein the filtration device is placed on top of the collection tube, and wherein the red blood cells are separated from the leukocytes and are collected in the collection tube following centrifugation. In a preferred aspect, the lower chamber is disposed between the upper chamber and the collection tube.

In another embodiment, the present invention provides a method for preparing a lysate of leukocytes from a whole blood sample without substantial dilution of a therapeutic agent (e.g., an anticancer drug), the method comprising:
(a) loading the whole blood sample into a cell isolation (filtration) apparatus such as an apparatus as described herein;
(b) centrifuging the apparatus to capture the leukocytes on the one or more stacked filter membranes to separate red blood cells into a collection tube; and
(c) lysing the leukocytes captured on the one or more stacked filter membranes with lysis buffer but without a wash step between steps (b) and (c) to thereby prepare a lysate of leukocytes.

In another aspect, the present invention provides a method for monitoring the efficacy of an anticancer drug in a subject, wherein the subject has a hematological malignancy, comprising:
administering the anticancer drug to the subject, wherein the first administration of the anticancer drug is at time $T_1$;
measuring the activation state and or expression level of BCR-ABL at a time $T_2$ in a sample from the subject; and
determining a course of treatment based upon the activation state and or expression level of BCR-ABL.

In certain embodiments, the method further comprises measuring the activation state of BCR-ABL at $T_0$, i.e., prior to the first administration of the anticancer drug. In certain instances, the hematological malignancy is a lymphoma or a leukemia such as chronic myelogenous leukemia (CML). The time difference between $T_1$ and $T_2$ is about 1 week to about 6 months such as 1, 2, 3, 4, 5, 6, 7, 8, 9, 10, 11, 12, 13, 14, 15, 16, 17, 18, 19, 20, 21, 22, 23, or 24 week(s). The time difference between $T_0$ and $T_1$ is about 1 day to about 3 weeks. In certain other aspects, the methods further include measuring expression and or activation levels of at least one other signal transduction molecule such as CRKL, AKT, STAT5 and SRC.

In certain aspects, the course of treatment is selected from changing the anticancer drug dose, changing the anti-cancer drug, including an additional anticancer drug, changing the length of treatment and staying the existing course of treatment.

In certain aspects, the sample comprises an extract of isolated cells. In certain aspects, the isolated cells are incubated in vitro with at least one anticancer drug (e.g., 2 anticancer drugs) at $T_0$ (prior to initiation of treatment). In other instances, the isolated cells are incubated in vitro with at least two anticancer drugs at $T_2$, prior to determining the course of treatment.

In yet another embodiment, the present invention provides a method for selecting an anticancer drug in a subject having a hematological malignancy:
measuring the activation state level of BCR-ABL in an isolated cell from a sample from the subject;

incubating the isolated cell with at least one anticancer drug prior to initiation of treatment;

measuring the activation state level of BCR-ABL in the incubated cells; and selecting a course of treatment based upon the activation state level of BCR-ABL.

In certain aspects, the course of treatment is selected from the group consisting of selecting the anticancer drug, selecting the anticancer dose, and determining the length of treatment. In certain other aspects, the methods further include measuring expression and or activation levels of at least one other signal transduction molecule such as CRKL, AKT, STAT5 and SRC.

As such, the present invention provides: a method for selecting an anticancer drug in a subject having a hematological malignancy, the method comprising:

1) measuring the activation state level of BCR-ABL in an isolated cell from a sample from the subject;
2) incubating the isolated cell with at least one anticancer drug prior to initiation of treatment;
3) measuring the activation state level of BCR-ABL in the incubated cells; and selecting a course of treatment based upon the activation state level of BCR-ABL.

The present invention also provides a method for monitoring the efficacy of an anticancer drug in a subject, wherein the subject has a hematological malignancy, the method comprising:

a) measuring the activation state of BCR-ABL at $T_0$, prior to the first administration of the anticancer drug;
b) administering the anticancer drug to the subject, wherein the first administration of the anticancer drug is at time $T_1$;
c) measuring the activation state and or expression level of BCR-ABL at a time $T_2$ in a sample from the subject; and
d) determining a course of treatment based upon the activation state and or expression level of BCR-ABL.

Other objects, features, and advantages of the present invention will be apparent to one of skill in the art from the following detailed description and figures.

BRIEF DESCRIPTION OF THE DRAWINGS

FIG. 2A-G illustrate an embodiment cell isolation apparatus. FIG. 2A is an embodiment of an upper chamber. FIG. 2B-C show an upper chamber with cap; FIG. 2D-E is a lower chamber; and FIG. 2F-G is a collection tube.

FIG. 4A-D illustrate embodiments of the cell isolation apparatus. FIG. 4A is an embodiment of the upper and lower chamber; FIG. 4B is an embodiment of the upper and lower chamber; FIG. 4C is an embodiment of a collection tube; and FIG. 4D is an embodiment of an aggregation of an upper chamber, a lower chamber and a collection tube.

FIG. 5A is an embodiment of the upper and lower chamber; FIG. 5B is an embodiment of the upper and lower chamber with cap; FIG. 5C is an embodiment of a collection tube with cap; and FIG. 5D is an embodiment of a lower chamber and funnel.

FIG. 6A-C illustrate yet another embodiment of the cell isolation apparatus. FIG. 6A is an embodiment of the upper and lower chamber; FIG. 6B is an embodiment of the upper and lower chamber with a middle sleeve; FIG. 6C is an embodiment of a lower chamber.

FIG. 7B shows the levels of phosphorylated BCR-ABL in K562 cells after filtration are comparable to the levels detected in unprocessed cells.

FIG. 8B shows that the percentage recovery of total and phosphorylated BCR-ABL in different samples that were centrifuged at various speeds can be compared. The highest percentage of phospho-BCR-ABL (63.60%) and total BCR-ABL (141.55%) signal recovered was from using PALL filtration membrane and centrifuging at 600 rpm.

FIG. 9B shows total BCR-ABL recovery.

FIG. 10 tabulates patients analyzed in one embodiment of the invention. Patient 1 has active CML and has been receiving treatment since December 2006. Patient 2 who also has active CML has been receiving imatinib treatment since January.

FIG. 12A-B show the detection of activated (phosphorylated) levels of BCR-ABL as determined by methods described herein. Cell lysate samples isolated from Patient 1 were diluted 1:5 and 1:20 according to the methods described in Example 6. The standard sample represents untreated K562 cell lysates with varying # of cells per 80 µl of lysate (e.g, 10000, 3000, 1000, 300, 100, 30, 10, or 0 cells/80 µl). The top panel of FIG. 12A shows the images of the BCR-ABL CEER Assays.

FIG. 13A shows the images of the BCR-ABL CEER Assays.

FIG. 15 B is after subtraction of blood background.

FIG. 18A shows that in vitro incubation of Patient 2's blood sample with 1004 nilotinib was the most effective treatment at reducing the % recovery of phospho BCR-ABL signal. Phosphorylated BCR-ABL levels were detected and measured following an in vitro treatment of patient blood samples with different dosages of BCR-ABL inhibitors for 1.5 hours at 37° C. FIG. 18B shows that increasing dosages of nilotinib decreases activated BCR-ABL while imatinib has no effect on Patient 2's blood sample. The % recovery of phospho BCR-ABL signal decreased to 39.35% with 10 µM nilotinib, and only 96.46% with 10 µM imatinib.

FIG. 20A-B show that phospho CRKL level (CU/ml of blood) decreased in Patient 1 samples in vitro treated with either 10 µM imatinib or 10 µM nilotinib, as compared to the non-treated sample. Similarly, FIG. 20C-D show that in Patient 1 samples, the percentage of phospho CRKL signal decreased upon in vitro treatment. A similar response was not seen in Patient 2 samples.

FIG. 21A-B show the results as calculated as picograms of activated AKT per 1000 cells assayed. FIG. 21C-D shows the results as determined as a percentage of AKT signal recovered from the CEER Assay.

FIG. 23A-B illustrate phospho-SRC levels as calculated as picograms per 1000 cells assayed.

FIG. 24 represents a list of patients who participated in this study. The patients were diagnosed with CML and received targeted treatment. In vivo modulations of BCR-ABL inhibition via CEER Assay were monitored in these patients FIG. 25 represents a list of some patients who participated in this study. An asterisk indicates a blood sample that was processed using the tube embodiment of the cell isolation apparatus of the present invention. The other blood samples were processed using the 96-well embodiment.

FIG. 28A shows that the pBCR-ABL/WBC ratio dropped in the blood drawn on 5/11 and was increasing by 10/12. An asterisk indicates that the pBCR-ABL data was multiplied by 10 to make the value visible on the graph. FIG. 28B shows that the pBCR-ABL/total BCR-ABL ratio was lowest on 5/11. FIG. 28C shows results of quantitative RT-PCR analysis using the MolecularMD kit for BCR-ABL and low levels of mRNA. The percentage of BCR-ABL/ABL varies with the amount of mRNA present in the sample.

FIG. 29B shows the change in total and activated BCR-ABL levels and mRNA percentages.

FIG. 30B shows the change in total and activated BCR-ABL levels and mRNA percentages after treatment was changed from imatinib to dasatinib.

DETAILED DESCRIPTION OF THE INVENTION

I. Introduction

Figure 1:
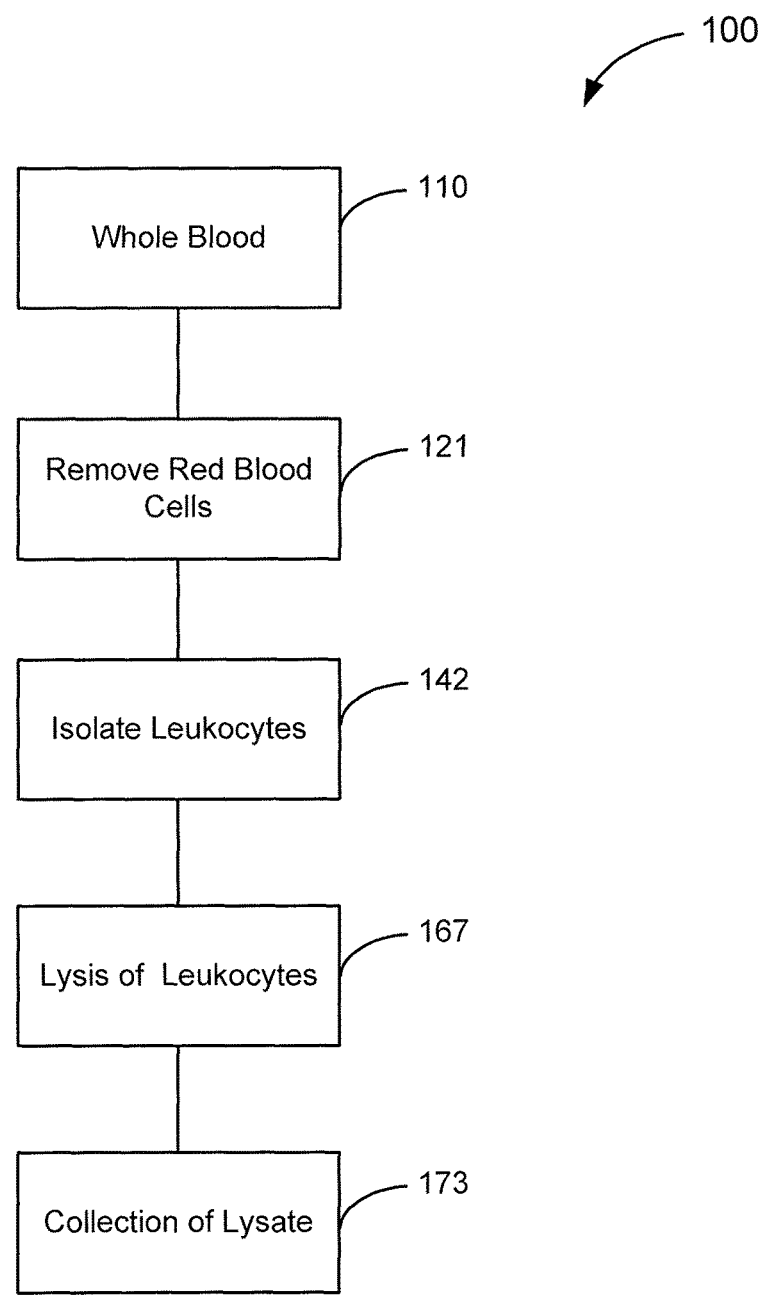
FIG. 1 illustrates a flow diagram of one embodiment of the present invention.

The present invention advantageously provides novel apparatuses and methods for isolating or recovering a subset of blood cells such as normal and/or malignant leukocytes, leukemia cells, foam cells, and/or circulating tumor cells (CTCs) from blood samples by filtration without changing the intracellular concentration of a therapeutic agent such as an anticancer drug (e.g., a tyrosine kinase inhibitor such as, e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof). Contrary to the art, the apparatuses and methods of the present invention provide cell lysates from recovered cells such as leukocytes, leukemia cells, foam cells, and/or circulating tumor cells without substantial dilution of a therapeutic agent such as an anticancer drug (e.g., a tyrosine kinase inhibitor).

The BCR-ABL fusion protein is associated with chronic myelogenous leukemia (CML) as well as acute lymphoblastic leukemia (ALL). In particular, the BCR-ABL protein is an active tyrosine kinase that is critical to cancer pathogenesis. Although imatinib (Gleevec®) is currently the first line therapy for newly diagnosed patients with CML, about 20-25% of patients do not achieve durable complete cytogenetic responses. Studies have shown that the reactivation of BCR-ABL kinase activity in the presence of continued imatinib treatment is the major cause of resistance. As such, the measurement of BCR-ABL activity finds utility in predicting response to therapy with tyrosine kinase inhibitors such as imatinib as well as in identifying patients who develop resistance to such inhibitors.

In certain embodiments, the apparatuses and methods of the present invention can be used to isolate or recover cells of interest (e.g., leukocytes, leukemia cells, foam cells, and/or circulating tumor cells) from a sample such as blood and prepare lysates therefrom, wherein analytes such as, e.g., BCR-ABL that are present in the resulting cell lysate can be interrogated for their expression and/or activation levels using an assay such as a Collaborative Enzyme Enhanced Reactive-immunoassay (CEER™) (also known as COllaborative Proximity ImmunoAssay (COPIA)). CEER™ is described in the following patent documents which are herein incorporated by reference in their entirety for all purposes: PCT Publication No. WO 2008/036802; PCT Publication No. WO 2009/012140; PCT Publication No. WO 2009/108637; PCT Publication No. WO 2010/132723; PCT Publication No. WO 2011/008990; and PCT Application No. PCT/US2010/053386, filed Oct. 20, 2010.

In particular embodiments, expression/activation profiling of one or more oncogenic fusion proteins, substrates thereof, and/or other signal transduction pathway proteins (e.g., BCR-ABL, BCR, ABL, CRKL, JAK2, STAT5, Src, FAK, c-ABL, c-CBL, SHC, SHP-2, VAV, BAP-1, AKT, SRC, EGFR, HER-2, HER-3, HER-4, VEGFR-1, VEGFR-2, VEGFR-3, PDGFR, c-Met, c-KIT, IGF-IR, PI3K, etc.) can be performed on cell lysates prepared using the apparatuses and methods of the present invention to determine the efficacy of inhibitor therapy for patients with BCR-ABL mediated diseases (e.g., chronic myelogenous leukemia). In some instances, patients may be receiving inhibitor therapy such as treatment with tyrosine kinase inhibitors as described herein. In particular instances, leukemia cells are isolated from blood samples of such patients without substantial dilution of the tyrosine kinase inhibitor. In certain other instances, the expression/activation profiling of oncogenic fusion proteins and/or signal transduction pathway components in a sample following in vitro treatment with tyrosine kinase inhibitors can provide valuable information to enable a clinician to select an effective therapeutic regimen.

As a non-limiting example, a blood sample from a patient receiving tyrosine kinase inhibitor therapy can be analyzed to determine the effectiveness of the therapy. The patient's blood can be drawn and cells of interest such as leukocytes, leukemia cells, and/or circulating tumor cells are isolated by filtration using the apparatuses and methods of the invention. The cells are then lysed and interrogated using an assay such as CEER™ to determine the effect of tyrosine kinase inhibitor treatment on the activation state and/or total amount of one or a plurality of oncogenic fusion proteins (e.g., BCR-ABL), substrates thereof (e.g., BCR-ABL substrates such as CRKL, JAK2, STAT5, Src, FAK, c-ABL, c-CBL, SHC, SHP-2, VAV, and/or BAP-1), and/or other signal transduction molecules. In particular embodiments, the number of leukocytes, leukemia cells, and/or circulating tumor cells and the profile of phosphorylated BCR-ABL and other signaling transduction pathway components can be determined. The phosphorylation signal ratio can also be calculated from the analysis and used to determine the patient's prognosis. In particular embodiments, the efficacy of tyrosine kinase inhibitor therapy can be monitored in a patient by administering a tyrosine kinase inhibitor at time $T_1$, measuring the activation state and/or expression level of BCR-ABL at a time $T_2$ in a sample from the patient, and determining a course of treatment based upon the activation state and/or expression level of BCR-ABL.

As another non-limiting example, a blood sample from a patient (e.g., not receiving tyrosine kinase inhibitor treatment) can be in vitro incubated with one or more inhibitors prior to isolation of leukocytes, leukemia cells and/or circulating tumor cells (CTCs). In particular instances, whole blood samples harvested from patients diagnosed with CML are treated with one or more tyrosine kinase inhibitors (e.g., imatinib, nilotinib, dasatinib, etc.). Cells of interest such as leukemia cells are isolated by filtration using the apparatuses and methods of the present invention. The cells are then lysed and interrogated using an assay such as, e.g., CEER™ to determine the effect of tyrosine kinase inhibitor treatment on the activation state and/or total amount of one or a plurality of oncogenic fusion proteins (e.g., BCR-ABL), substrates thereof (e.g., BCR-ABL substrates such as CRKL, JAK2, STAT5, Src, FAK, c-ABL, c-CBL, SHC, SHP-2, VAV, and/or BAP-1) and/or other signal transduction molecules. In particular embodiments, a suitable tyrosine kinase inhibitor can be selected for the patient based upon measuring the activation state or level of BCR-ABL in isolated cells from the sample, incubating the isolated cells with at least one anticancer drug such as one or more tyrosine kinase inhibitors prior to initiation of treatment, measuring the activation state or level of BCR-ABL in the incubated cells, and selecting a course of treatment based upon the activation state or level of BCR-ABL.

II. Definitions

As used herein, the following terms have the meanings ascribed to them unless specified otherwise.

The term "cancer" includes any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Non-limiting examples of different types of cancer include hematological malignancies (e.g., leukemia, lymphoma); osteogenic sarcomas (e.g., Ewing sarcoma); soft tissue sarcomas (e.g., Dermatofibrosarcoma Protuberans (DFSP), rhabdomyosarcoma); other soft tissue malignancies, papillary thyroid carcinomas; prostate cancer; gastric cancer (e.g., stomach); breast cancer; lung cancer (e.g., non-small cell lung cancer); digestive and gastrointestinal cancers (e.g., colorectal cancer, gastrointestinal stromal tumors, gastrointestinal carcinoid tumors, colon cancer, rectal cancer, anal cancer, bile duct cancer, and small intestine cancer); esophageal cancer; gallbladder cancer; liver cancer; pancreatic cancer; appendix cancer; ovarian cancer; renal cancer (e.g., renal cell carcinoma); cancer of the central nervous system;

skin cancer; choriocarcinomas; and head and neck cancers. As used herein, a "tumor" comprises one or more cancerous cells.

A "hematological malignancy" includes any type of cancer that affects the blood, bone marrow, and/or lymph nodes. Examples of hematological malignancies include, but are not limited to, leukemia, lymphoma, and multiple myeloma. Non-limiting examples of different kinds of leukemia include chronic myelogenous leukemia (CML), acute lymphoblastic leukemia (ALL), chronic lymphocytic leukemia (CLL), acute myelogenous leukemia (AML), and large granular lymphocytic leukemia. Subtypes of CML include, e.g., chronic monocytic leukemia. Subtypes of ALL include, e.g., precursor B-cell acute lymphoblastic leukemia, pro-B-cell acute lymphoblastic leukemia, precursor T-cell acute lymphoblastic leukemia, and acute biphenotypic leukemia. Subtypes of CLL include, e.g., B-cell prolymphocytic leukemia. Subtypes of AML include, e.g., acute promyelocytic leukemia, acute myeloblastic leukemia, and acute megakaryoblastic leukemia. Examples of different kinds of lymphoma include, but are not limited to, Hodgkin's lymphoma (four subtypes) and non-Hodgkin lymphoma, such as, e.g., small lymphocytic lymphoma (SLL), diffuse large B-cell lymphoma (DLBCL), follicular lymphoma (FL), mantle cell lymphoma (MCL), hairy cell leukemia (HCL), marginal zone lymphoma (MZL), Burkitt's lymphoma (BL), post-transplant lymphoproliferative disorder (PTLD), T-cell prolymphocytic leukemia (T-PLL), B-cell prolymphocytic leukemia (B-PLL), Waldenström's macroglobulinemia (also known as lymphoplasmacytic lymphoma), and other NK- or T-cell lymphomas.

The term "analyte" includes any molecule of interest, typically a macromolecule such as a polypeptide, whose presence, amount, and/or identity is determined. In certain instances, the analyte is a cellular component of a cancerous cell, preferably an oncogenic fusion protein or a signal transduction molecule.

The term "transform" or "transforming" includes a physical and/or chemical change of an analyte or sample to extract the analyte or to change or modify the analyte as defined herein. As used herein, an extraction, a manipulation, a chemical precipitation, an ELISA, a complexation, an immuno-extraction, a physical or chemical modification of the analyte or sample to measure a level or concentration or activation state of an analyte all constitute a transformation. In other words, as long as the analyte or sample is not identical before and after the transformation step, the change or modification is a transformation.

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "fusion protein" or "chimeric protein" includes a protein created through the joining of two or more genes which originally encode separate proteins. Such gene fusions are typically generated when a chromosomal translocation replaces the terminal exons of one gene with intact exons from a second gene. This creates a single gene which can be transcribed, spliced, and translated to produce a functional fusion protein. In particular embodiments, the fusion protein is an oncogenic fusion protein, i.e., a fusion protein involved in oncogenesis. Examples of oncogenic fusion proteins include, but are not limited to, BCR-ABL, DEK-CAN, E2A-PBX1, RARα-PML, IREL-URG, CBFβ-MYH11, AML1-MTG8, EWS-FLI, LYT-10-Cα1, HRX-ENL, HRX-AF4, NPM-ALK, IGH-MYC, RUNX1-ETO, TEL-TRKC, TEL-AML1, MLL-AF4, TCR-RBTN2, COL1A1-PDGF, E2A-HLF, PAX3-FKHR, ETV6-NTRK3, RET-PTC, TMRSS-ERG, and TPR-MET.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER-1/ErbB1, HER-2/Neu/ErbB2, HER-3/ErbB3, HER-4/ErbB4), VEGFR-1/FLT-1, VEGFR-2/FLK-1/KDR, VEGFR-3/FLT-4, FLT-3/FLK-2, PDGFR (e.g., PDGFRA, PDGFRB), c-Met, c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, RTK 106, and truncated forms of the receptor tyrosine kinases such as p95ErbB2; non-receptor tyrosine kinases such as Src, Frk, Btk, Csk, Abl, Zap70, Fes/Fps, Fak, Jak, Ack, and LIMK; tyrosine kinase signaling cascade components such as Akt, MAPK/ERK, MEK, RAF, PLA2, MEKK, JNKK, JNK, p38, She (p66), PI3K, Ras (e.g., K-Ras, N-Ras, H-Ras), Rho, Rac1, Cdc42, PLC, PKC, p70 S6 kinase, p53, cyclin D1, STAT1, STAT3, PIP2, PIP3, PDK, mTOR, BAD, p21, p27, ROCK, IP3, TSP-1, NOS, PTEN, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors; and combinations thereof.

The term "sample" as used herein includes any biological specimen obtained from a patient. Samples include, without limitation, whole blood, plasma, serum, ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), and cellular extracts thereof. In some embodiments, the sample is whole blood or a fractional component thereof such as plasma, serum, red blood cells, leukocytes such as peripheral blood mononuclear cells, and/or rare circulating cells. In particular embodiments, the sample is obtained by isolating leukocytes or circulating cells of a solid tumor from whole blood or a cellular fraction thereof using any technique known in the art. In other embodiments, the sample is a formalin fixed paraffin embedded (FFPE) tumor tissue sample, e.g., from a solid tumor.

As used herein, the term "circulating cells" comprises extratumoral cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.).

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The term "subject" or "patient" or "individual" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays of the present invention typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract of leukocytes or rare circulating cells. In preferred embodiments, the capture antibody is restrained on a solid support in an array. Suitable capture antibodies for immobilizing any of a variety of oncogenic fusion proteins or signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of oncogenic fusion proteins or signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, Akt, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more oncogenic fusion proteins or signal transduction molecules. In some embodiments, the phosphorylation of the ABL kinase domain of the BCR-ABL fusion protein is detected using an activation state-dependent antibody. In other embodiments, the phosphorylation of members of the EGFR family of receptor tyrosine kinases and/or the formation of heterodimeric complexes between EGFR family members is detected using activation state-dependent antibodies.

Non-limiting examples of activation states of oncogenic fusion proteins that are suitable for detection with activation state-dependent antibodies include phosphorylated forms of BCR-ABL, DEK-CAN, E2A-PBX1, RARα-PML, IREL-URG, CBFβ-MYH11, AML1-MTG8, EWS-FLI, LYT-10-Cal, HRX-ENL, HRX-AF4, NPM-ALK, IGH-MYC, RUNX1-ETO, TEL-TRKC, TEL-AML1, MLL-AF4, TCR-RBTN2, COL1A1-PDGF, E2A-HLF, PAX3-FKHR, ETV6-NTRK3, RET-PTC, TMRSS-ERG, and TPR-MET. Examples of activation states (listed in parentheses) of signal transduction molecules that are suitable for detection with activation state-dependent antibodies include, but are not limited to, EGFR (EGFRvIII, phosphorylated (p-) EGFR, EGFR:Shc, ubiquitinated (u-) EGFR, p-EGFRvIII); ErbB2 (p95:truncated (Tr)-ErbB2, p-ErbB2, p95:Tr-p-ErbB2, HER-2:Shc, ErbB2:PI3K, ErbB2:EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); c-Met (p-c-Met or c-Met/HGF complex), ER (p-ER (S118, S167); IGF-1R (p-IGF-1R, IGF-1R:IRS, IRS:PI3K, p-IRS, IGF-1R:PI3K); INSR (p-INSR); KIT (p-KIT); FLT3 (p-FLT3); HGFR1 (p-HGFR1); HGFR2 (p-HGFR2); RET (p-RET); PDGFRa (p-PDGFRa); PDGFRP (p-PDGFRP); VEGFR1 (p-VEGFR1, VEGFR1:PLCg, VEGFR1:Src); VEGFR2 (p-VEGFR2, VEGFR2:PLCy, VEGFR2:Src, VEGFR2:heparin sulfate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); Tie1

(p-Tie1); Tie2 (p-Tie2); EphA (p-EphA); EphB (p-EphB); NFKB and/or IKB (p-IK (S32), p-NFKB (S536), p-P65: IKBa); Akt (p-Akt (T308, S473)); PTEN (p-PTEN); Bad (p-Bad (S112, S136), Bad:14-3-3); mTor (p-mTor (S2448)); p70S6K (p-p70S6K (T229, T389)); Mek (p-Mek (S217, S221)); Erk (p-Erk (T202, Y204)); Rsk-1 (p-Rsk-1 (T357, S363)); Jnk (p-Jnk (T183, Y185)); P38 (p-P38 (T180, Y182)); Stat3 (p-Stat-3 (Y705, S727)); Fak (p-Fak (Y576)); Rb (p-Rb (S249, T252, S780)); Ki67; p53 (p-p53 (S392, S20)); CREB (p-CREB (S133)); c-Jun (p-c-Jun (S63)); cSrc (p-cSrc (Y416)); and paxillin (p-paxillin (Y118)).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more oncogenic fusion proteins or signal transduction molecules.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "tyrosine kinase inhibitor" includes any of a variety of therapeutic agents or drugs that act as selective or non-selective inhibitors of receptor and/or non-receptor tyrosine kinases. Without being bound to any particular theory, tyrosine kinase inhibitors generally inhibit target tyrosine kinases by binding to the ATP-binding site of the enzyme. Examples of tyrosine kinase inhibitors include, but are not limited to, imatinib (Gleevec®; STI571), nilotinib (Tasigna®), dasatinib (Sprycel®), bosutinib (SKI-606), gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), leflunomide (SU101), vandetanib (Zactima™; ZD6474), ponatinib (AP24534), derivatives thereof, analogs thereof, and combinations thereof. Additional tyrosine kinase inhibitors suitable for use in the present invention are described in, e.g., U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340. One of skill in the art will know of other tyrosine kinase inhibitors suitable for use in the present invention. In certain instances, the tyrosine kinase inhibitor is administered in a pharmaceutically acceptable form including, without limitation, an alkali or alkaline earth metal salt such as an aluminum, calcium, lithium, magnesium, potassium, sodium, or zinc salt; an ammonium salt such as a tertiary amine or quaternary ammonium salt; and an acid salt such as a succinate, tartarate, bitartarate, dihydrochloride, salicylate, hemisuccinate, citrate, isocitrate, malate, maleate, mesylate, hydrochloride, hydrobromide, phosphate, acetate, carbamate, sulfate, nitrate, formate, lactate, gluconate, glucuronate, pyruvate, oxalacetate, fumarate, propionate, aspartate, glutamate, or benzoate salt.

The term "incubating" is used synonymously with "contacting" and "exposing" and does not imply any specific time or temperature requirements unless otherwise indicated.

The term "course of therapy" includes any therapeutic approach taken to relieve or prevent one or more symptoms associated with a cancer such as a hematological malignancy (e.g., leukemia, lymphoma, etc.). The term encompasses administering any compound, drug, procedure, and/or regimen useful for improving the health of an individual with cancer and includes any of the therapeutic agents described herein. One skilled in the art will appreciate that either the course of therapy or the dose of the current course of therapy can be changed (e.g., increased or decreased) based upon the expression and/or activation levels of one or more oncogenic fusion proteins and/or signal transduction molecules determined using the methods of the present invention.

III. Description of the Embodiments

The present invention advantageously provides novel apparatuses and methods for isolating or recovering a subset of blood cells such as, e.g., leukocytes (e.g., normal and/or malignant leukocytes), leukemia cells, foam cells, and/or circulating tumor cells (CTCs) from blood samples by filtration without changing the intracellular concentration of a therapeutic agent such as an anticancer drug (e.g., a tyrosine kinase inhibitor such as, e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof). Contrary to the art, the apparatuses and methods of the present invention provide cell lysates from recovered cells such as leukocytes, leukemia cells, foam cells, and/or circulating tumor cells without substantial dilution of a therapeutic agent such as an anticancer drug (e.g., a tyrosine kinase inhibitor).

In certain instances, the present invention provides apparatuses and methods for isolating tumor cells from a homogenate, lysate, or cellular extract of a solid tumor.

In particular embodiments, the apparatuses and methods of the present invention substantially remove plasma, which contains proteases and phosphatases that can degrade or desphosphorylate target proteins such as analytes of interest, and also substantially remove interfering proteins that can affect target protein assays.

FIG. 1 represents one embodiment of a method to isolate and harvest tumor cells of the present invention. Those of skill in the art will recognize other changes and modifications to the method within the scope of the present invention.

In one method 100, tumor cells from a patient such as a patient suffering from CML (optionally being treated) are isolated and harvested. As shown in FIG. 1, whole blood is collected 110 and filtered to remove red blood cells. In certain instances, the whole blood from patients can be treated or non-treated with an anticancer drug, such as a BCR-ABL inhibitor, prior to isolation. Advantageously, the methods herein ensure that the amount and concentration of the inhibitor or therapeutic agent present in the cells in vivo is maintained in vitro. In certain aspects, the present invention provides a method for preparing a lysate of leukocytes from a whole blood sample without substantial dilution or essentially no dilution of a therapeutic agent such as an anticancer drug. The collected whole blood is loaded into an apparatus as described herein. In certain aspects, the blood is freshly drawn prior to isolation of the leukocytes. If a fresh blood sample is unavailable, blood samples can be processed within a period such as 3 hours, 6 hours, 12 hours, 18 hours, 24 hours (1 day), 36 hours, 48 hours, and the like after being drawn. Samples are typically kept at room temperature prior to processing. In certain aspects, a protease and/or phosphatase inhibitor can be added to the blood sample 110. Thereafter, the blood is mixed by for example, gently inverting up and down in a tube or vial.

Afterwards, the erythrocytes are removed 121 typically by centrifugation through a filter or membrane. In certain aspects, an especially designed filtration apparatus is used as shown herein. Preferably, the erythrocytes are present in the collection tube after centrifugation. In one aspect, the method includes centrifuging the vial or tube apparatus to capture or isolate the leukocytes 142 on a filter membrane such as a stacked collection of filter membranes (one or more filters), and to separate red blood cells (and plasma) into a collection tube.

After filtration or centrifugation of the red blood cells (and plasma), a lysis buffer is used to lyse the captured leukocytes 167. In one aspect, protein later lysis buffer can be used. After capture, the leukocytes are thereafter lysed, but without a wash step after capture to thus prepare a lysate of leukocytes. The therapy concentration in the whole blood cells is the same before and after the procedure 100. In some instances, the therapy concentration is 10 µM before procedure 100 and 10 µM after procedure 100. In other instances, the therapy concentration is 1 µM before procedure 100 and 1 µM after procedure 100. In yet other instances, the therapy concentration is 0.1 µM before procedure 100 and 0.1 µM after procedure 100. The lysate is then collected 173 in a second collection tube, e.g., by centrifugation. The lysate from the leukocytes is without substantial dilution or essentially no dilution of a therapeutic agent such as an anticancer drug. That is, the in vivo cellular concentration of a therapeutic agent (e.g., anticancer drug) is essentially or substantially the same as the in vitro concentration of the therapeutic agent (e.g., anticancer drug) in the cell lysate.

In another aspect, the present invention provides a method for preparing a lysate of leukocytes (e.g., normal, malignant, and/or diseased leukocytes) from a whole blood sample without substantial dilution of a therapeutic agent (e.g., an anticancer drug), the method comprising:
   (a) loading the whole blood sample into a cell isolation (filtration) apparatus such as an apparatus as described herein;
   (b) centrifuging the apparatus to capture the leukocytes on the one or more stacked filter membranes and to separate red blood cells (and plasma) into a collection tube; and
   (c) lysing the leukocytes captured on the one or more stacked filter membranes with lysis buffer but without a wash step between steps (b) and (c) to thereby prepare a lysate of leukocytes.

In certain embodiments, the method of the invention further comprises replacing the collection tube with a second collection tube between steps (b) and (c). In certain other embodiments, the method of the invention further comprises centrifuging the apparatus containing the second collection tube after lysing the leukocytes in step (c) and collecting the lysate of leukocytes in the second collection tube.

In some embodiments, the whole blood sample is obtained from a subject receiving a therapeutic agent (e.g., an anticancer drug). In other embodiments, the whole blood sample is incubated in vitro with a therapeutic agent (e.g., an anticancer drug) prior to loading into the apparatus.

In further embodiments, the whole blood sample is obtained from a subject having or suspected of having atherosclerosis or receiving treatment for atherosclerosis (e.g., statin therapy). In other embodiments, the whole blood sample is obtained from a subject having or suspected of having a cancer such as a hematological malignancy (e.g., a leukemia such as chronic myelogenous leukemia (CML)) or receiving treatment for the cancer (e.g., anticancer drug therapy).

In particular embodiments, the expression and/or activation level of at least one oncogenic fusion protein and/or signal transduction molecule is measured in the lysate of leukocytes. In preferred embodiments, the at least one oncogenic fusion protein is BCR-ABL. Additional examples of oncogenic fusion proteins and/or signal transduction molecules of interest are described herein.

As such, in one aspect, the present invention provides an apparatus for isolating and separating leukocytes (e.g., normal, malignant, and/or diseased leukocytes) from red blood cells (and plasma) in a whole blood sample, the apparatus comprising:
   a filtration device comprising an upper chamber, a lower chamber, and one or more stacked filter membranes between the upper and lower chambers, wherein the one or more stacked filter membranes are capable of retaining the leukocytes; and
   a collection tube for collecting the red blood cells (and plasma) from the whole blood sample, wherein the filtration device is placed on top of the collection tube, and wherein the red blood cells (and plasma) are separated from the leukocytes and are collected in the collection tube following centrifugation.

In some embodiments, the whole blood sample is loaded into the upper chamber of the filtration device. In other embodiments, the filtration device comprises two, three, or four stacked filter membranes. In certain embodiments, the upper chamber further comprises a snap-cap lid attached thereto.

In further embodiments, the apparatus further comprises a second collection tube, wherein the (first) collection tube containing the red blood cells (and plasma) is replaced with the second collection tube following (a first) centrifugation. In some instances, a lysate of the leukocytes is collected in the second collection tube following the addition of lysis buffer to the upper chamber and (a second) centrifugation. In particular instances, the lysis buffer is added to the upper chamber without washing the one or more stacked filter membranes. In some embodiments, the lysis buffer is incubated above the filter for at least 1, 5, 10, 15, 20, 30, 60, or 120 minutes, preferably between about 15 to about 30 minutes, at 4° C. (or on ice) prior to centrifugation and collection in the second collection tube.

In alternative embodiments, the apparatus further comprises a second collection tube, wherein the one or more stacked filter membranes are removed from the filtration device (e.g., with forceps) following centrifugation and placed into the second collection tube. In some instances, the second collection tube contains lysis buffer, and the leukocytes are lysed after the one or more stacked filter membranes are placed or incubated into the second collection tube.

In certain instances, the lysate prepared using the apparatus of the present invention comprises a cellular extract of normal and/or malignant (e.g., cancerous) leukocytes such as granulocytes (polymorphonuclear leukocytes), which include, e.g., neutrophils, basophils, and eosinophils; agranulocytes (mononuclear leukocytes), which include, e.g., peripheral blood mononuclear cells such as lymphocytes and monocytes, leukemia cells, which include, e.g., chronic myelogenous leukemia (CML) cells; macrophages, which include, e.g., foam cells; and mixtures thereof.

In certain embodiments, the leukocytes, leukemia cells, foam cells, circulating cells, or other cells present in the whole blood sample can be stimulated in vitro with one or more growth factors before, during, and/or after incubation with one or more therapeutic agents such as one or more anticancer drugs of interest. Stimulatory growth factors include, but are not limited to, epidermal growth factor (EGF), heregulin (HRG), TGF-α, PlGF, angiopoietin (Ang), NRG1, PGF, TNF-α, VEGF, PDGF, IGF, FGF, HGF, cytokines, and the like. Protocols for the stimulation and lysis of cells found in whole blood are described in PCT Publication No. WO 2008/036802, which is incorporated herein by reference in its entirety for all purposes.

In certain embodiments, the whole blood sample is obtained from a subject having or suspected of having cancer. In some instances, the cancer may be caused by the formation of an oncogenic fusion protein due to a chromosomal translocation in the cancer cells. Non-limiting examples of such cancers include a hematological malignancy, an osteogenic sarcoma, a soft tissue sarcoma, and combinations thereof. In particular embodiments, the hematological malignancy is a leukemia or lymphoma. In one preferred embodiment, the leukemia is chronic myelogenous leukemia (CML). In other instances, the subject is either receiving or not receiving anticancer drug therapy.

In certain other embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the isolated cells are treated with one or more anti-signaling agents, anti-proliferative agents, and/or hormonal therapeutic agents in combination with at least one chemotherapeutic agent.

Examples of anti-signaling agents include, without limitation, monoclonal antibodies such as trastuzumab (Herceptin®), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as imatinib mesylate (Gleevec®), nilotinib) (Tasigna®, dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), ponatinib (AP24534), and vandetanib (ZACTIMA™; ZD6474); and combinations thereof.

Exemplary anti-proliferative agents include mTOR inhibitors such as sirolimus (rapamycin), temsirolimus (CCI 779), and everolimus (RAD001); Akt inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)methyl)-4-piperidinyl)-2H-benzimidazol-2-one, 10-(4'-(N-diethylamino)butyl)-2-chlorophenoxazine, 3-formylchromone thiosemicarbazone (Cu(II)Cl$_2$ complex), API-2, a 15-mer peptide derived from amino acids 10-24 of the proto-oncogene TCL1 (Hiromura et al., J. Biol. Chem., 279:53407-53418 (2004), KP372-1, and the compounds described in Kozikowski et al., J. Am. Chem. Soc., 125:1144-1145 (2003) and Kau et al., Cancer Cell, 4:463-476 (2003); and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine)(Gemzar®, pemetrexed) (ALIMTA®), raltitrexed, etc.), plant alkaloids (e.g., vincristine, vinblastine, vinorelbine, vindesine, podophyllotoxin, paclitaxel) (Taxol®), docetaxel) (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines include ANYARA from Active Biotech, DCVax-LB from Northwest Biotherapeutics, EP-2101 from IDM Pharma, GV1001 from Pharmexa, 10-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In certain other embodiments, the whole blood sample is obtained from a subject having or suspected of having atherosclerosis (also known as arteriosclerotic vascular disease or ASVD). Atherosclerosis is a disease typically affecting arterial blood vessels, a chronic inflammatory response in the walls of arteries, caused largely by the accumulation of macrophages such as foam cells and promoted by low-density lipoproteins (plasma proteins that carry cholesterol and triglycerides) without adequate removal of fats and cholesterol from the macrophages by functional high density lipoproteins (HDL). Examples of drugs suitable for the treatment of atherosclerosis include, without limitation, statins such as atorvastatin (Lipitor and Torvast), fluvastatin (Lescol), lovastatin (Mevacor, Altocor, Altoprev), mevastatin (Compactin), pitavastatin (Livalo, Pitava), pravastatin (Pravachol, Selektine, Lipostat), rosuvastatin (Crestor), simvastatin (Zocor, Lipex), combinations thereof, as well as combination preparations such as ezetimibe and simvastatin (Vytorin), lovastatin and niacin (Advicor), atorvastatin and amlodipine besylate (Caduet), and simvastatin and niacin (Simcor). In some instances, the subject is either receiving or not receiving therapy with an atherosclerosis drug such as a statin.

In other embodiments, the whole blood sample is incubated in vitro with one or more therapeutic agents such as one or more anticancer drugs prior to isolation of leukocytes. In particular embodiments, leukocytes that are retained or captured on the filter membranes comprise normal leukocytes, malignant leukocytes, or combinations thereof.

In particular embodiments, the apparatuses of the invention provide for preparing the lysate or cellular extract from whole blood samples by recovering or isolating cells of interest such as malignant leukocytes (e.g., chronic myelogenous leukemia (CML) cells) without any wash steps after cell recovery or isolation. The cellular extract thus obtained can be analyzed for the level of expression and/or activation of one or more oncogenic fusion proteins such as BCR-ABL, substrates thereof, pathways thereof, or combinations thereof. Without being bound to any particular theory, eliminating the need for any wash steps after cell isolation is advantageous because cells of interest can be recovered from blood without changing the intracellular concentration of a therapeutic agent such as an anticancer drug (e.g., a tyrosine kinase inhibitor). As set forth in the Examples below, cell isolation using the apparatuses described herein without any wash steps is contrary to the art-accepted practice of washing cells after isolation and provides cellular extracts from recovered cells without substantial dilution of a therapeutic agent such as an anticancer drug (e.g., a tyrosine kinase inhibitor such as, e.g., Gleevec®, Tasigna®, Sprycel®, etc.) inside the cells.

In particular embodiments, the apparatuses of the present invention are substantially similar or identical to the apparatus depicted herein. One skilled in the art will appreciate that the dimensions of one or more components of the apparatus described herein and illustrated can be varied, taking into account parameters such as, for example, the volume of sample to be loaded into the apparatus, the type of centrifuge to be used to spin the apparatus, the volume of lysis buffer to be added to the upper chamber of the apparatus, etc.

Turning now to FIG. 2A-G, as shown therein, there is a filtration device or apparatus for sample collection. FIG. 2A is the upper portion or chamber of the apparatus 201 which is a cylindrical tube with male helical ridges or threads 210. The upper portion with cap 215 is shown in FIG. 2B-C. This upper portion 201 can optionally have a cap 215 that snaps shut to prevent spilling of the sample. In certain embodiments, the snap-cap lid 215 is tethered via strap 217 to the upper portion and can be used to securely close the opening of the upper chamber after a sample and/or a reagent is added to the filtration device. The upper chamber 201 of the apparatus of the present invention preferably attaches to a lower camber portion or chamber 222 as shown in FIG. 2 D-E. The threads 210 of the upper portion fit securely into female grooves 221 of the lower portion or chamber 222. Preferably, the inner diameters of the upper and lower chambers are similar as to create a cylindrical tube which allows liquids to pass therethrough.

In certain aspects, the lower chamber 222 of the filtration device or apparatus is a cylindrical tube with an internal screw thread at one end 221 (FIG. 2E). In certain aspects, one or more (e.g., a plurality such as two, three, four, five, six, seven, eight, nine, ten, or more) stacked filter membranes is placed between the screw threads of the upper chamber and lower chamber before the chambers are securely attached together. The filter(s) sits on pin wheel 225 of the lower chamber as shown in FIG. 2E.

In particular aspects, the filter membranes can be 2-4 (e.g., 2, 3, or 4) layers of filters such as Pall filters (e.g., Leukosorb Medium). In other aspects, the filtration device is an assembly of separate chambers and filters which are joined together prior to use such as in a kit. The filtration device can be placed on top of a collection tube 250 as shown in FIG. 2F-G for the separation of red blood cells (and plasma) from a patient blood sample. The portions of FIG. 2A, FIG. 2D and FIG. 2F join or fit together to form one embodiment of the apparatus filtration device of the present invention. The filtration device (upper and lower chambers) can be placed on top of a collection vessel 250 for the separation of red blood cells from a patient blood sample. The lower chamber of the assembled filtration device is positioned in the collection vessel via opening 255 and the upper chamber is on top of the opening of the collection vessel. Examples of collection vessel 250 include, but are not limited to, tubes such as plastic culture tubes having a capacity of 1 ml, 2 ml, 3 ml, 4 ml, 5 ml, 6 ml, 7 ml, 8 ml, 14 ml, 16 ml and the like.

Figure 3C:
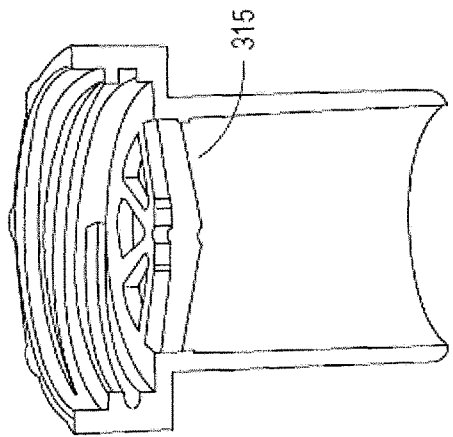
FIG. 3A-E illustrate embodiments of the lower chamber with various funnel functionality.
Figure 3B:
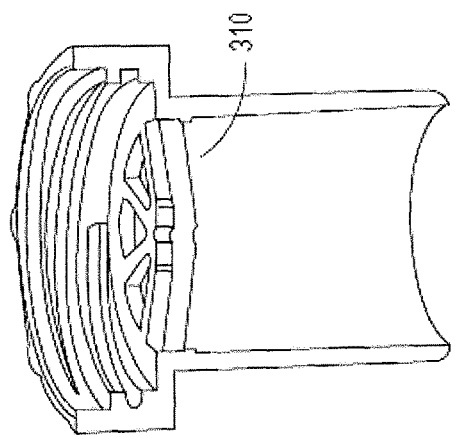
Figure 3A:
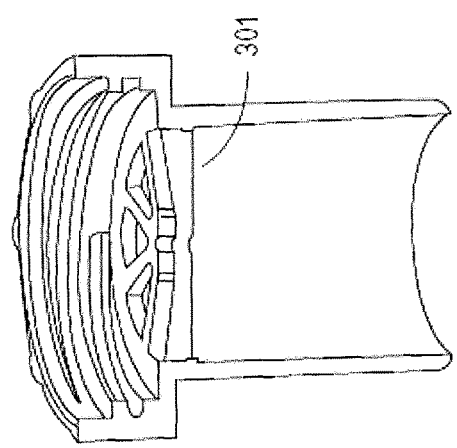
Figure 3D:
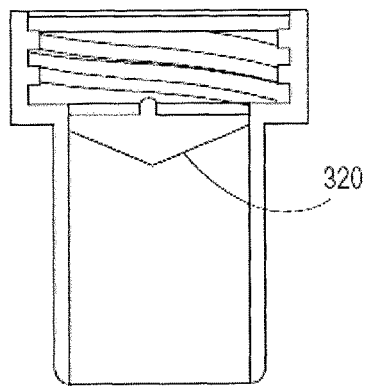
Figure 3E:
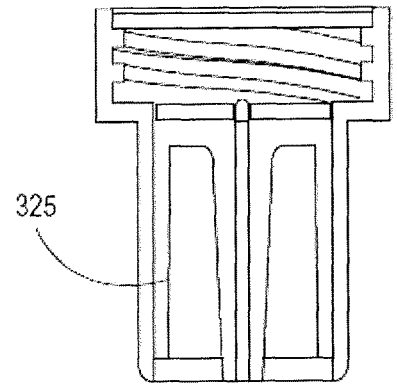

In certain aspects, the lower portion of the filtration device of the present invention has a built-in or optional funnel in the lower portion. As shown in FIG. 3A-E, the funnel may have a certain angular dimension to ensure that the sample passes into and through the lower chamber into the collection tube without going down the inner wall of the lower portion. For example, FIG. 3A shows a internal funnel 301 of about 2° off the horizontal. FIG. 3B shows an internal funnel 310 of approximately 7° off the horizontal. In certain other aspects, FIG. 3C shows a funnel approximately 12° off the horizontal. FIG. 3D and FIG. 3E are yet other embodiments of the funnel design of the present invention. A skilled artisan will understand and appreciate that the funnel design can be any angle such that the filtrate stays off the walls of the lower portion. Suitable angles include 1°, 2°, 3°, 4°, 5°, 6°, 7°, 8°, 9°, 10°, 11°, 12°, 13°, 14°, 15°, 16°, 17°, 18°, 19°, 20° or more for the funnel portion. In an alternative embodiment, FIG. 3E shows a funnel insert 325 into the lower portion of a filtration device of the present invention.

In certain aspects, the filtration device of the present invention is shown in FIG. 4A-D. FIG. 4A shows the exploded view of the upper portion or chamber 410, a lower portion or chamber 420 and a filter stack 412 in-between. In FIG. 4A, view 405 is looking down on the device and view 422 is looking up at the device. FIG. 4B shows the upper portion 430 and the lower chamber or portion 420 screwed together. In FIG. 4B, view 405 is looking down on the device and view 425 is looking up at the device. FIG. 4C shows collection tube 435. In operation, in certain aspects, collection tube 435 preferably holds red blood cells. In FIG. 4C, view 434 is looking down on the device and view 440 is looking up at the device. FIG. 4D depicts the collection tube 435 joined with the upper chamber 410 and lower chamber or portion 420. In FIG. 4D, view 405 is looking down on the device and view 461 is looking up at the device.

In some embodiments, in operation, a volume (e.g., 1 ml) of patient blood treated with a solution mixture comprising a protease and/or a phosphatase inhibitors is loaded into the upper chamber of an assembled cell isolation apparatus. The apparatus can be centrifuged in a tabletop or clinical centrifuge, such as an Allegra 6R centrifuge (Beckman), Sorvall Legend centrifuge (Thermo Scientific), or Heraeus Megafuge centrifuge (Kendro). In some aspects, the apparatus is centrifuged for 5-30 minutes at 600-2,000 rpms at 4° C. After centrifugation, the collection vessel containing the red blood cells (and plasma) is removed from the cell isolation apparatus, capped and set aside.

In further embodiments, a second collection vessel is attached to the filtration device. Non-limiting examples of a second collection tube for the cell lysate include 1.5 ml and 2 ml microcentrifuge tubes. Without a washing step, lysis buffer is added to the upper chamber of the filtration device. The upper chamber is capped and the filtration device and second collection tube are shaken vigorously. In certain instances, the cell isolation apparatus is incubated at 4° C. for at least 1, 5, 10, 15, 20, 30, 60, or 120 minutes, preferably between about 15 to about 30 minutes. The apparatus can then be centrifuged (e.g., 3,000 rpm for 5 min). The cell lysate can be transferred to another centrifuge vessel such as a microcentrifuge tube for storage at −70° C.

Figure 5A:
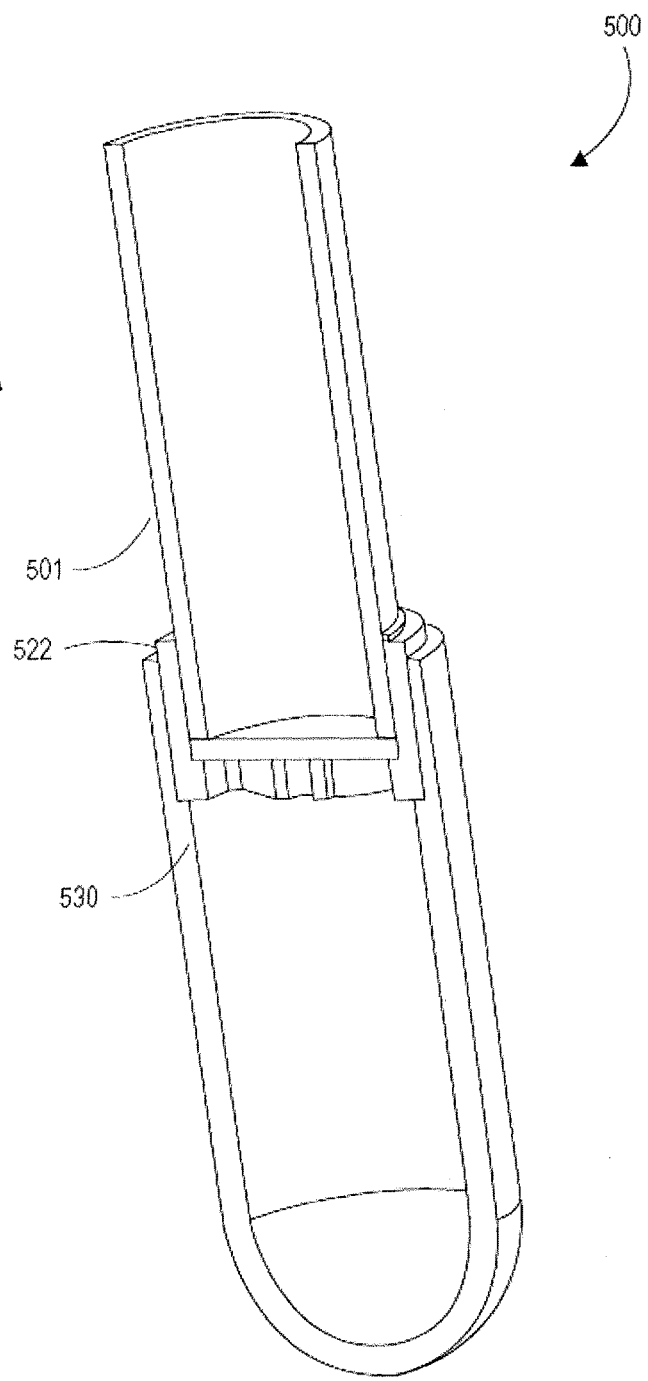
FIG. 5A-D illustrates another embodiment of the cell isolation apparatus.
Figure 5B:
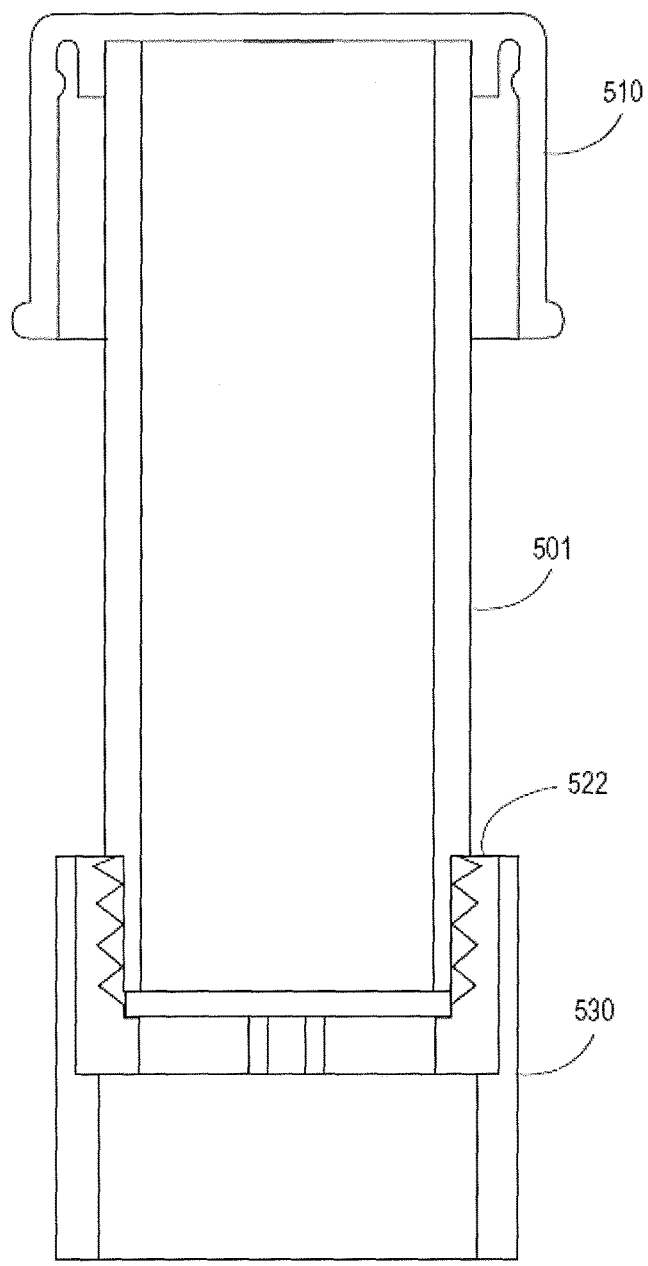
Figure 5C:
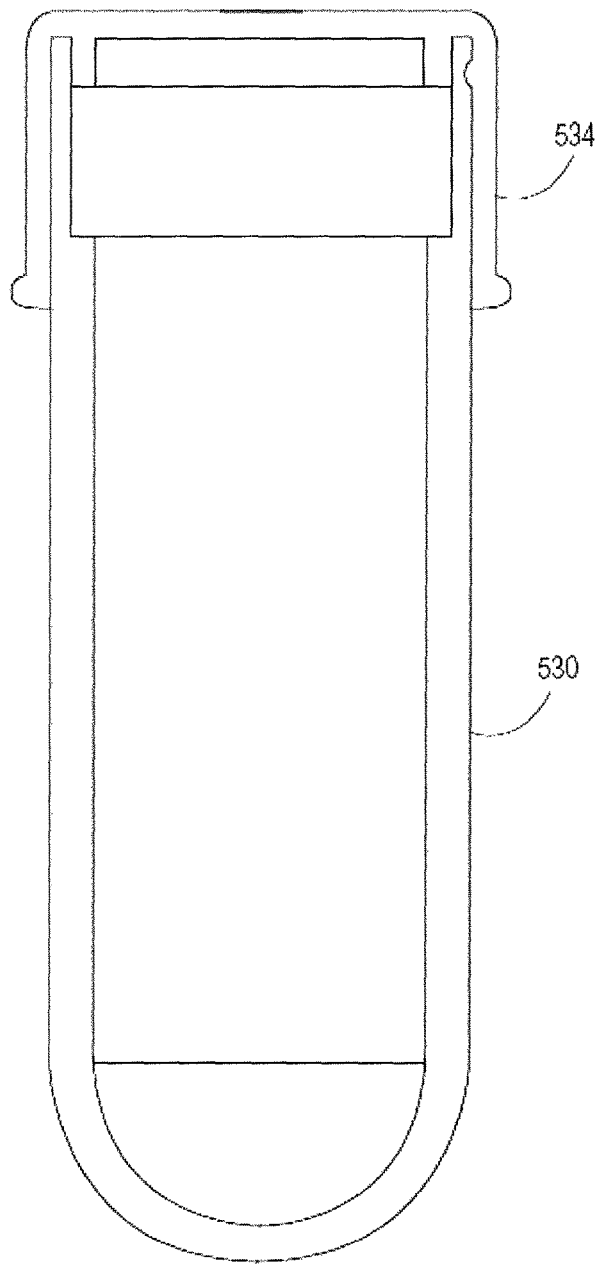
Figure 5D:
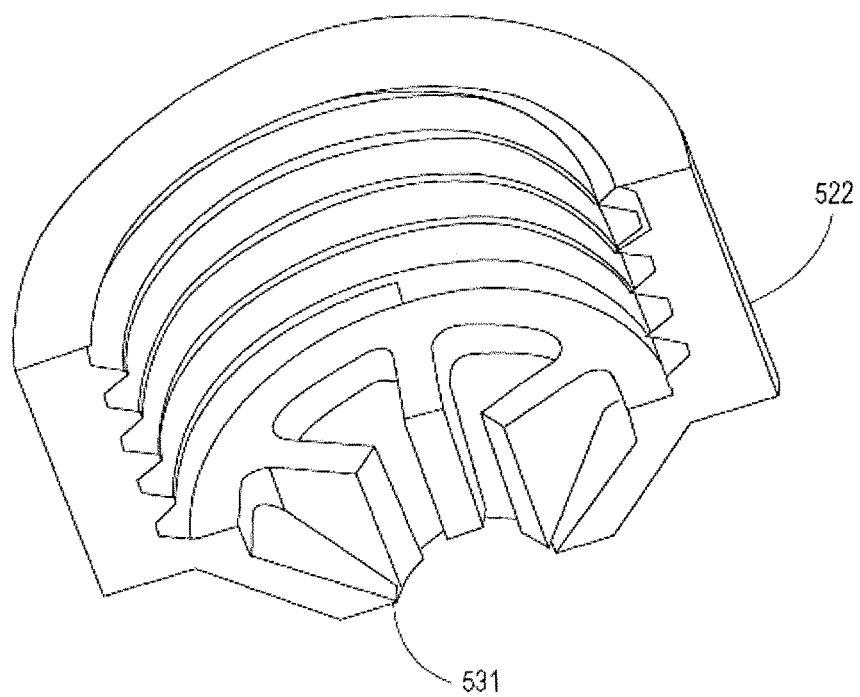

FIG. 5A-D show an alternative embodiment of the filtration device or apparatus 500 for sample collection of the present invention. In this embodiment, there is an upper portion 501 and a bottom portion or chamber 530 with a sleeve or middle connector 522. The middle connector or sleeve 522 can optionally be fixed to either the upper 501 or bottom portion 530. As shown in FIG. 5B, in certain aspects, the upper portion has ridges or male ridges and can be fixed to the sleeve or bottom portion. In FIG. 5B, the apparatus is shown with cap 510. FIG. 5C shows that the bottom portion 530 can optionally have a cap 534 to keep this portion sealed. FIG. 5D depicts a lower chamber or portion 522 clearly showing female grooves. This portion can optionally be fixed to the bottom portion such that the sleeve in integral to the bottom portion of the device.

FIG. 6A-C show yet another aspect of the present invention. FIG. 6 A is a cross-sectional view of a device of the present invention, wherein the bottom portion 610 is joined with the upper portion 625 with sleeve 633 enabling joinder. Inset FIG. 6B is a close up of the portions joined together with threads 625 and middle section 633 with a funnel section, Collection chamber 610 is also shown. FIG. 6C shows middle section with pinwheel geometry. The filter stack optionally sits on this pinwheel.

In other further embodiments, after the cell isolation apparatus is centrifuged and the red blood cells are collected and set aside in the collection tube, the upper chamber and lower chamber of the filtration device are separated (e.g., unscrewed). Using forceps, the filter membranes 422 (FIG. 4A) containing the separated leukocytes and/or circulating tumor cells are placed in a second collection vessel containing cell lysis buffer. Non-limiting examples of a second collection vessel include 1.5 ml and 2 ml microcentrifuge tubes. In some instances, the second collection vessel is further incubated at 4° C. for at least 1, 5, 10, 15, 20, 30, 60, or 120 minutes, preferably between about 15 to about 30 minutes. In other aspects, the second collection vessel is placed on ice and briefly vortexed for 10 seconds every 10 minutes for a total of 30 minutes. In some embodiments, the cell lysate is stored at −70° C. In other embodiments, the vessel containing the lysate is centrifuged to remove the filter membranes and cell fragments. The supernatant of the cell lysate can be transferred to another tube for storage at −70° C.

In some embodiments, the apparatuses of the invention are provided as a sterile kit. In some instances, the sterile kit comprises a filtration device comprising an upper chamber (optionally with an attached snap-cap lid), lower chamber and a stack of one or more filter membranes (e.g, 1, 2, 3, or 4 layers of filter membrane), and one or a plurality of collection tubes (optionally with snap-cap lids). Each of the components can be packaged separately and the kit assembled or each of the components can be placed in to a sterile package. In other instances, the sterile kit comprises a tube filter unit and one or a plurality of collection tubes (optionally with snap-cap lids). The tube filter unit comprises a cylindrical tube affixed at one end with one or more (e.g., a plurality of two, three, four, five, six, seven, eight, nine, ten, or more) filter membranes, wherein the membranes are able to retain healthy and malignant leukocytes and/or circulating tumor cells from whole blood samples. In particular instances, the filter membranes are (e.g., 2, 3, or 4) layers of filters such as PALL filters (e.g., Leukosorb Medium). In yet other instances, the sterile kit comprises a tube filter unit, a plastic adaptor and one or a plurality of collection tubes (optionally with snap-cap lids). The adaptor is positioned in the opening of a collection tube and securely attached to the filter membrane of the tube filter unit.

In further embodiments, the apparatus of the present invention comprises a plurality of filtration devices or tube filter units and a multi-well or multi-tube collection vessel such as a 2-well, 12-well, 24-well, 48-well, or 96-well plate. In certain instances, the plurality of filtration devices can be substantially similar to at least two or more of the devices as depicted in FIG. 4D. In certain other embodiments, the array of filtration devices can be a multi-well plate such as a 96-well cell isolation plate. For example, a first 96-well filtration plate can be fitted with filter membranes (e.g., LeukoLOCK (Life Technologies), or Acroprep (PALL) or Leukosorb (PALL)) or membranes substantially similar thereto. In other embodiments, the first 96-well filtration plate is substantially similar to or is a commercially available multi-well plate fitted with filter membranes, such as but not limited to, Millipore Cat. #MAMIC8510 and #MSBCS1210. In some instances, the commercially available multi-well plates are sterile and comprise a first multi-well plate fitted with filter membranes and a second multi-well plate that fits under the first multi-well plate and can be used as a collection vessel. In these embodiments, fresh collected blood can be loaded into wells of a first 96-well cell isolation plate. The first multi-well plate is analogous to both the upper and lower chambers of the filtration device discussed above. A second 96-well microplate can serve as a blood collection plate (which is analogous to the collection tube) and can be placed under the first multi-well plate i.e., the cell isolation plate with filter membranes. This plate assembly can be centrifuged at room temperature for about 5 min at a speed ranging from about 600 rpm to 3,000 rpm, such as e.g., about 600 rpm, 1,000 rpm, 2,000 rpm, and 3,000 rpm. After centrifugation, the filter membrane can be transferred to a centrifugation tube and the cells on the filter membrane can be treated with a volume of lysis buffer (e.g., 300 µl of lysis buffer) and vortexed briefly, in order to lyse the cells. The centrifugation tube containing the cell lysate can be placed on ice for about 30 min and subjected to brief vortexing about every 10 minutes. Thereafter the tube can be centrifuged for about 15 minutes to separate the cellular debris from the supernatant. The supernatant containing the lysate can be collected and analyzed. In certain aspects, the plurality of filtration devices are manipulated with robotic armature under computer control. High throughput sample analysis is carried-out and the plurality of samples is analyzed. Steps of procedure 100, such as the addition of lysis buffer to lyse the captured leukocytes 167, are optionally performed with a computerized robotic system. In some aspects, in vitro treatment of patient blood sample with anticancer drug and sample analysis as described herein are performed in a high throughput manner.

IV. Drug Selection and Optimization for Cancer Therapy

In certain aspects, the present invention provides methods for monitoring the efficacy of cancer therapy in subjects with a hematological malignancy. In certain aspects, the present invention provides methods for the selection of appropriate therapies to down-regulate or shut down one or more deregulated signaling pathways. In certain other aspects, the present invention provides methods for optimizing therapy and/or reducing toxicity in a subject having cancer and receiving a course of therapy for the treatment of cancer. Thus, the present invention may be used to facilitate the design of personalized therapies based on the particular molecular signature provided by the collection of activated oncogenic fusion proteins and/or signal transduction proteins in a given patient's cancer or tumor.

Accordingly, in one particular aspect, the present invention provides a method for monitoring the efficacy of an anticancer drug in a subject, wherein the subject has a hematological malignancy, comprising:
 (a) administering the anticancer drug to the subject, wherein the first administration of the anticancer drug is at time $T_1$;
 (b) isolating cells of a cancer at a time $T_2$ in a sample from the subject;
 (c) lysing the isolated cells to produce a cellular extract;
 (d) measuring the activation state and or expression level of an oncogenic fusion protein at a time $T_2$ in a sample from the subject; and
 determining a course of treatment based upon the activation state and or expression level of the oncogenic fusion protein.

In certain embodiments, the method further comprises measuring the activation state of the oncogenic fusion protein at $T_0$, i.e., prior to the first administration of the anticancer drug. In some instances, the oncogenic fusion protein is BCR-ABL. In certain instances, the hematological malignancy is a lymphoma or a leukemia such as chronic myelogenous leukemia (CML). The time difference between $T_1$ and $T_2$ is about 1 week to about 6 months such as 1, 2, 3, 4, 5, 6, 7, 8, 9, 10, 11, 12, 13, 14, 15, 16, 17, 18, 19, 20, 21, 22, 23, or 24 week(s). The time difference between $T_0$ and $T_1$ is about 1 day to about 3 weeks. In certain other aspects, the methods further include measuring expression and or activation levels of at least one other signal transduction molecule such as CRKL, AKT, STAT5 and SRC.

In certain aspects, the course of treatment is selected from changing the anticancer drug dose, changing the anti-cancer drug, including an additional anticancer drug, changing the length of treatment and staying the existing course of treatment.

In certain aspects, the sample comprises an extract of isolated cells. In certain aspects, the isolated cells are incubated in vitro with at least one anticancer drug (e.g., 2 anticancer drugs) at $T_0$ (prior to initiation of treatment). In other instances, the isolated cells are incubated in vitro with at least two anticancer drugs at $T_2$, prior to determining the course of treatment.

In yet other embodiments, the present invention provides a method for selecting an anticancer drug in a subject having a hematological malignancy:
 (a) isolating cells of a cancer from a subject;
 (b) lysing the isolated cells to produce a cellular extract;
 (c) measuring the activation state level of an oncogenic fusion protein in an isolated cell from a sample from the subject;
 (d) incubating the isolated cell with at least one anticancer drug prior to initiation of treatment;
 (e) lysing the isolated cells incubated with at least one anticancer drug prior to initiation of treatment to produce a cellular extract;
 (f) measuring the activation state level of the oncogenic fusion protein in the incubated cells; and
 (g) selecting a course of treatment based upon the activation state level of the oncogenic fusion protein.

In another embodiment, the present invention provides a method for selecting an anticancer drug in a subject having a hematological malignancy:
 (a) isolating cells of a cancer from a subject;
 (b) lysing the isolated cells to produce a cellular extract;
 (c) measuring the activation state level of BCR-ABL in an isolated cell from a sample from the subject;
 (d) incubating the isolated cell with at least one anticancer drug prior to initiation of treatment;
 (e) lysing the isolated cells incubated with at least one anticancer drug prior to initiation of treatment to produce a cellular extract;
 (f) measuring the activation state level of BCR-ABL in the incubated cells; and
 (g) selecting a course of treatment based upon the activation state level of BCR-ABL.

In certain aspects, the course of treatment is selected from the group consisting of selecting the anticancer drug, selecting the anticancer dose, and determining the length of treatment. In certain other aspects, the methods further include measuring expression and or activation levels of at least one other signal transduction molecule such as CRKL, AKT, STAT5 and SRC.

In another aspect, the present invention provides a method for optimizing therapy and/or reducing toxicity in a subject having cancer and receiving a course of therapy for the treatment of cancer, the method comprising:
 (a) isolating cancer cells after administration of an anticancer drug (e.g., one or more tyrosine kinase inhibitors such as Gleevec®, Tasigna®, Sprycel®, etc.);
 (b) lysing the isolated cells to produce a cellular extract;
 (c) measuring a level of expression and/or activation (e.g., phosphorylation) of an oncogenic fusion protein in the cellular extract using an assay described herein; and
 (d) comparing the measured level of expression and/or activation of the oncogenic fusion protein to a level of expression and/or activation of the oncogenic fusion protein measured at an earlier time during the course of therapy; and
 (e) determining a subsequent dose of the course of therapy for the subject or whether a different course of therapy should be administered to the subject based upon the comparison from step (d).

In particular embodiments, both total and activated (e.g., phosphorylated) oncogenic fusion protein (e.g., BCR-ABL) levels are measured in the cellular extract in accordance with the antibody-based assays of the present invention and a ratio of activated to total oncogenic fusion protein levels (e.g., ratio of phospho/total BCR-ABL protein levels) can be calculated and used to evaluate the course of therapy for a subject, e.g., by comparing the phospho/total ratio of oncogenic fusion protein levels to a ratio of the same calculated for the subject at an earlier time (e.g., at an earlier time while on anticancer drug therapy or at a point in time prior to anticancer drug therapy).

In another aspect, the present invention provides a method for selecting a suitable anticancer drug for the treatment of a cancer, the method comprising:
  (a) isolating cells of a cancer after administration of an anticancer drug, or prior to incubation with an anticancer drug;
  (b) lysing the isolated cells to produce a cellular extract;
  (c) determining a level of expression and/or activation (e.g., phosphorylation) of an oncogenic fusion protein in the cellular extract using an assay described herein; and
  (d) determining whether the anticancer drug is suitable or unsuitable for the treatment of the cancer by comparing the level of expression and/or activation detected for the oncogenic fusion protein with a reference expression and/or activation profile generated in the absence of the anticancer drug.

In a preferred embodiment, the method for selecting a suitable anticancer drug for the treatment of a cancer comprises:
  (a) isolating cells of a cancer after administration of an anticancer drug, or prior to incubation with an anticancer drug;
  (b) lysing the isolated cells to produce a cellular extract;
  (c) determining a level of expression and/or activation (e.g., phosphorylation) of an oncogenic fusion protein in the cellular extract using an assay comprising a dilution series of capture antibodies specific for the oncogenic fusion protein, wherein the capture antibodies are restrained on a solid support;
  (d) comparing the level of expression and/or activation detected for the oncogenic fusion protein with a reference expression and/or activation profile generated in the absence of the anticancer drug; and
  (e) indicating that the anticancer drug is suitable for the treatment of the cancer when the level of expression and/or activation detected for the oncogenic fusion protein is changed (e.g., substantially decreased) compared to the reference expression and/or activation profile.

In some embodiments, the methods of the present invention may be useful to aid or assist in the selection of a suitable anticancer drug for the treatment of a cancer such as, e.g., a hematological malignancy. In other embodiments, the methods of the present invention may be useful for improving the selection of a suitable anticancer drug for the treatment of a cancer such as, e.g., a hematological malignancy. In certain embodiments, the method further or alternatively comprises the step of indicating that the anticancer drug is unsuitable for the treatment of the cancer when the level of expression and/or activation detected for the oncogenic fusion protein is not changed (e.g., not substantially decreased) compared to the reference expression and/or activation profile. In further embodiments, one or more signal transduction molecules present in the cellular extract are detected in addition to one or more oncogenic fusion proteins, and the anticancer drug is determined to be suitable or unsuitable based on this "molecular profile."

In yet another aspect, the present invention provides a method for identifying the response of a cancer to treatment with an anticancer drug, the method comprising:
  (a) isolating cells of a cancer after administration of an anticancer drug, or prior to incubation with an anticancer drug;
  (b) lysing the isolated cells to produce a cellular extract;
  (c) determining a level of expression and/or activation (e.g., phosphorylation) of an oncogenic fusion protein in the cellular extract using an assay described herein; and
  (d) identifying the cancer as responsive or non-responsive to treatment with the anticancer drug by comparing the level of expression and/or activation detected for the oncogenic fusion protein with a reference expression and/or activation profile generated in the absence of the anticancer drug.

In a preferred embodiment, the method for identifying the response of a cancer to treatment with an anticancer drug comprises:
  (a) isolating cells of a cancer after administration of an anticancer drug, or prior to incubation with an anticancer drug;
  (b) lysing the isolated cells to produce a cellular extract;
  (c) determining a level of expression and/or activation (e.g., phosphorylation) of an oncogenic fusion protein in the cellular extract using an assay comprising a dilution series of capture antibodies specific for the oncogenic fusion protein, wherein the capture antibodies are restrained on a solid support;
  (d) comparing the level of expression and/or activation detected for the oncogenic fusion protein with a reference expression and/or activation profile generated in the absence of the anticancer drug; and
  (e) indicating that the cancer is responsive to treatment with the anticancer drug when the level of expression and/or activation detected for the oncogenic fusion protein is changed (e.g., substantially decreased) compared to the reference expression and/or activation profile.

In some embodiments, the methods of the present invention may be useful to aid or assist in the identification of the response of a cancer such as, e.g., a hematological malignancy, to treatment with an anticancer drug. In other embodiments, the methods of the present invention may be useful for improving the identification of the response of a cancer such as, e.g., a hematological malignancy, to treatment with an anticancer drug. In certain embodiments, the method further or alternatively comprises the step of indicating that the cancer is non-responsive to treatment with the anticancer drug when the level of expression and/or activation detected for the oncogenic fusion protein is not changed (e.g., not substantially decreased) compared to the reference expression and/or activation profile. In further embodiments, one or more signal transduction molecules present in the cellular extract are detected in addition to one or more oncogenic fusion proteins, and the cancer is identified as responsive or non-responsive to treatment based on this "molecular profile."

In still yet another aspect, the present invention provides a method for predicting the response of a subject having cancer to treatment with an anticancer drug, the method comprising:
  (a) isolating cells of a cancer after administration of an anticancer drug, or prior to incubation with an anticancer drug;
  (b) lysing the isolated cells to produce a cellular extract;

(c) determining a level of expression and/or activation (e.g., phosphorylation) of an oncogenic fusion protein in the cellular extract using an assay described herein; and (d) predicting the likelihood that the subject will respond to treatment with the anticancer drug by comparing the level of expression and/or activation detected for the oncogenic fusion protein with a reference expression and/or activation profile generated in the absence of the anticancer drug.

In a preferred embodiment, the method for predicting the response of a subject having cancer to treatment with an anticancer drug comprises:

(a) isolating cells of a cancer after administration of an anticancer drug, or prior to incubation with an anticancer drug;

(b) lysing the isolated cells to produce a cellular extract;

(c) determining a level of expression and/or activation (e.g., phosphorylation) of an oncogenic fusion protein in the cellular extract using an assay comprising a dilution series of capture antibodies specific for the oncogenic fusion protein, wherein the capture antibodies are restrained on a solid support;

(d) comparing the level of expression and/or activation detected for the oncogenic fusion protein with a reference expression and/or activation profile generated in the absence of the anticancer drug; and (e) indicating that the subject will likely respond to treatment with the anticancer drug when the level of expression and/or activation detected for the oncogenic fusion protein is changed (e.g., substantially decreased) compared to the reference expression and/or activation profile.

In some embodiments, the methods of the present invention may be useful to aid or assist in the prediction of a subject's likelihood of responding to treatment with an anticancer drug for a cancer such as, e.g., a hematological malignancy. In other embodiments, the methods of the present invention may be useful for improving the prediction of a subject's likelihood of responding to treatment with an anticancer drug for a cancer such as, e.g., a hematological malignancy. In certain embodiments, the method further or alternatively comprises the step of indicating that the subject will not likely respond to treatment with the anticancer drug when the level of expression and/or activation detected for the oncogenic fusion protein is not changed (e.g., not substantially decreased) compared to the reference expression and/or activation profile. In further embodiments, one or more signal transduction molecules present in the cellular extract are detected in addition to one or more oncogenic fusion proteins, and the likelihood that the subject will respond to treatment is predicted based on this "molecular profile."

In a further aspect, the present invention provides a method for determining whether a subject having cancer is resistant to treatment with an anticancer drug, the method comprising:

(a) isolating cells of a cancer after administration of an anticancer drug, or prior to incubation with an anticancer drug;

(b) lysing the isolated cells to produce a cellular extract;

(c) determining a level of expression and/or activation (e.g., phosphorylation) of an oncogenic fusion protein in the cellular extract using an assay described herein; and (d) determining whether the subject is resistant or sensitive to treatment with the anticancer drug by comparing the level of expression and/or activation detected for the oncogenic fusion protein with a reference expression and/or activation profile generated in the absence of the anticancer drug or in the presence of the anticancer drug at an earlier time.

In a preferred embodiment, the method for determining whether a subject having cancer is resistant to treatment with an anticancer drug comprises:

(a) isolating cells of a cancer after administration of an anticancer drug, or prior to incubation with an anticancer drug;

(b) lysing the isolated cells to produce a cellular extract;

(c) determining a level of expression and/or activation (e.g., phosphorylation) of an oncogenic fusion protein in the cellular extract using an assay comprising a dilution series of capture antibodies specific for the oncogenic fusion protein, wherein the capture antibodies are restrained on a solid support;

(d) comparing the level of expression and/or activation detected for the oncogenic fusion protein with a reference expression and/or activation profile generated in the absence of the anticancer drug or in the presence of the anticancer drug at an earlier time; and (e) indicating that the subject is resistant to treatment with the anticancer drug when the level of expression and/or activation detected for the oncogenic fusion protein is not changed (e.g., not substantially decreased) compared to the reference expression and/or activation profile.

In some embodiments, the methods of the present invention may be useful to aid or assist in the identification of a subject having cancer who is resistant to treatment with an anticancer drug or in the determination of whether a subject having cancer is resistant to treatment with an anticancer drug, wherein the subject has a cancer such as, e.g., a hematological malignancy. In other embodiments, the methods of the present invention may be useful for improving the identification of a subject having cancer who is resistant to treatment with an anticancer drug or the determination of whether a subject having cancer is resistant to treatment with an anticancer drug, wherein the subject has a cancer such as, e.g., a hematological malignancy.

In certain embodiments, the method further or alternatively comprises the step of indicating that the subject is sensitive to treatment with the anticancer drug when the level of expression and/or activation (e.g., phosphorylation) detected for the oncogenic fusion protein is changed (e.g., substantially decreased) compared to the reference expression or activation profile. Non-limiting examples of reasons why a subject having cancer would be resistant to treatment with an anticancer drug include the presence of one or more mutations in the oncogenic fusion protein of interest (e.g., BCR-ABL), non-compliance with the therapeutic regimen, and/or administration of a suboptimal drug dose. With regard to a suboptimal drug dose of the anticancer drug, the method can further comprise the step of increasing the next or subsequent dose of the anticancer drug administered to the subject. In further embodiments, one or more signal transduction molecules present in the cellular extract are detected in addition to one or more oncogenic fusion proteins, and the subject is identified as resistant or sensitive to treatment based on this "molecular profile."

V. Oncogenic Fusion Proteins

In particular embodiments, expression/activation profiling of one or more oncogenic fusion proteins, alone or in combination with expression/activation profiling of substrates thereof and/or other signal transduction pathway proteins can be performed on cell lysates prepared using the apparatuses and methods of the present invention, e.g., to determine the efficacy of tyrosine kinase inhibitor therapy for patients in need thereof (e.g., patients with a BCR-ABL mediated disease such as chronic myelogenous leukemia). The oncogenic fusion proteins and other analytes are advantageously interrogated in cell lysates prepared by the apparatuses and methods of the invention without changing the intracellular concentration of the tyrosine kinases inhibitor.

In certain embodiments, translocations in human tumors that cause the formation of oncogenic fusion proteins and their associated neoplasms include, but are not limited to, the following:

Chronic myelogenous leukemia (CML): Philadelphia chromosome is a translocation which results in BCR/ABL (kinase).

Acute lymphoblastic leukemia (ALL): Chimeric oncogenic proteins include:

| Cytogenetic translocation | Molecular genetic abnormality | % |
| --- | --- | --- |
| cryptic t(12; 21) | TEL/AML1 (kinase) | 25.4% |
| t(1; 19)(q23; p13) | E2A/PBX (PBX1) | 4.8% |
| t(9; 22)(q34; q11) | BCR/ABL fusion (P185) | 1.6% |
| t(4; 11)(q21; q23) | MLL/AF4 fusion | 1.6% |
| t(8; 14)(q24; q32) | IGH/MYC fusion | |
| t(11; 14)(p13; q11) | TCR/RBTN2 fusion | |

Burkitt's lymphoma: c-myc gene translocation t(8;14) (q24;q32). The most common chimeric oncoprotein is c-myc/IGH.

AML: translocation of a part of chromosome 8 to chromosome 21 The resulting chimeric oncoprotein is RUNX1/ETO. Another translocation t(12;15)(p13;q25) results in the TEL/TrkC (kinase) chimeric oncoprotein.

Ewing sarcoma: translocation between chromosomes 11 and 22. The resulting chimeric oncoprotein is EWS/FLI (transcription factor).

DFSP: Over 95% of DFSP tumors have the chromosomal translocation t(17;22), which results in the chimeric oncoprotein COL1A1/PDGF (binds and activates PDGFR).

Acute promyelocytic leukemia: a translocation denoted as t(15;17)(q22;q12). The resulting chimeric oncoprotein is RARα/PML (transcription complex protein).

Pro-B-cell acute lymphoblastic leukemia: translocation t(17;19), which results in the chimeric oncoprotein E2A/HLF (apoptosis inhibitor).

Acute pre-B-cell leukemia: translocation t(1;19). The chimeric oncoprotein is E2A/Pbx1 (kinase substrate).

Rhabdomyosarcoma: translocation of t(2:13)(q35;q14), which results in the chimeric oncoprotein PAX3/FKHR (transcription factor).

A soft tissue malignancy of very young children: t(12; 15)(p13;q25) rearrangement which results in the following chimeric oncoprotein: protein tyrosine kinase ETV6/NTRK3 (kinase).

Papillary thyroid carcinoma: the chimeric oncoprotein is RET/PTC (kinase).

Prostate cancer: the chimeric oncoprotein is TMRSS/ERG (kinase).

Additional examples of translocations in human tumors that cause the formation of oncogenic fusion proteins and their associated neoplasms:

| Oncogene | Neoplasm |
| --- | --- |
| bcr/abl | chronic myelogenous leukemia; acute lymphocytic leukemia |
| dek/can | acute myeloid leukemia |
| E2A/pbx1 | acute pre-B-cell leukemia |
| PML/RAR | acute promyelocytic leukemia |
| ?/erg | myeloid leukemia |
| irel/urg | B-cell lymphoma |
| CBFβ/MYH11 | acute myeloid leukemia |
| aml1/mtg8 | acute myeloid leukemia |
| ews/fli | Ewing sarcoma |
| lyt-10/Cα1 | B-cell lymphoma |
| hrx/enl | acute leukemias |
| hrx/af4 | acute leukemias |
| NPM/ALK | large-cell lymphomas |

Adapted from G. M. Cooper, Oncogenes, 2nd ed. Boston and London: Jones and Bartlett, 1995.

VI. Examples

The following examples are offered to illustrate, but not to limit, the claimed invention.

Example 1

Exemplary Cell Isolation Apparatuses

This example describes exemplary cell isolation apparatuses for the separation of leukocytes from patient whole blood using a filtration method. Embodiments and aspects of a cell isolation apparatus of the present invention are depicted in FIG. 2-6.

The cell isolation apparatus of the present invention is used to separate red blood cells from other cells present in whole blood. In particular, leukocytes and/or circulating tumor cells are separated from significant numbers of red blood cells and plasma present in whole blood. The cell isolation apparatus of the present invention comprises a filtration device and a collection vessel. The filtration device is an assembly comprising an upper chamber, a lower chamber and one or more (e.g., a plurality of two, three, four, five, six, seven, eight, nine, ten, or more) stacked filter membranes between the upper and lower chambers. The upper and lower chambers can be manufactured from materials such as, but not limited to, polypropylene and polystyrene. In certain embodiments, the filter membrane has a pore size of 8 μm and a thickness of 355.6-558.8 μm, and has a leukocyte retention yield of 70-80%. A non-limiting example of a filter membrane includes White Blood Cell Isolation (Leukosorb) Medium (PALL Cat. No. BSP0669).

Typically, 1 ml of patient blood treated with protease inhibitors and phosphatase inhibitors is loaded into the upper chamber of the cell isolation apparatus. The unit is centrifuged for 5-30 minutes at 600-2000 rpms (e.g., 800 rpms) at 4° C. in a tabletop centrifuge such as an Allegra 6R centrifuge (Beckman), Sorvall Legend centrifuge (Thermo Scientific), or Heraeus Megafuge centrifuge (Kendro). In certain instances, the first collection vessel containing the red blood cells is removed from the cell isolation apparatus and a second collection vessel is attached. Without washing steps, 200 μl-1 ml of lysis buffer is added to the upper chamber of the filtration device. The upper chamber is capped and the filtration device and second collection vessel are shaken vigorously for 15-30 minutes at 4° C. The filtration device and second collection vessel are placed in a centrifuge and spun at about 3,000 rpm for about 5 minutes. The cell lysate can be transferred to another vessel for storage at −70° C.

In other instances, the first collection vessel containing the red blood cells is removed from the cell isolation apparatus and the filtration device containing the filter membranes is disassembled. The upper chamber and the lower chamber are unscrewed to separate them. Using forceps, the filter membranes containing the separated leukocytes are placed in a second collection vessel containing lysis buffer. Non-limiting examples of a second collection vessel include 1.5 ml and 2 ml microcentrifuge tubes. In some instances, the second collection vessel is further incubated at 4° C. for at least 1, 5, 10, 15, 20, 30, 60, or 120 minutes, preferably between about 15 to about 30 minutes. In other instances, the second collection vessel is placed on ice and briefly vortexed for 10 seconds every 10 minutes for a total of 30 minutes. In some embodiments, the cell lysate is stored at −70° C. In other embodiments, the vessel containing the lysate is centrifuged to remove the filter membranes and cell fragments. The supernatant of the cell lysate is transferred to another tube for storage at −70° C.

Figure 26:
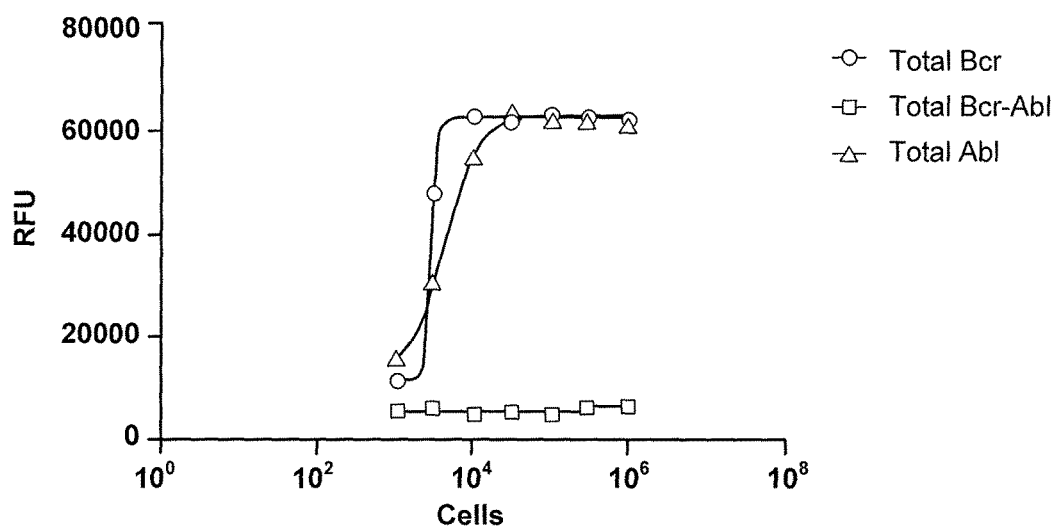
FIG. 26 illustrates the expression level of BCR-ABL, BCR and ABL in a blood sample from a normal, healthy subject.

In yet another embodiment, the cell isolation apparatus comprises a tube filter unit and a collection vessel (FIG. 26). The tube filter unit comprises a cylindrical tube affixed at one end with one or more (e.g., a plurality of two, three, four, five, six, seven, eight, nine, ten, or more) filter membranes, wherein the membranes are able to retain healthy and malignant leukocytes and/or circulating tumor cells from whole blood samples. In particular instances, the filter membranes are (e.g., 2, 3, or 4) layers of filters such as PALL filters (e.g., Leukosorb Medium). In certain instances, each filter has a pore size of 8 µm, a thickness of 355.6-558.8 µm, and a leukocyte retention yield of 70-80%. In certain instances, the tube filter unit is attached to a collection vessel by way of a plastic adapter. The filter membrane of the tube filter unit is securely attached to the adapter which is positioned in the opening of a collection tube. Examples of collection vessels include, but are not limited to, 3 ml, 5 ml, 8 ml, 14 ml and 16 ml plastic culture tubes. In certain embodiments, 1 ml of patient whole blood treated with protease inhibitors and phosphatase inhibitors is loaded into the top of the tube filter unit of the cell isolation apparatus. The apparatus is centrifuged for 5-30 minutes at 600-2000 rpms (e.g., 800 rpms) at 4° C. in a tabletop centrifuge such as an Allegra 6R centrifuge (Beckman), Sorvall Legend centrifuge (Thermo Scientific), or Heraeus Megafuge centrifuge (Kendro). In certain instances, the collection tube containing the red blood cells is removed from the cell isolation apparatus and a new collection tube is attached. Without washing steps, 200 µl-1 ml of lysis buffer is added to the opening of the tube filter unit of the cell isolation apparatus. The apparatus is sealed or capped, and then shaken vigorously for 15-30 minutes at 4° C. The cell isolation apparatus is centrifuged and spun at about 3000 rpm for about 5 minutes in a tabletop centrifuge. The cell lysate can then be transferred from the collection vessel to another vessel for storage at −70° C.

In still yet another embodiment, the cell isolation apparatus of the present invention comprises a plurality of filtration devices or tube filter units and a multi-well or multi-tube collection vessel. Filtration devices and tube filter units described above can be attached to wells of a multi-format plate, such as a 12-well, 24-well, 48-well, or 96-well plate.

Example 2

Protocol for Tumor Cell Isolation from CML Patient Blood by Filtration Method Using Cell Isolation Apparatus This example details the protocol used to isolate and harvest CML tumor cells in individual patient whole blood using a method of the present invention. The whole blood from patient can be in vitro treated or non-treated with BCR-ABL inhibitors prior to isolation.

Freshly drawn blood sample are best for isolation of tumor cells. If fresh samples cannot be obtained, blood samples can be processed within 1-3 days after being drawn. Samples collected in EDTA (Becton Dickenson cat. no. #366643, EDTA (K2) sterile tubes) are sent to for processing the day they are drawn. Samples must be kept at room temperature prior to processing. It is important to avoid refrigerating or freezing the samples at this point.

The blood sample received in EDTA tubes (BD #366643) is treated with protease and phosphatase inhibitors. The tube of blood is mixed gently by slowly inverting 4-6 times, and then 0.05 mL of a protease and phosphatase inhibitor cocktail per 1 mL blood is added. At this point in the protocol, tumor and white blood cells can be isolated from the blood sample by proceeding to the section of this example entitled "Isolation and lysis of tumor and white blood cells". Optionally, the blood sample can be treated with a drug prior to proceeding to that section.

Drug Treatment of Patient Blood Samples

The drug such as a BCR-ABL inhibitor are diluted in Hank's Balanced Saline Solution (HBSS) before it is added to the blood sample. 1.0 mL of the patient's blood sample is placed into a culture tube. The desired concentration of drug is added to each aliquot of the patient's blood. For instance, 10 µl, 1 µl or 0.1 µl that correspond to a drug concentration of 10 µM, 1 µM or 0.1 µM is added to a tube. One milliliter (1 ml) of untreated blood in a separate tube can be used as a control. The tubes are then incubated for 4 hours at 37° C. in a $CO_2$ incubator. Afterwards, the drug treated sample can be further processed according to the procedure of the next section in order to isolate and lyse the tumor and white blood cells of the sample.

Isolation and Lysis of Tumor and White Blood Cells

Gently mix the blood sample to be added to the filtration device by slowly inverting the tube 4-6 times. Using a 1 ml pipette, load 1 mL of the blood sample to the upper chamber of the filtration device that is housed in a collection tube. After the sample has been loaded, snap close the filtration device. The cell isolation apparatus is place in an Allegra 6R centrifuge and centrifuged for 15 minutes at 1,000 rpms at 4° C. After centrifugation, the cell isolation apparatus is removed from the centrifuge. The first collection tube that contains the red blood cells is removed from the filtration unit and replaced with a second, clean collection tube. The first collection tube containing blood is capped for safety and kept at room temperature for later use.

200 µL of lysis buffer (kept on ice) is added to the upper chamber of the filtration device containing the membrane with the white blood cells, and then the unit is snapped closed. The cell isolation apparatus is placed on a shaking (rotating) platform that is kept at 4° C. The shaking platform along with the cell isolation apparatus undergoes three cycles comprising of shaking for 2 minutes and then resting 5 minutes per cycle. Next, the cell isolation apparatus is centrifuged at 2,000 rpm for 10 minutes at 4° C. The cell lysate located in the second collection tube is transferred to a 2 mL centrifugation tube with a 1 mL pipette for use in CEER immunoassays such as the BCR-ABL assay and other pathway marker assay. optionally, the cell lysate is stored at −70° C.

Example 3

Leukocyte Isolation and Harvesting by Filtration Method from Whole Blood without Dilution of Anticancer Drug The example illustrates a protocol for the isolation and lysis of leukocytes from patient whole blood using a filtration method. In addition to normal, healthy leukocytes, malignant leukocytes such as chronic myelogenous leukemia (CML) tumor cells from whole blood can be isolated without diluting drug concentrations and without interfering quantities of contaminating red blood cells. In certain embodiments, whole blood from a patient can be in vitro treated or non-treated with one or more tyrosine kinase inhibitors (e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof) prior to isolation. Chronic myelogenous leukemia is a cancer of the white blood cells. It is a form of leukemia characterized by the increased and unregulated growth of predominantly myeloid cells in the bone marrow and the accumulation of these cells in the blood. Therefore, determining the level of oncogenic markers in CML tumors in patients by extracting tumor cells along with leukocytes away from significant numbers of red blood cells and plasma in the blood becomes critical for diagnostic and prognostic evaluations. This example describes a filtration method that enables the recovery of leukocytes and/or circulating tumor cells from patient blood without dilution of anticancer drug.

Typically, patient blood is drawn into blood collection tubes containing EDTA or other anticoagulants and mixed gently by inversion. The blood sample is stored at room temperature and processed within 24-72 hours, and is typically not refrigerated or frozen. The tube containing the whole blood is mixed by gentle inversion up and down and treated with a solution mixture comprising protease inhibitors and phosphatase inhibitors. The solution mixture can comprise sodium orthovanadate (200 mM, at a final concentration of 2 mM), Sigma Protease Inhibitor (50×; at a final concentration of 1×), and Halt Phosphatase Inhibitor (100×; at a final concentration of 2×) and is admixed with the patient's blood sample. Examples of protease inhibitors and phosphatase inhibitors include, but are not limited to, Halt Protease and Phosphatase Inhibitor Cocktail (Therma Scientific); complete ULTRA and PhosSTOP (Roche Applied Science); Protease Inhibitor Set (EMD Chemicals); and Phosphatase Inhibitor Cocktail Set I-IV (EMD Chemicals).

A cell isolation apparatus is used to separate the red blood cells from other cells such as leukocytes and/or circulating tumor cells in patient blood sample. The cell isolation apparatus comprises a filtration device and a collection vessel as illustrated. In certain aspects, the filtration device is assembled by inserting one or more (e.g., a plurality of two, three, four, five, six, seven, eight, nine, ten, or more) leukocyte-retaining filter membranes between the upper chamber and the lower chamber of the filtration device. The filter membrane can have a pore size of 8 µm, a thickness of 355.6-558.8 µm, and a leukocyte retention yield of 70-80%. A non-limiting example of a filter membrane includes White Blood Cell Isolation (Leukosorb) Medium (PALL Cat. No. BSP0669). The assembled filtration device is placed on top of a collection vessel. The cell isolation apparatus is uncapped before the blood sample is loaded into it. Examples of collection vessels include, but are not limited to, tubes such as plastic culture tubes having a capacity of 3 ml, 5 ml, 8 ml, 14 ml, or 16 ml.

An exemplary method of isolating and lysing leukocytes and/or circulating tumor cells from a patient's blood sample includes the following steps. 1 ml of blood sample pretreated with protease inhibitors and phosphatase inhibitors is gently mixed by inversion. Next, 1 ml of the blood sample is loaded into the upper chamber of the cell isolation apparatus as assembled as described above. The cell isolation apparatus is placed into a clinical or tabletop centrifuge, such as an Allegra 6R centrifuge (Beckman), Sorvall Legend centrifuge (Thermo Scientific), or Heraeus Megafuge centrifuge (Kendro). Typically, the cells are centrifuged for 5-30 minutes at 600-2,000 rpms (e.g., 800 rpms) at 4° C. Adaptors can be used during centrifugation to secure the cell isolation apparatus into the centrifuge rotor. After centrifugation, the cell isolation apparatus is removed from the centrifuge and the filtration device is separated from the collection vessel which contains red blood cells that have passed through the filtration device. The collection vessel with the red blood cells can be capped for biosafety and set aside.

In certain embodiments, a new collection vessel, such as, but not limited to, another collection tube or a microcentrifuge tube is placed under the filtration device. Without the addition of wash steps, 200 µl-1 ml of lysis buffer is added to the upper chamber of the filtration device. The upper chamber is capped and the filtration device and new collection vessel are shaken vigorously for 15-30 minutes at 4° C. The filtration device and new collection vessel are placed in a centrifuge such as a microcentrifuge and spun at about 3,000 rpm for about 5 minutes. The cell lysate can be transferred to another centrifuge vessel such as a microcentrifuge tube for storage at −70° C.

In another embodiment, after the cell isolation apparatus is removed from the centrifuge and the filtration device is separated from the collection tube containing the red blood cells, the one or a plurality of filter membranes between the upper and lower chambers of the filtration device are isolated. The upper and lower chambers are detached (e.g., unscrewed) and the filter membranes are isolated using forceps. The membranes are placed into a new collection vessel, such as a 1.5 ml or 2.0 ml microcentrifuge tube, containing 1 ml of cell lysis buffer. To lyse the cells on the filter membranes, the new collection vessel is vortexed immediately. The vessel is then placed on ice and briefly vortexed for 10 seconds every 10 minutes for a total of 30 minutes. The cell lysate is then transferred into another vessel, such as a 1.5 ml or 2.0 ml microcentrifuge tube and stored at −70° C.

Example 4

Isolation of Cells by Filtration Method Using a 96-Well Cell Isolation Apparatus This example demonstrates the recovery of isolated cells from a sample such as, for example, whole blood, serum, plasma, urine, sputum, bronchial lavage fluid, tears, nipple aspirate, lymph, saliva, and/or fine needle aspirate (FNA) using a filtration method or a filtration method in conjunction with magnetic bead capture, wherein the isolated cells can be used in the present invention to detect the activation state and/or total amount of one or a plurality of oncogenic fusion proteins (e.g., BCR-ABL) and/or signal transduction molecules (e.g., EGFR, HER-2, HER-3, HER-4, VEGFR-1, VEGFR-2, VEGFR-3, PDGFR, c-Met, c-KIT, IGF-IR, SHC, PI3K, etc.). In particular, this example demonstrates the recovery of K562 cells (i.e., cells from a human chronic myelogenous leukemia cell line) from blood spiked with K562 cells using a filtration method alone or a filtration method after magnetic bead capture with anti-CD45 antibodies, followed by the preparation of a K562 cell lysate and determination of the expression and/or activation status of one or more oncogenic fusion proteins (e.g., BCR-ABL), substrates thereof, pathways thereof, or combinations thereof. This example also demonstrates the recovery of a subset of blood cells (i.e., leukocytes) from patient blood samples using either a filtration method or a filtration method prior to magnetic bead capture with anti-CD45 antibodies, followed by the preparation of a cell lysate and determination of the expression and/or activation status of one or more oncogenic fusion proteins (e.g., BCR-ABL), substrates thereof, pathways thereof, or combinations thereof. By eliminating the need for any wash steps after patient sample collection and cell isolation, the methods described herein are advantageous because cells of interest can be recovered from blood without changing the intracellular concentration of an anticancer drug such as a tyrosine kinase inhibitor. Contrary to the art, the methods described in this example provide cell lysates from recovered cells without substantial dilution of an anticancer drug such as a tyrosine kinase inhibitor (e.g., Gleevec®, Tasigna®, Sprycel®, etc.).

A 96-well cell isolation plate can be prepared to isolate leukocytes and/or K562 cells from fresh collected blood. First, the original membrane from a 96-well filtration plate can be removed and replaced with filter membranes (e.g., LeukoLOCK (Life Technologies), Acroprep (PALL) and Leukosorb (PALL)). In these embodiments, fresh collected blood with or without spiked K562 cells can be loaded into wells of a 96-well cell isolation plate. A second 96-well microplate can serve as a blood waste collection plate and should be placed under the cell isolation plate with filter membranes. The plate assembly can be centrifuged at room temperature for about 5 min at a speed ranging from about 600 rpm to 3,000 rpm, such as e.g., about 600 rpm, 1,000 rpm, 2,000 rpm, and 3,000 rpm. After centrifugation, the filter membrane can be transferred to a centrifugation tube and the cells on the filter membrane can be treated with a volume of lysis buffer (e.g., 300 µl of lysis buffer) and vortexed briefly and immediately in order to lyse the cells. The centrifugation tube containing the cell lysate can be placed on ice for about 30 min and subjected to brief vortexing about every 10 minutes. The tube can be centrifuged for about 15 minutes to separate the cellular debris from the supernatant. The supernatant containing the lysate can be collected and analyzed by microarray such as a proximity-mediated immunoassay to detect oncogenic fusion proteins (e.g., BCR-ABL) and/or signal transduction molecules (e.g., EGFR, HER-2, HER-3, HER-4, VEGFR-1, VEGFR-2, VEGFR-3, PDGFR, c-Met, c-KIT, IGF-IR, SHC, PI3K, etc.).

The fresh collected blood with or without spiked K562 cells can undergo the filtration method for cell isolation described herein after initial processing by magnetic bead capture with anti-CD45 antibodies. Fresh collected blood with or without spiked K562 cells can be incubated with washed magnetic beads coupled with anti-CD45 antibodies (e.g., CD45 Dynalbeads (Invitrogen)). Washed magnetic beads can be prepared according to the manufacturer's instructions. For example, the procedure may include the following steps: 1) transfer 100 µl of magnetic beads coupled to anti-CD45 antibodies to a 1.5 ml centrifuge tube; 2) add 1 ml of buffer and mix gently; 3) place the centrifuge tube on the magnet for 1 min; 4) remove supernatant; and 5) remove the tube from the magnet and resuspend the magnetic beads in 100 µl of buffer. In particular instances, 100 µl of the washed beads can be added to each of the K562 spiked blood samples. The samples can then be incubated on a rotator in a cold room at 4° C. or at room temperature for about 20 mins to 2 hours. The incubation time may be, e.g., at least 20 minutes, 30 minutes, 1 hour, 1.5 hours or 2 hours. Next, the samples can be placed on the magnet (e.g., DynaMag magnet). The supernatant can be collected and loaded into the wells of a 96-well cell isolation plate. The method for cell isolation by filtration can be performed as described above.

A subset of blood cells (e.g., leukocytes) can be isolated from fresh collected CML patient blood samples by the filtration method described herein. In particular instances, blood samples can be collected from CML patients taking tyrosine kinase inhibitors (e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), and combinations thereof). An advantage of the present invention is that the blood samples from patients, including those from patients receiving tyrosine kinase therapy, do not require additional washing or processing. Similarly as described above, a 96-well cell isolation plate can be prepared by removing the original membrane from a 96-well filtration plate and replacing it with a membrane filter (e.g., LeukoLOCK (Life Technologies) or Acroprep (PALL)) able to capture blood cells of interest (e.g., leukocytes). Fresh collected blood from a CML patient can be loaded into wells of a 96-well cell isolation plate, and a second 96-well microplate can be placed under the cell isolation plate with filter membranes. The plate assembly can be centrifuged at room temperature for about 5 min at a speed ranging from about 600 rpm to 3,000 rpm, such as, e.g., about 600 rpm, 1,000 rpm, 2,000 rpm, and 3,000 rpm. After centrifugation, the filter membrane can be transferred to a centrifugation tube. To lyse the cells, about 300 µl of lysis buffer can be added to the tube and then the tube can be vortexed briefly. The tube containing the cell lysate can be placed on ice for about 30 min and subjected to brief vortexing about every 10 minutes. The tube can be centrifuged for about 15 minutes to separate the cellular material from the supernatant. The supernatant containing the lysate can be collected and analyzed by a microarray assay such as a proximity-mediated immunoassay described herein.

Fresh collected blood from a CML patient can be initially processed by magnetic bead capture with anti-CD45 antibodies prior to the filtration method for cell isolation described herein. In certain embodiments, washed magnetic beads coupled with anti-CD45 antibodies (e.g., CD45 Dynalbeads (Invitrogen)) can be incubated with blood collected from CML patients. Washed magnetic beads can be prepared according to the manufacturer's instructions, for example, the procedure may include the following steps: 1) transfer 100 µl of magnetic beads coupled to anti-CD45 antibodies to a 1.5 ml centrifuge tube; 2) Add 1 ml of buffer and mix gently; 3) place the centrifuge tube on the magnet for 1 min; 4) remove supernatant; and 5) remove the tube from the magnet and resuspend the magnetic beads in 100 μl of buffer. In particular instances, 1000 of the washed beads can be added to each of the K562 spiked blood samples. The samples can then be incubated on a rotator in a cold room at 4° C. or at room temperature for about 20 mins to 2 hours. The incubation time may be, e.g., at least 20 minutes, 30 minutes, 1 hour, 1.5 hours or 2 hours. Next, the samples can be placed on the magnet. The supernatant can be collected and loaded into the wells of a 96-well cell isolation plate. The method for cell isolation by filtration can be performed as described above.

Figure 7A:
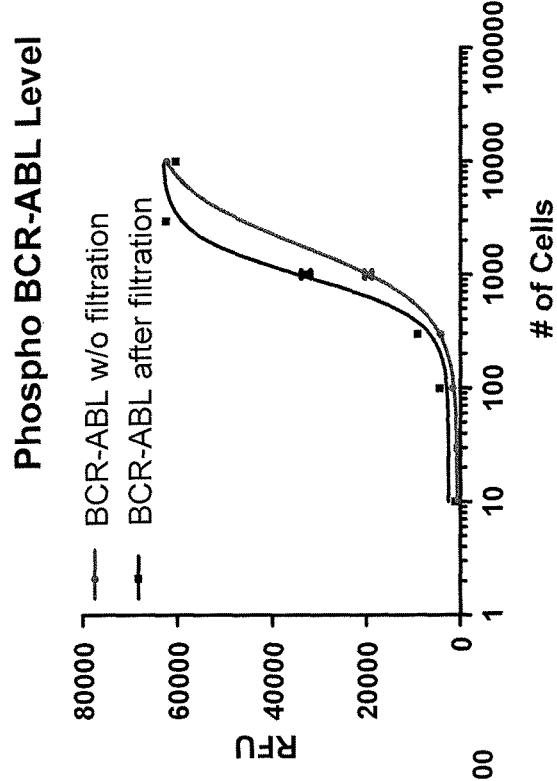
FIG. 7A-B illustrate that both total and phosphorylated BCR-ABL can be detected and measured in cell lysates prepared from K562 cells by filtration. The levels of total BCR-ABL in cells following filtration are similar to levels observed in unfiltered samples. Additionally.
Figure 7B:
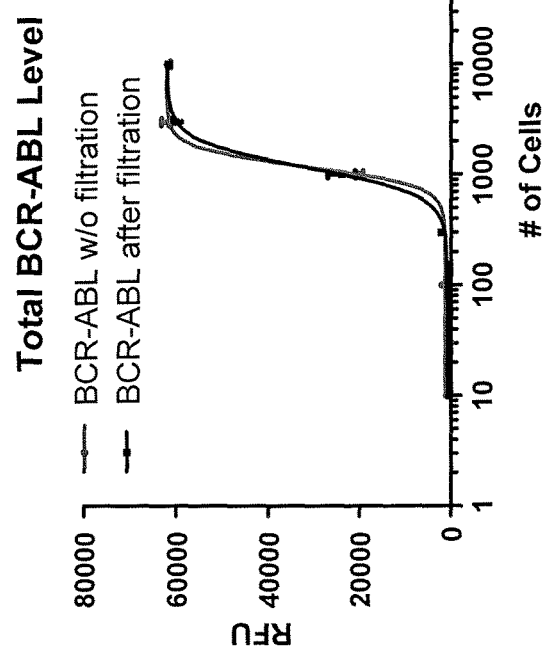

FIG. 7 illustrates that both total and phosphorylated BCR-ABL can be detected and measured in cell lysates prepared from K562 cells isolated from blood samples spiked with K562 cells and by using the leukocyte filtration method of the present invention. FIG. 7A shows that the levels of total BCR-ABL in cells following filtration were similar to levels observed in unfiltered samples. Additionally, FIG. 7B shows that the levels of phosphorylated BCR-ABL in K562 cells after filtration were comparable to the levels detected in unprocessed cells.

Figure 8A:
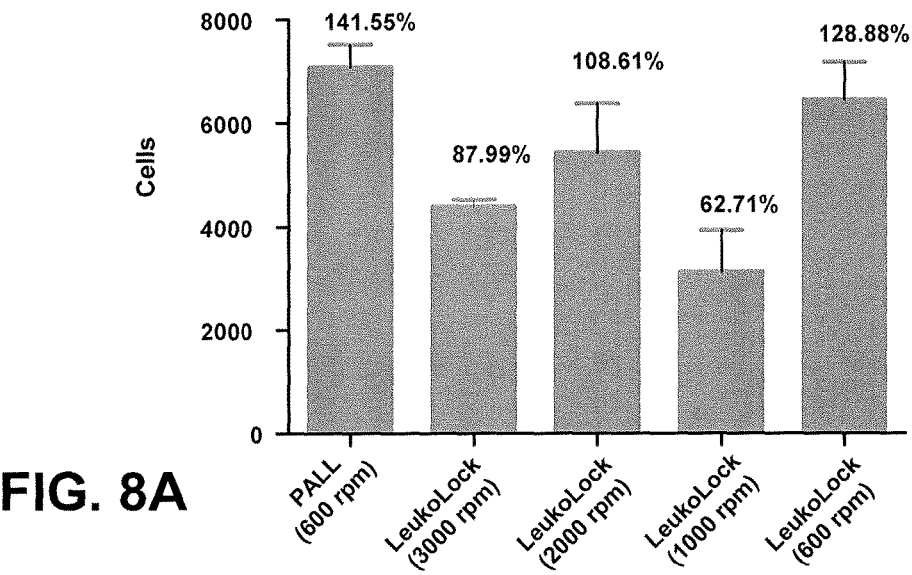
FIG. 8A-B illustrates that both total (FIG. 8A) and phosphorylated BCR-ABL levels (FIG. 8B) can be detected and measured in cell lysates, wherein the cell lysates are prepared from blood samples spiked with K562 cells, filtered through filtration membranes, and analyzed by microarray such as the proximity-mediated immunoassay described herein.
Figure 8B:
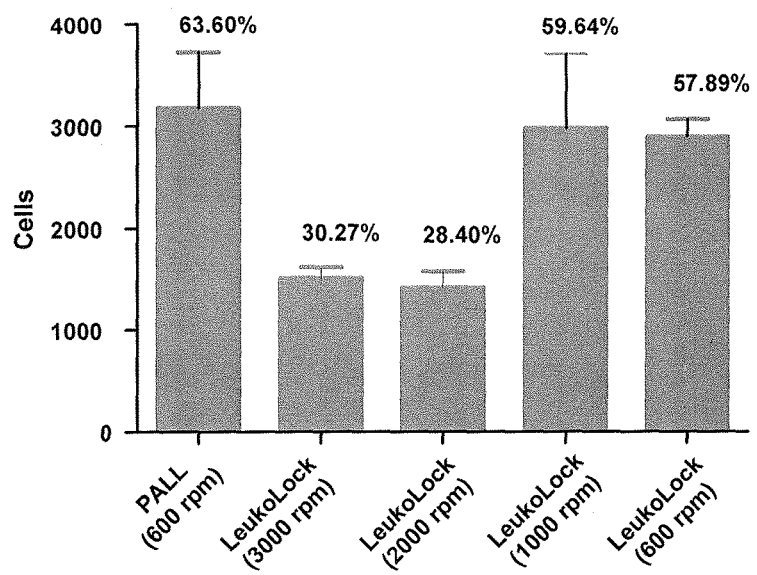

FIG. 8A-B illustrate that both total and phosphorylated BCR-ABL levels were detected and measured in cell lysates, wherein the cell lysates were prepared from blood samples spiked with K562 cells, filtered through filtration membranes, and analyzed by microarray such as a proximity assay such as a Collaborative Proximity Immunoassay (CO-PIA) described in PCT Application No. PCT/US2010/042182, filed Jul. 15, 2010, and US Patent Publication Nos. 20080261829, 20090035792, and 20100167945, the disclosures of which are herein incorporated by reference in their entirety for all purposes. In particular, 5,000 cells isolated by the methods described herein were used in a BCR-ABL CEER assay. The percentage recovery of total and phosphorylated BCR-ABL in different samples that were centrifuged at various speeds was compared. FIG. 8A shows that there was a 141.55% recovery of total BCR-ABL signal in isolated K562 cells following the cell isolation method of the present invention that includes a filtration apparatus with PALL filter membranes and a centrifugation step at a speed of 600 rpm. In comparison, when the cell isolation method included LeukoLock filter membranes and a centrifugation step at a speed of 600 rpm, the total BCR-ABL signal recovery was 128.88%. Notably, the percentage recovery decreased to 62.71% when the centrifugation speed was increased to 1,000 rpm. FIG. 8B shows the percentage recovery of phosphorylated BCR-ABL signal in cells isolated from 1 ml blood samples spiked with K562 cells and by using the methods of the present invention. 63.60% of the phosphorylated BCR-ABL signal was detected in K562 cells isolated using the filtration method that included isolating cells with the PALL filtration membrane and centrifuging the filtration apparatus at 600 rpm. 59.64% of the phosphorylated BCR-ABL signal was detected in K562 cells isolated using the filtration method that included isolating cells with the LeukoLOCK filtration membrane and centrifuging the filtration apparatus at 1,000 rpm. When the centrifugation speed was decreased to 600 rpm, the percentage recovery decreased to 57.89% with the LeukoLock membrane.

Figure 9A:
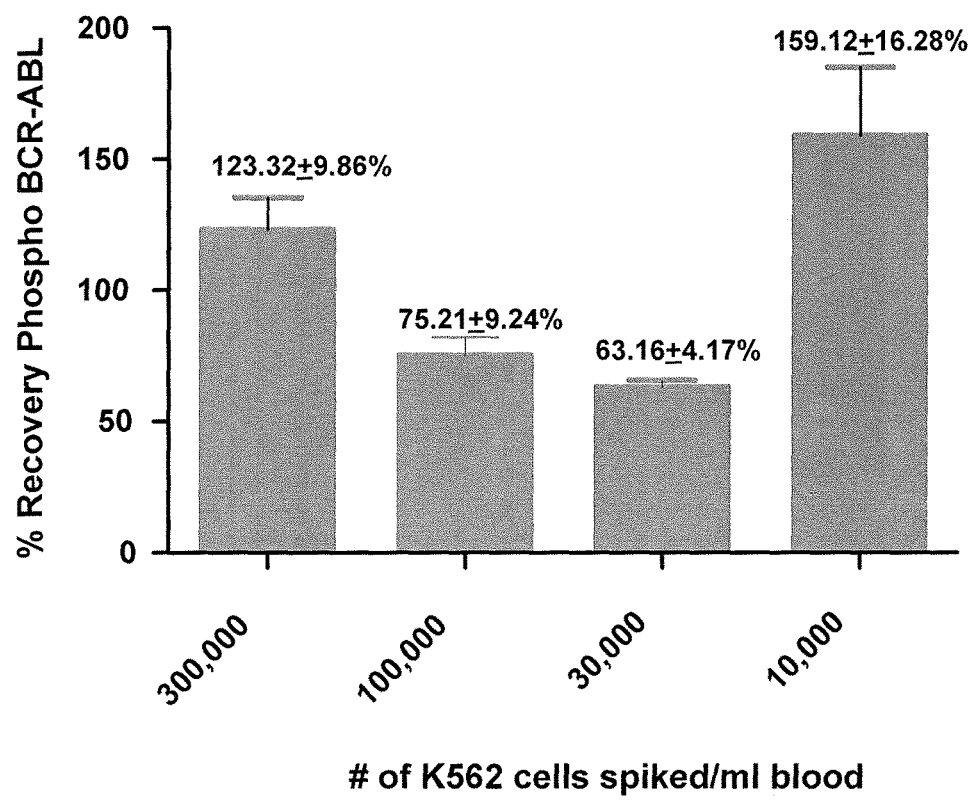
FIG. 9A-B illustrates that phosphorylated BCR-ABL levels (A) can be detected and measured in cell lysates prepared from blood samples spiked with varying amounts of K562 cells, filtered through filtration membranes, and analyzed by microarray such as the proximity-mediated immunoassay described herein. The methods of the present invention can be used to detect the levels of phospho-BCR-ABL in samples spiked with K562 cells. In particular, the measured levels of phosphorylated BCR-ABL relate to the number of K562 cells added to the blood samples.

FIG. 9A illustrates that phosphorylated BCR-ABL levels were detected and measured in cell lysates prepared from blood samples spiked with varying amounts of K562 cells, filtered through filtration membranes, and analyzed by microarray such as the proximity-mediated immunoassay described herein. The methods of the present invention used to detect the levels of phospho-BCR-ABL in samples spiked with K562 cells. In particular, the measured levels of phosphorylated BCR-ABL relate to the number of K562 cells added to the blood samples. The percentage recovery of the phosphorylated BCR-ABL signal was 123.32% for the sample spiked with 300,000 K562 cells, 75.21% for the sample spiked with 100,000 K562 cells, 63.16% for the sample spiked with 30,000 K562 cells, and 159.12% for the sample spiked with 10,000 K562 cells.

Figure 9B:
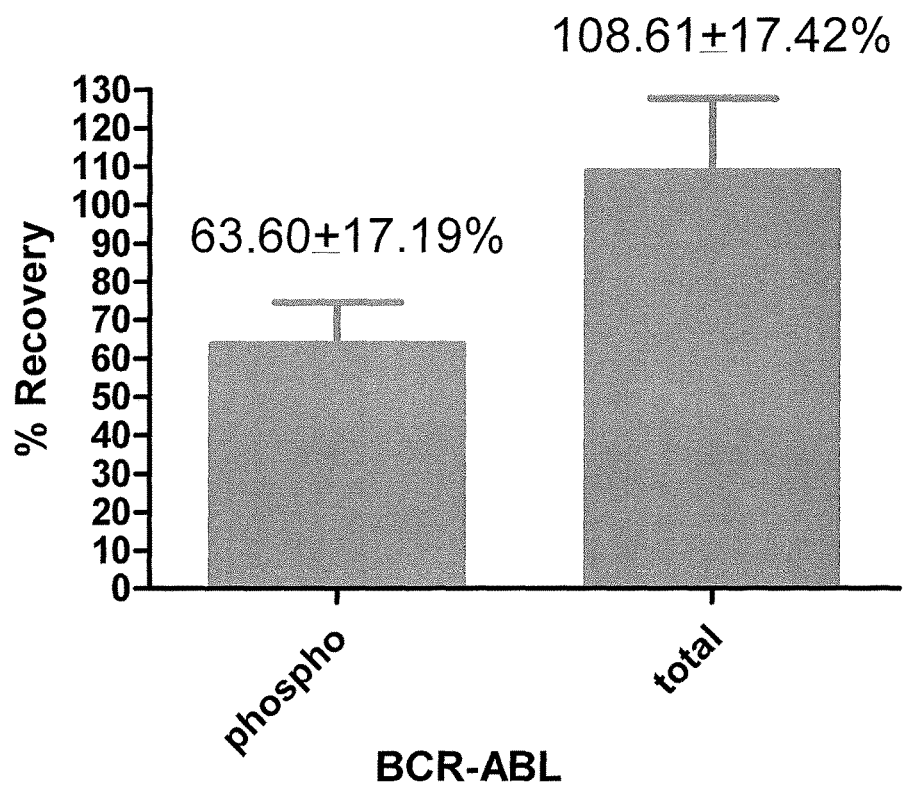

FIG. 9B illustrates the BCR-ABL signal in K562 cells recovered after filtration when the cells are spiked in blood. The percentage recovery of the phosphorylated BCR-ABL signal was 63.60% for the sample spiked with 1,000,000 K562 cells and the total was 108.61%.

Example 5

Protocol for Tumor Cell Isolation from CML Patient Blood by Filtration Method Using 96-Well Cell Isolation Apparatus The example illustrates a protocol for the isolation and harvesting of chronic myelogenous leukemia (CML) tumor cells from patient whole blood using a filtration method. In a preferred embodiment, the whole blood from a patient can be in vitro treated or non-treated with tyrosine kinase inhibitors (e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof) prior to isolation. Chronic myelogenous leukemia is a cancer of the white blood cells. It is a form of leukemia characterized by the increased and unregulated growth of predominantly myeloid cells in the bone marrow and the accumulation of these cells in the blood. 95% of CML cancer cells express BCR-ABL oncoprotein. Therefore, determining the level of BCR-ABL in CML tumors in patients by extracting tumor cells along with white blood cells away from red blood cells in the blood becomes critical. This example describes a filtration method that enables the recovery of tumor cells (e.g. leukocytes and other white blood cells) from patient blood.

Typically, patient blood is drawn into blood collection tubes contain EDTA and mixed gently by inversion. The whole blood sample is stored at room temperature and processed within 24 hours. The filtration plate comprises a 96-well plate with a membrane at the bottom of the well which can allow for the recovery of white blood cells (e.g., leukocytes) from total blood. If a filtration plate is not commercially available, the filtration plate can be prepared through a series of steps such as, but not limited to a) removing the original filter membrane from a Whatman 96-well Unifilter plate; b) removing the LeukoLOCK Total RNA filter membrane from its filter cartridge housing; c) punching a 0.25 inch diameter hole into the LeukoLOCK Total RNA filter membrane so the newly created membrane circles fit into a well of the 96-well filtration plate; and d) gently placing the new LeukoLOCK Total RNA filter membrane circles into the Whatman 96-well Unifilter plate without its original membrane. Next, a 96-well microplate is placed under the 96-well filtration plate and both plates are sealed together with tape to form a filtration plate duet. The 96-well microplate serves to collect the pass-through blood.

The filtration method can include the following steps. A patient blood sample is mixed with a 1 ml pipette by pipetting up and down for 5-10 times. Using a 1 ml pipette, 300 µl of patient blood is loaded into a well of the pre-made 96-well filtration plate duet. The plate duet is centrifuged in a table-top centrifuge (e.g., Allegra 6R (Beckman Coulter)) for 5 minutes at 3,000 rpm at room temperature. After centrifugation, the plate duet is removed from the centrifuge. The tape is removed and the plates of the plate duet are separated. Using 114 mm (4½") dissecting forceps, the LeukoLOCK filter membrane circle is removed from the well of the filtration plate and placed into a 2 ml centrifugation tube containing 300 µl of protein lysis Buffer. Next, the centrifugation tube is vortexed immediately. The centrifugation tube is placed on ice and briefly vortexed for 10 seconds every 10 minutes for a total of 30 minutes. The lysate is transferred into a new 2 ml centrifugation tube using a 1 ml pipette. At this point, the lysate is be stored at −70° C. or used in an assay that detects the activation state and/or total amount of one or a plurality of oncogenic fusion proteins (e.g., BCR-ABL) and/or signal transduction molecules (e.g., EGFR, HER-2, HER-3, HER-4, VEGFR-1, VEGFR-2, VEGFR-3, PDGFR, c-Met, c-KIT, IGF-IR, SHC, PI3K, etc.).

The filtration method can also include the following steps. A patient blood sample is treated with tyrosine kinase inhibitors prior to filtration to recover tumor cells (e.g. leukocytes and other white blood cells) from patient blood. In particular instances, 1.2 ml of fresh collected patient blood is transferred to a culture tube and specific concentration ranges of tyrosine kinase inhibitor drugs are added, such as 10 µM, 1 µM or 0.1 µM Dasatinib; 10 µM, 1 µM or 0.1 µM Imatinib; and 10 µM, 1 µM or 0.1 µM Nilotinib. The blood is incubated for about 1 to 24 hours (e.g., 1, 2, 4, 6, 8, 10, 12, 14, 16, 18, 20, 22, or 24 hours) at 37° C. in a $CO_2$ incubator or at room temperature.

Example 6

Protocol for CEER Immuno-Microarray for Determining Phospho-BCR-ABL, Total BCR-ABL and BCR Levels from Patient 2's Blood Samples from the First and Second Blood Draws This example illustrates a procedure for performing a CEER Immuno-Microarray to detect the expression and activation of BCR-ABL in a patient's blood sample. Leukocytes and circulating tumor cells are isolated according to the methods described herein. The isolated cells are lysed and used in a proximity assay such as a Collaborative Proximity Immunoassay (COPIA) described in PCT Application No. PCT/US2010/042182, filed Jul. 15, 2010, and US Patent Publication Nos. 20080261829, 20090035792, and 20100167945, the disclosures of which are herein incorporated by reference in their entirety for all purposes. In particular embodiments, the protocol includes treating the patient's blood sample with magnetic beads that bind BCR.

Dilution of K562 Cell Lysate for CEER Immuno-Microarray.

Untreated K562 cell lysates were prepared according to the methods of the present invention, such as described in Examples 2 and 3. Serial dilutions of untreated K462 cell lysates in Assay Dilution Buffer were performed according to Table 1. The cell lysates were screened by three CEER slides.

TABLE 1

| Final concentration of cells | Vol. of K562 cells | Vol. of Assay Dilution Buffer | # of cells/ 80 µl |
|---|---|---|---|
| 125 cells/µl | 10 µl (5,617 cells/µl) | 440 µl | 10,000 |
| 37.5 cells/µl | 135 µl (125 cells/µl) | 315 µl | 3,000 |
| 12.5 cells/µl | 135 µl (37.5 cells/µl) | 270 µl | 1,000 |
| 3.75 cells/µl | 135 µl (12.5 cells/µl) | 315 µl | 300 |
| 1.25 cells/µl | 135 µl (3.75 cells/µl) | 270 µl | 100 |
| 0.375 cells/µl | 135 µl (1.25 cells/µl) | 315 µl | 30 |
| 0.125 cells/µl | 135 µl (0.375 cells/µl) | 270 µl | 10 |
| 0 cells/µl | 0 | 450 µl | 0 |

Dilution of Cell Lysate from Patient Blood Sample for CEER Immuno-Microarray.

Cell lysates prepared from patient blood samples were prepared according to the methods of the present invention, such as described in Examples 1, 2 and 10. The procedure of diluting patient cell lysate for use with three CEER slides is illustrated in Table 2.

TABLE 2

| | Vol. of lysate | Vol. of Assay Dilution Buffer | Vol. to remove after dilution f |
|---|---|---|---|
| 1:2.5 dilution of lysate | 160 µl pooled patient cell lysate | 240 µl | 150 µl (incubate with 150 µl of beads; 1:5) |
| 1:5 dilution of lysate | 150 µl of 1:2.5 dilution | 150 µl | |
| 1:10 dilution of lysate | 75 µl of 1:2.5 dilution | 225 µl | 150 µl (incubate with 150 µl of beads; 1:20) |
| 1:20 dilution of lysate | 150 µl of 1:10 dilution | 150 µl | |

Procedure for CEER Immuno-Microarray.
1. Blocking slide:
    1.1. Rinse the slide 2× with TBST.
    1.2. Block the slide with 80 µl of protein-free (TBS) Blocking Buffer for 1 hr.
    1.3. Wash 2× with TBST, after blocking step.
    1.4. Add 10 µl of 1 mM $Na_3VO_4$ per ml of Assay Dilution Buffer (2% BSA/0.1% triton/10 mM EDTA/TBS).
2. Incubation with cell lysate:
    2.1. Perform serial dilution of cell lysate with Assay Dilution Buffer as described in Tables ## and ##.
    2.2. Remove an aliquot of the cell lysate for incubation with beads and add an equivalent volume of Assay Dilution Buffer to the aliquots of lysate that will not be incubated with magnetic beads (e.g., BCR-1684 beads).
    2.3. Add 80 µl of cell lysate to the slide and seal the slide.
    2.4. Incubate overnight at room temperature.
    2.5. Wash the slide 5× such that the first wash is a quick rinse with 1.25 ml TBST and the remaining washes are for 3 minutes each.
3. Incubation with detection antibody:
    3.1. Dilute the labeled antibodies to the appropriate concentrations in Assay Dilution Buffer.
        3.1.1 4G10-HRP:dilute 1:320 (Millipore #05-777)
        3.1.2 BCR-GO-AF5129: dilute 1:80 and 1:160 (R&D # AF5129)
        3.1.3 Abl-HRP-AF5414: dilute 1:900 (R&D # AF5414)
        3.1.4 BCR-HRP-1684-B-Dextran: dilute 1:80 (Epitomics #1684-B)
        3.1.5 GO-Dextran: dilute 1:80

3.2. Add 80 µl of antibody solution to the appropriate slide and incubate for 2 hours at room temperature.
  3.2.1 For Free BCR slide: BCR-HRP 1:80, GO-Dextran 1:80.
  3.2.2 For Total BCR-ABL slide: Abl-HRP 1:900, BCR-GO 1:80.
  3.2.3 For Phospho-BCR-ABL slide: 4G10-HRP 1:320, BCR-GO 1:160.
3.3. Wash the slide 5× such that the first wash is a quick rinse with 1.25 ml TBST and the remaining washes are for 3 minutes each.
4. Tyramide mediated signal amplification:
  4.1. Add 80 µl of biotin-tyramide at 1:320 dilution in 50 mM glucose/PBS (for BCR-HRP+GO-Dextran).
  4.2. Add 80 µl of biotin-tyramide at 6.25 ug/mL in 50 mM glucose/PBS-RK (for 4G10-HRP+BCR-GO and ABL-HRP+BCR-GO).
  4.3. Incubate for 15 minutes in the dark.
  4.4. Wash the slide 5× w such that the first wash is a quick rinse with 1.25 ml TBST and the remaining washes are for 3 minutes each.
5. Incubation with Alexa Fluor conjugated streptavidin:
  5.1. Incubate with 80 µl of Streptavidin-Alexa 647 at 0.4 m/ml in Assay Dilution Buffer (1:4,000 dilution) for 40 minutes.
  5.2. Wash the slide 5× such that the first wash is a quick rinse with 1.25 ml TBST and the remaining washes are for 3 minutes each.
  5.3. Wash once with water.
  5.4. Remove the frame and rinse the slide a couple of times with water.
  5.5. Centrifuge the slide at 1500 rpm in 50 ml tube for 3 minutes.
6. Dry and scan slide on Perkin Elmer scanner at the appropriate laser setting:
  6.1. Dry the slide.
  6.2. Scan the slide on Perkin Elmer scanner at the appropriate laser setting
  6.3. Save images and scan sets to files and server.

Example 7

Method for Selecting an Anticancer Therapy for a Patient with a Hematological Malignancy Characterized by Activated BCR-ABL Levels This example demonstrates a method for selecting an anticancer therapy for a patient with a BCR-ABL mediated diseases (e.g., chronic myelogenous leukemia). A patient is previously untreated for a BCR-ABL mediated disease and has not yet received drugs such as tyrosine kinase inhibitors (e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof). A patient's blood sample is drawn and incubated with different anticancer drugs at varying dosages for 1.5 hours at 37° C. Following this in vitro drug treatment, leukocytes and/or circulating tumor cells are recovered from the patient blood. The isolated cells are lysed and used in a proximity assay such as a Collaborative Proximity Immunoassay (COPIA) described in PCT Application No. PCT/US2010/042182, filed Jul. 15, 2010, and US Patent Publication Nos. 20080261829, 20090035792, and 20100167945, the disclosures of which are herein incorporated by reference in their entirety for all purposes. The pathway profiles, based upon the expression/activation profiling of analytes of signaling transduction pathway proteins (e.g., BCR-ABL, BCR, ABL, CRKL, AKT, SRC) in the drug treated patient samples, are determined in the presence of anticancer drugs. The profiles are used to select an anticancer treatment regimen aimed at achieving a positive clinically outcome.

As such, the present invention provides a method for selecting an anticancer drug in a subject having a hematological malignancy, the method comprising 1) measuring the activation state level of BCR-ABL in an isolated cell from a sample from the subject,) incubating the isolated cell with at least one anticancer drug prior to initiation of treatment; 3) measuring the activation state level of BCR-ABL in the incubated cells; and selecting a course of treatment based upon the activation state level of BCR-ABL. The present invention also provides a method for monitoring the efficacy of an anticancer drug in a subject, wherein the subject has a hematological malignancy, the method comprising: 1) measuring the activation state of BCR-ABL at $T_0$, prior to the first administration of the anticancer drug; 2) administering the anticancer drug to the subject, wherein the first administration of the anticancer drug is at time $T_1$; 2) measuring the activation state and or expression level of BCR-ABL at a time $T_2$ in a sample from the subject; and 3) determining a course of treatment based upon the activation state and or expression level of BCR-ABL.

Example 8

Patient 1: Pathway Profiling to Determine Efficacy of Treatment and/or to Select the Best Treatment Strategy Based on In Vitro BCR-ABL Inhibition Profile This example demonstrates the determination of the efficacy of inhibitor therapies for patients with BCR-ABL mediated diseases (e.g., chronic myelogenous leukemia), based upon the expression/activation profiling of analytes of signaling transduction pathway proteins (e.g., BCR-ABL, BCR, ABL, CRKL, AKT, SRC) in the subject's blood sample. In particular instances, patients may be receiving inhibitor therapy such as treatment with tyrosine kinase inhibitors (e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof). In other embodiments, the presence and/or activation state of a BCR-ABL substrate such as CRKL, AKT, STAT5 and SRC can be measured using a proximity assay such as a Collaborative Proximity Immunoassay (COPIA) described in PCT Application No. PCT/US2010/042182, filed Jul. 15, 2010, and U.S. Patent Publication Nos. 2008/0261829, 2009/0035792, and 2010/0167945, the disclosures of which are herein incorporated by reference in their entirety for all purposes. In addition, the expression/activation profiling of kinases and other signaling transduction pathway components in the subject's sample following in vitro treatment with tyrosine kinase inhibitors can provide valuable information to enable the clinician to select an effective therapeutic regimen.

In an exemplary example, blood samples from a patient (Patient 1) were analyzed to determine the effectiveness of the patient's imatinib therapy. Patient 1 is a 55-year old white, female with a primary diagnosis of chronic myelogenous leukemia (CML). She has active CML and has been receiving imatinib since diagnosis. The patient's blood was drawn and leukocytes were isolated using methods described above. In brief, Patient 1's whole blood sample was filtered through a filtration plate to recover leukocytes and circulating tumor cells. The cells were then lysed and used in a proximity assay (e.g., CEER and COPIA) that detects the activation state and/or total amount of one or a plurality of oncogenic fusion proteins (e.g., BCR-ABL) and/or signal transduction molecules (e.g., EGFR, HER-2, HER-3, HER-4, VEGFR-1, VEGFR-2, VEGFR-3, PDGFR, c-Met, c-KIT, IGF-IR, SHC, PI3K). In specific instances, the dilution series of capture antibodies used in the proximity assay is diluted 1:5 or 1:20 to achieve the desired concentrations. The number of white blood cells and the profile of phosphorylated BCR-ABL and other signaling transduction pathway components were determined using the proximity assay. The phosphorylation signal ratio was also calculated from the analysis and used to determine the patient's prognosis.

In a preferred embodiment, the patient's blood sample can be in vitro incubated with inhibitor treatments prior to isolation of leukocytes or circulating tumor cells. In particular instances, whole blood samples harvested from patients diagnosed with CML are treated with 0.1 µM, 1 µM or 10 µM BCR-ABL inhibitor (e.g., imatinib, nilotinib and dasatinib) for 1.5 hours at 37° C. The leukocytes or circulating tumor cells are isolated from the whole blood using a filtration method and lysed using techniques known to those in the art. The cell lysates are then used in a proximity assay to determine the effect of BCR-ABL inhibitor treatment on the activation state and/or total amount of one or a plurality of oncogenic fusion proteins (e.g., BCR-ABL) and/or signal transduction molecules. In certain embodiments, in vitro treatment with BCR-ABL inhibitors can reduce the levels of phosphorylated CRKL. In certain instances, CRKL activation in a patient sample can be due to BCR-ABL activation. In yet another embodiment, a specific inhibitor such as dasatinib may be able to attenuate the activated forms of AKT, STAT5 and SRC. In other instances, other inhibitors such as imatinib and nilotinib may not reduce the levels of phosphorylated AKT and STAT5 in the same patient. In particular instances, phosphorylated AKT and STAT signaling may not be dependent on BCR-ABL activation state. In another aspect, a patient currently receiving imatinib will likely respond to and should received a combination therapy such as imatinib and dasatinib due to attenuated expression/activation of BCR-ABL substrates such as CRKL, STAT5 and SRC.

Figure 11A:
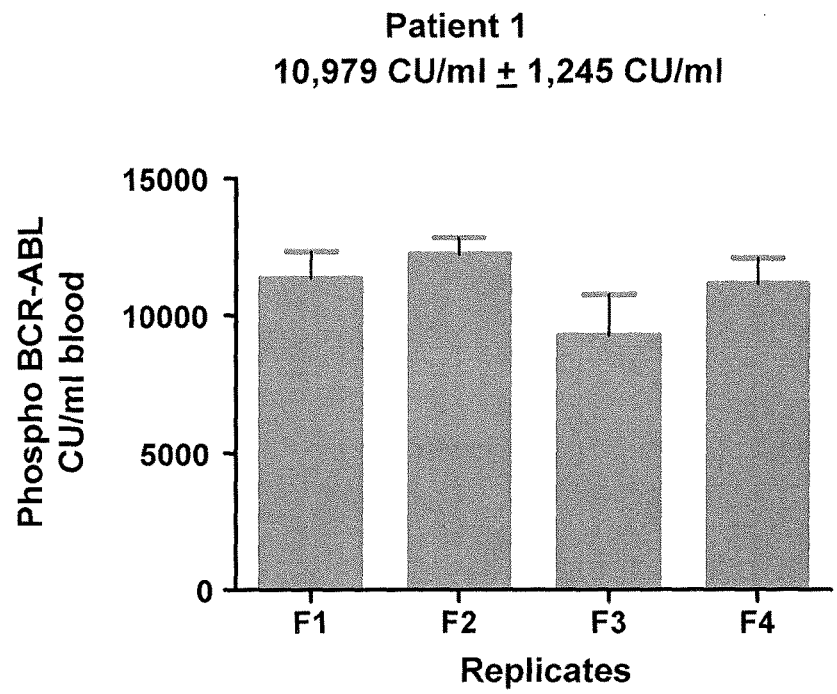
FIG. 11A-B illustrates that Patient 1 (A) has a lower amount of phospho-BCR-ABL per ml (e.g., 10,979 CU/ml±1,245 CU/ml) of blood as compared to Patient 2 (e.g., 185,934 CU/ml±11,019 CU/ml) (B), suggesting that Patient 1 is responding to imatinib treatment. The values were determined without subtracting the blood background.
Figure 11B:
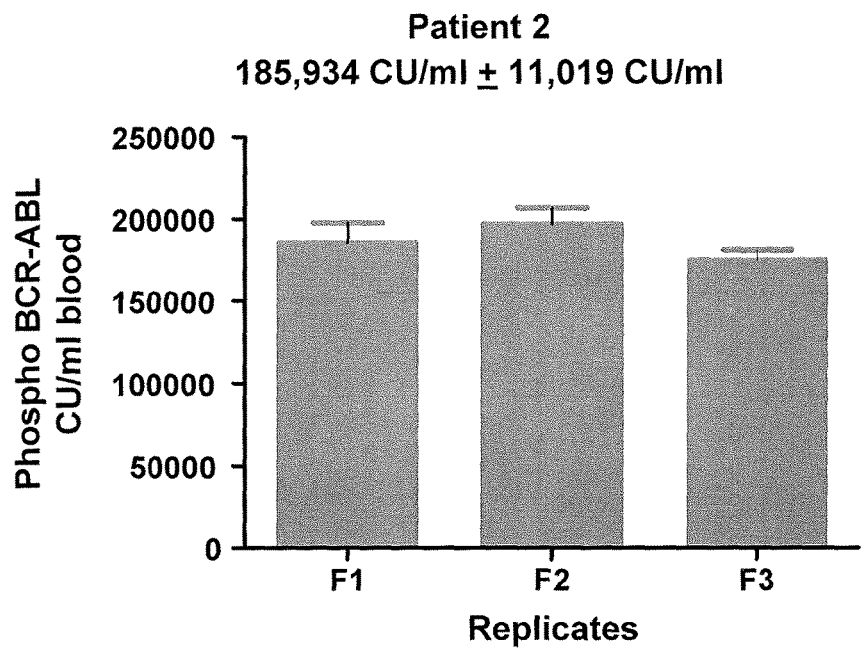
Figure 12A:
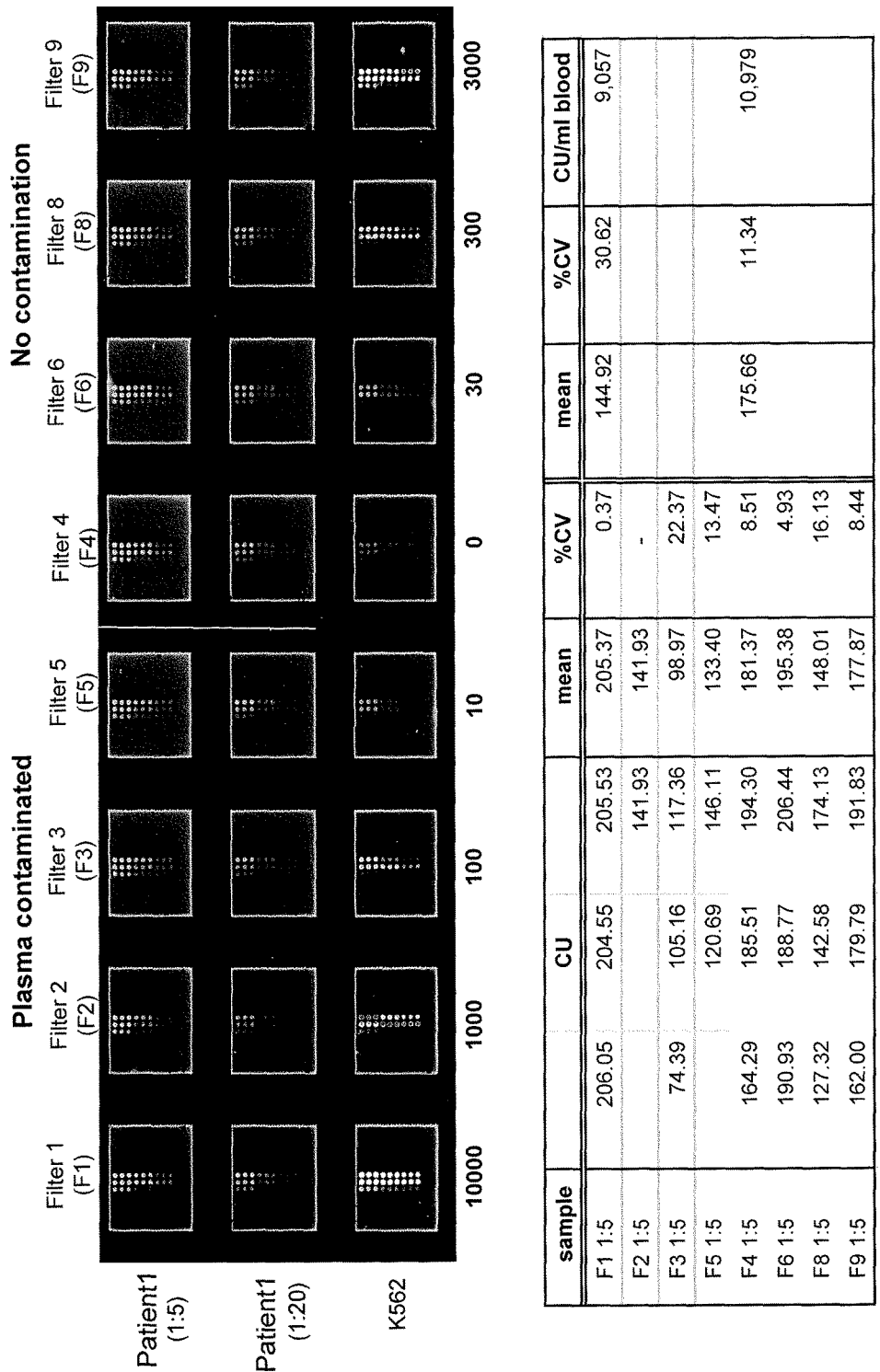
Figure 13A:
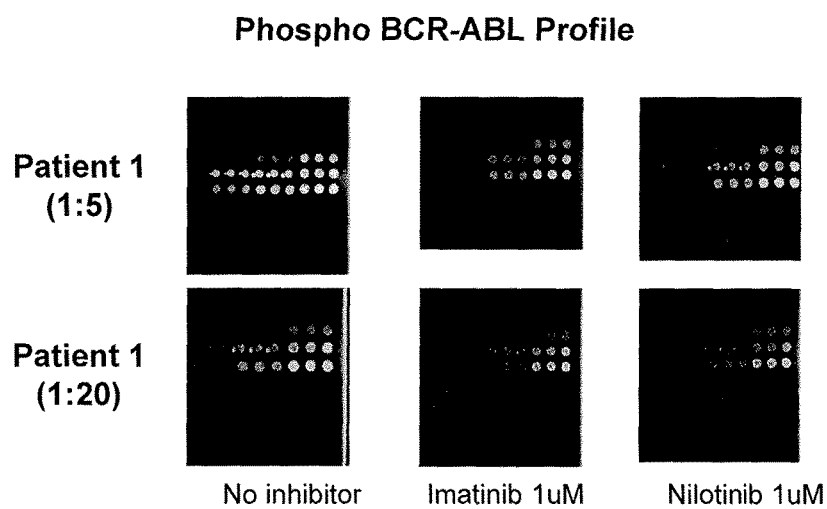
FIG. 13A-B shows that in vitro treatment with imatinib of blood sample from Patient 1 dramatically decreased the amount of phosphorylated BCR-ABL, as compared to nilotinib treatment.
Figure 13B:
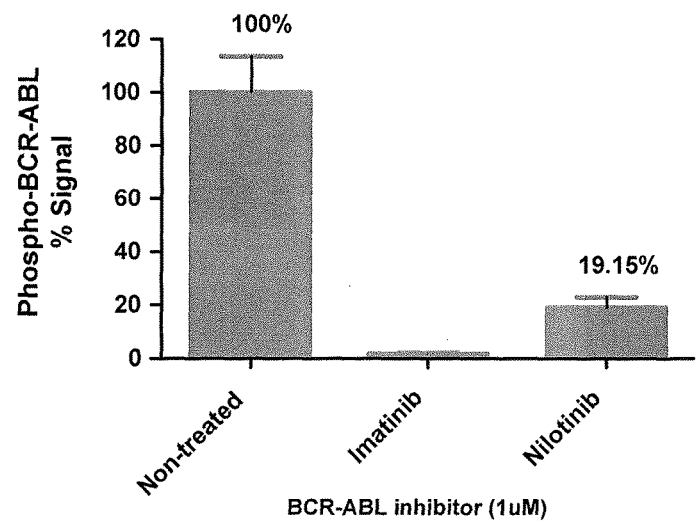
Figure 14:
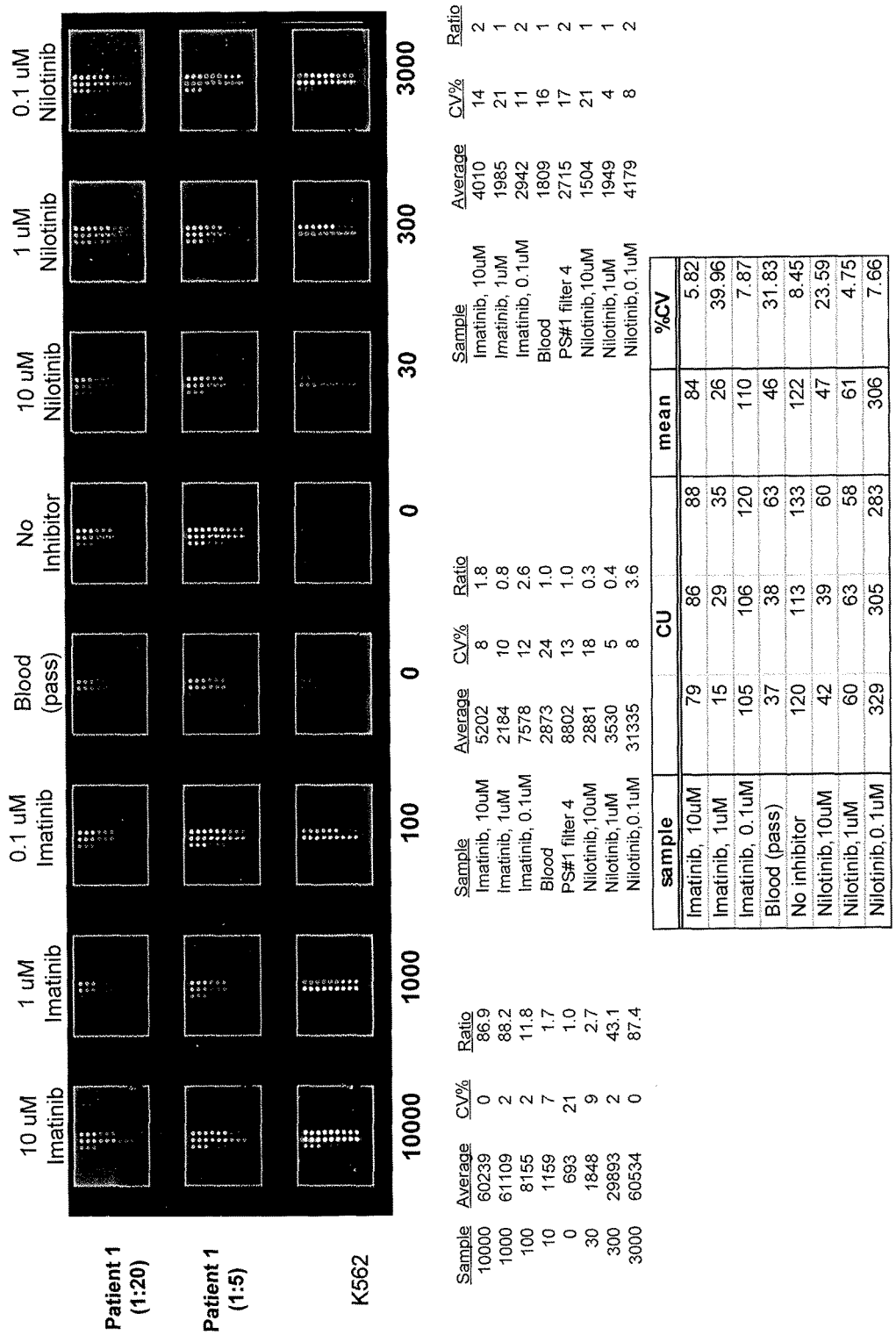
FIG. 14 shows that activated BCR-ABL levels in Patient 1's blood sample change when treated with increasing amounts of BCR-ABL inhibitor (e.g., imatinib or nilotinib). Different drug concentrations were incubated with Patient 1's blood sample for 1.5 hours at 37° C. The mean CU value after 1 µM imatinib treatment was 26, and 110 after 0.1 µM imatinib treatment. The top panel of FIG. 13 shows the images of the BCR-ABL CEER Assays.
Figure 15A:
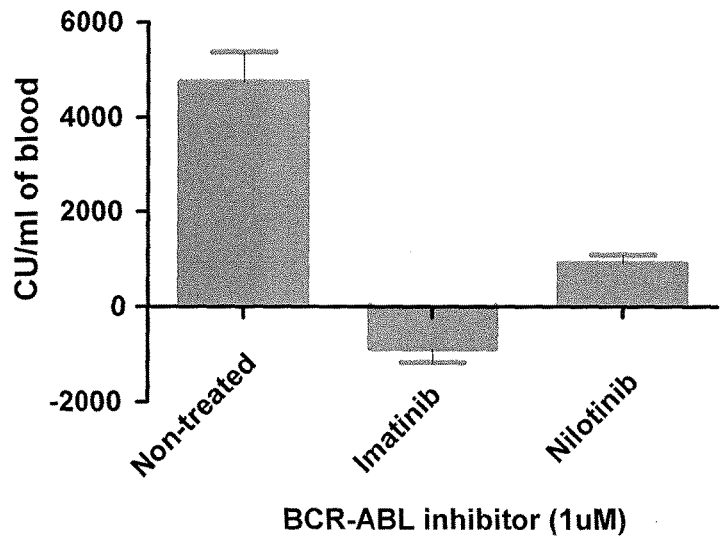
FIG. 15A-B show that imatinib is more effective than nilotinib at reducing activated BCR-ABL protein in Patient 1's blood sample. The bar graphs show that 1 µM imatinib treatment decreased activated BCR-ABL levels (A) as compared to the untreated sample.
Figure 15B:
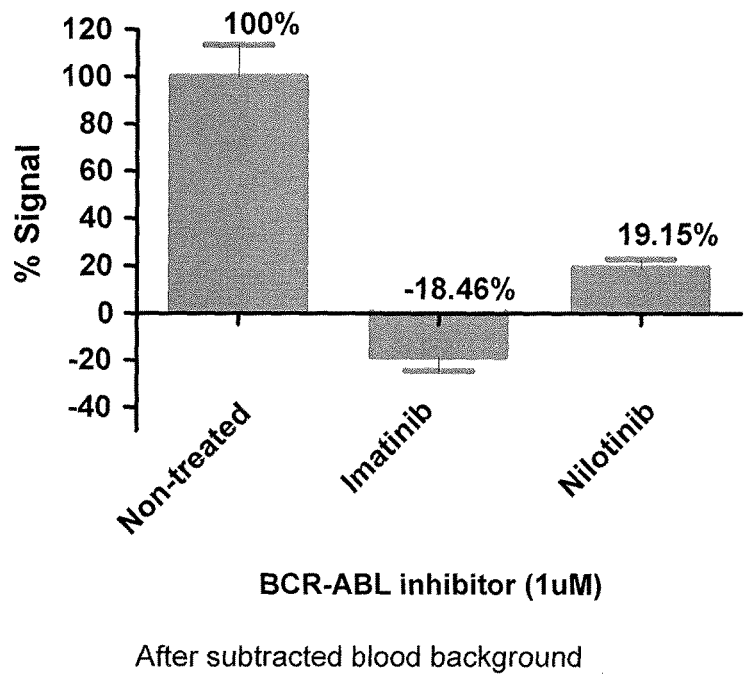
Figure 16A:
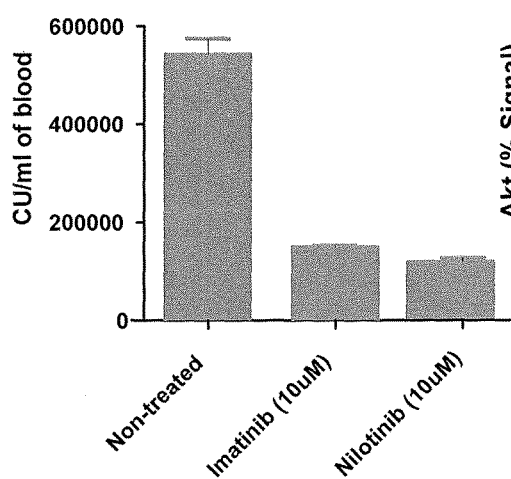
FIG. 16A-D illustrates the pathway profile of other phosphorylated signaling transduction pathway components such as CRKL (A), AKT (B), STAT5 (C) and SRC (D). It shows dasatinib therapy can reduce the levels of activated AKT, STAT4 and SRC in Patient 1's blood sample. In vitro treatment of Patient's blood samples with 1 µM dasatinib was more effective than either 10 µM imatinib or 10 µM nilotinib.
Figure 16B:
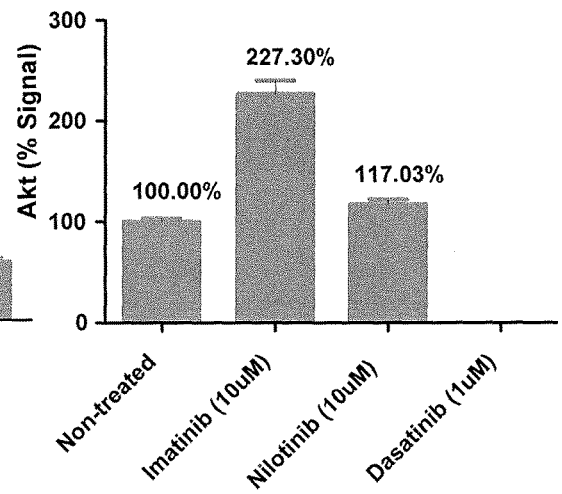
Figure 16C:
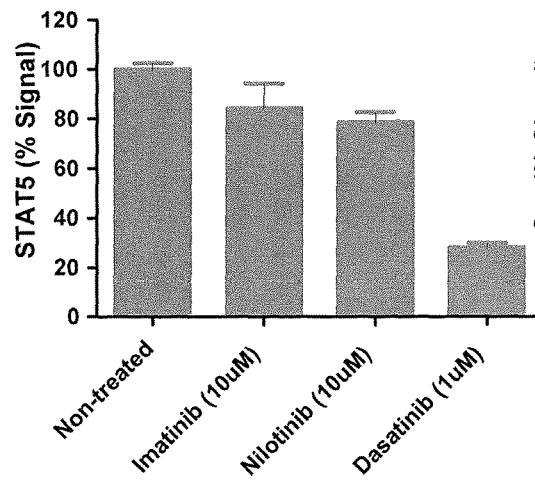
Figure 16D:
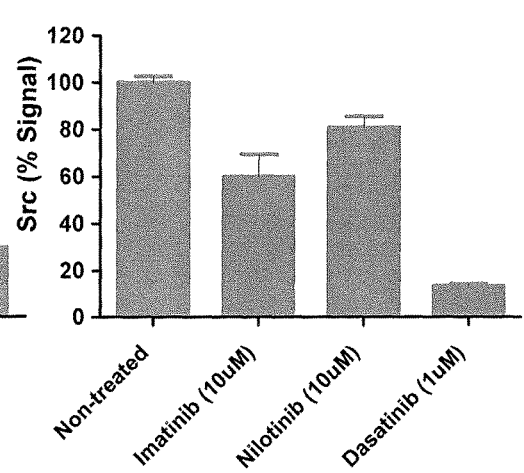
Figure 17:
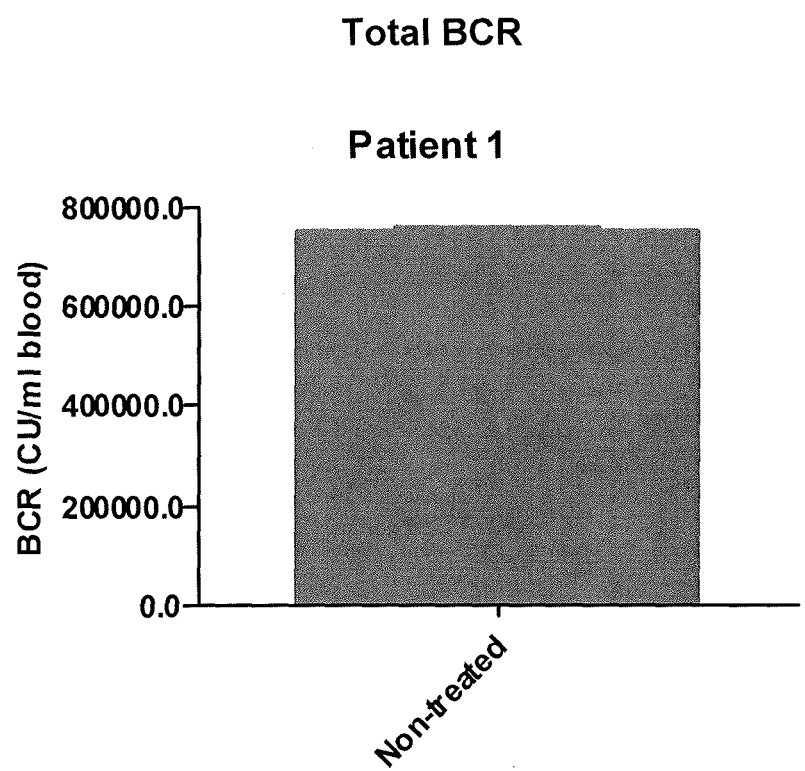
FIG. 17 shows that Patient 1's blood sample contains very high levels of total BCR (about 8,000,000 CU/ml).

FIG. 10 describes the patients analyzed in this study. Patient 1 has active CML and has been receiving treatment for at least 5 years. Patient 2 who also has active CML has been receiving imatinib treatment for 1 year. FIG. 11A-B illustrate that Patient 1 had a lower amount of phospho-BCR-ABL per ml of blood as compared to Patient 2 (10,979 CU/ml versus 185,934 CU/ml), suggesting that Patient 1 was responding to imatinib treatment. FIG. 12A-B show the detection of total and activated (phosphorylated) levels of BCR-ABL as determined by a sandwich ELISA, following filtration isolation of leukocytes and other circulating tumor cells. The proximity assay can detect levels of phosphor-BCR-ABL in K562 cells. FIG. 13A-B show that in vitro treatment with imatinib of blood sample from Patient 1 dramatically decreased the amount phosphorylated BCR-ABL, as compared to nilotinib treatment. FIGS. 14 and 15 show that activated BCR-ABL levels in Patient 1's blood sample were changed when treated with increasing amounts of BCR-ABL inhibitor. In this experiment, blood samples from Patient 1 were treated for 1.5 hours in vitro with varying amounts of BCR-ABL inhibitors (e.g., 10 µM, 1 µM or 0.1 µM imatinib, or 10 µM, 1 µM or nilotinib). The results show that the mean phospho-BCR-ABL signal was 84 CU for 10 µM imatinib, 26 CU for 1 µM imatinib, and 110 CU for 0.1 µM imatinib. The mean level of activated BCR-ABL signal was 47 CU for 10 µM nilotinib, 61 CU for 1 µM nilotinib, and 306 CU for 0.1 µM nilotinib. FIG. 15A-B show that imatinib was more effective than nilotinib at reducing activated BCR-ABL protein in Patient 1's blood sample. The percentage recovery of activated BCR-ABL signal was −18.46% in the sample treated in vitro with 1 µM imatinib and 19.15% in the sample exposed to 1 µM nilotinib (FIG. 15B). FIG. 16A-D illustrates the pathway profile of other phosphorylated signaling transduction pathway components such as CRKL (A), AKT (B), STAT5 (C) and SRC (D). It shows that dasatinib therapy, and not imatinib or nilotinib, resulted in reduced levels of activated AKT, STAT4 and SRC in Patient 1's blood sample. FIG. 17 shows that Patient 1's blood sample contained very high levels of total BCR (8 million CU/ml).

Example 9

Patient 2: Pathway Profiling to Determine Efficacy of Treatment and/or to Select the Best Treatment Strategy Based on In Vitro BCR-ABL Inhibition Profile This example demonstrates the determination of the efficacy of inhibitor therapies for patients with BCR-ABL mediated diseases (e.g., chronic myelogenous leukemia), based upon the expression/activation profiling of analytes of signaling transduction pathway proteins (e.g., BCR-ABL, BCR, ABL, CRKL, AKT, SRC) in the subject's blood sample. In particular instances, patients may be receiving inhibitor therapy such as treatment with tyrosine kinase inhibitors (e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof). In other embodiments, the presence and/or activation state of a BCR-ABL substrate such as CRKL, AKT, STAT5 and SRC can be measured using a proximity assay such as a Collaborative Proximity Immunoassay (COPIA) described in PCT Application No. PCT/US2010/042182, filed Jul. 15, 2010, and US Patent Publication Nos. 2008/0261829, 2009/0035792, and 2010/0167945, the disclosures of which are herein incorporated by reference in their entirety for all purposes. In addition, the expression/activation profiling of kinases and other signaling transduction pathway components in the subject's sample following in vitro treatment with tyrosine kinase inhibitors can provide valuable information to enable the clinician to select an effective therapeutic regimen.

In an exemplary example, the patient (Patient 2) is a 39-year old white, male diagnosed with CML in January. Patient 2 has been receiving imatinib since diagnosis and has active disease. In a preferred embodiment, the patient's blood is drawn and leukocytes are isolated using methods described above. In brief, Patient 2's whole blood sample was filtered through a filtration plate to recover leukocytes and circulating tumor cells. The cells were then lysed and used in a proximity assay (e.g., CEER and COPIA) that detects the activation state and/or total amount of one or a plurality of oncogenic fusion proteins (e.g., BCR-ABL) and/or signal transduction molecules (e.g., EGFR, HER-2, HER-3, HER-4, VEGFR-1, VEGFR-2, VEGFR-3, PDGFR, c-Met, c-KIT, IGF-IR, SHC, PI3K). In specific instances, the dilution series of capture antibodies used in the proximity assay may be diluted 1:5 or 1:20 to achieve the desired concentrations. The number of white blood cells and the profile of phosphorylated BCR-ABL and other signaling transduction pathway components can be determined using the proximity assay. The phosphorylation signal ratio can also be calculated from the analysis and used to determine the patient's prognosis.

In a preferred embodiment, patient's blood sample can be in vitro incubated with inhibitor treatments prior to isolation of leukocytes or circulating tumor cells. In particular instances, whole blood samples harvested from patients diagnosed with CML are treated with 1 uM BCR-ABL inhibitor (e.g., imatinib, nilotinib and dasatinib) for 1.5 hours at 37° C. The leukocytes or circulating tumor cells are isolated from the whole blood using a filtration method and lysed using techniques known to those in the art. The cell lysates are then used in a proximity assay to determine the effect of BCR-ABL inhibitor treatment on the activation state and/or total amount of one or a plurality of oncogenic fusion proteins (e.g., BCR-ABL) and/or signal transduction molecules. In certain embodiments, in vitro treatment with nilotinib, and not imatinib will reduce the percentage of phospho-BCR-ABL recovered in a patient's blood sample. In a particular instance, a patient with this pathway profile will likely respond better to nilotinib therapy, compared to imatinib. In other embodiments, in vitro treatment with BCR-ABL inhibitors can have no effect on phosphorylated CRKL. In another embodiment, a specific inhibitor such as dasatinib may be able to attenuate the activated forms of AKT, STAT5 and SRC. In other instances, other inhibitors such as imatinib and nilotinib may reduce the levels of phosphorylated AKT in the same patient sample. In yet another instance, phosphorylated STAT5 and SRC are reduced by about 20% due to in vitro treatment with imatinib and nilotinib. In another aspect, a patient currently receiving imatinib will likely respond better to and should received dasatinib therapy, due to attenuated expression/activation of BCR-ABL substrates such as AKT, STAT5 and SRC.

Figure 18A:
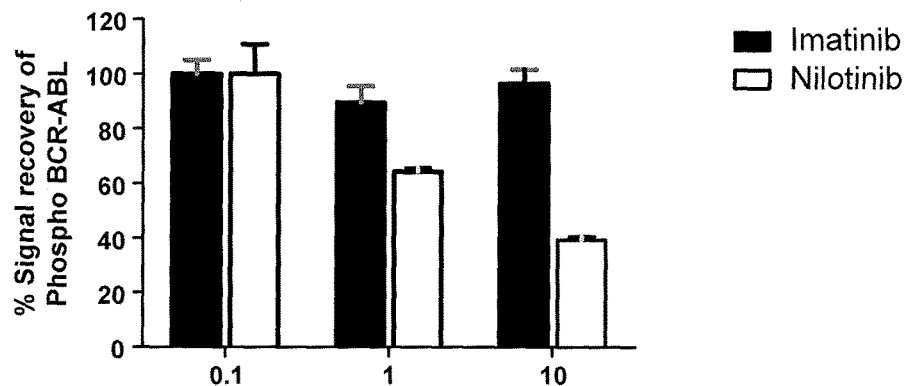
FIG. 18A-B illustrate that nilotinib is more effective compared to imatinib at decreasing activated BCR-ABL levels in in vitro-treated blood samples from Patient 2.
Figure 18B:
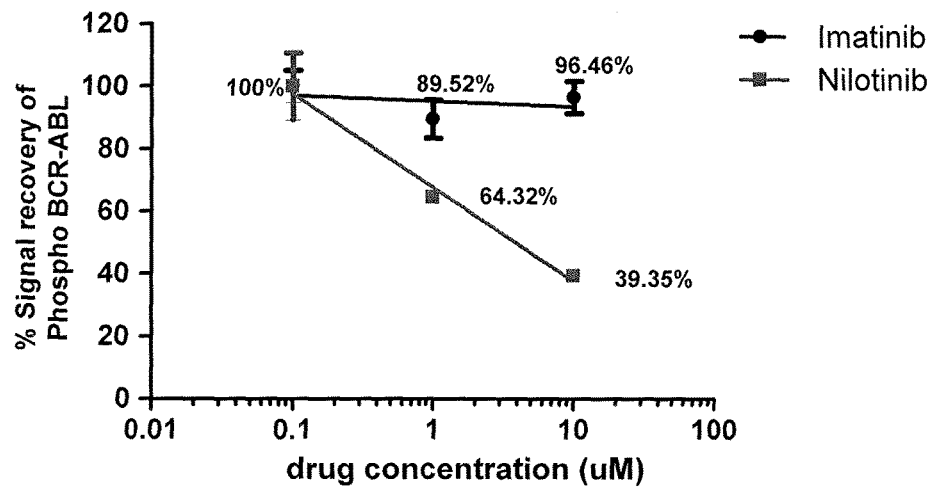
Figure 19A:
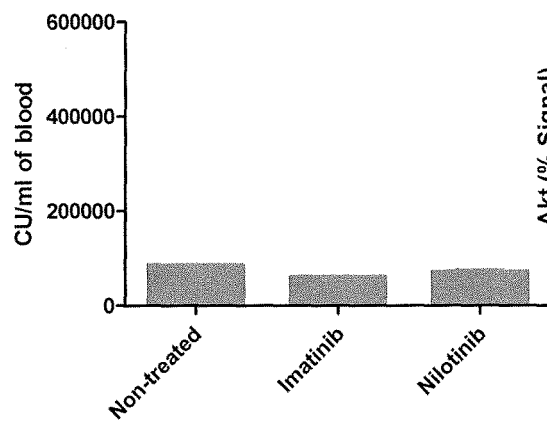
FIG. 19A-D show that in vitro treatment of Patient 2's blood sample with dasatinib can reduce the levels of activated CRKL (A), AKT (B), STAT5 (C) and SRC (D). On the other hand, similar treatment with either imatinib or nilotinib treatment reduces only phosphorylated AKT.
Figure 19B:
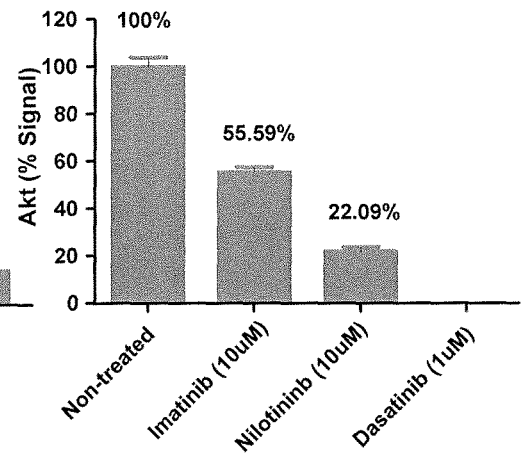
Figure 19C:
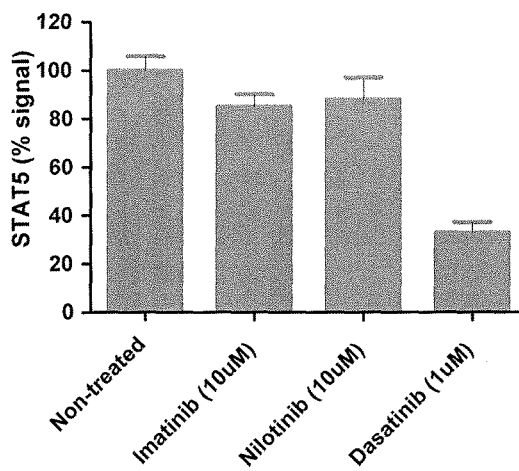
Figure 19D:
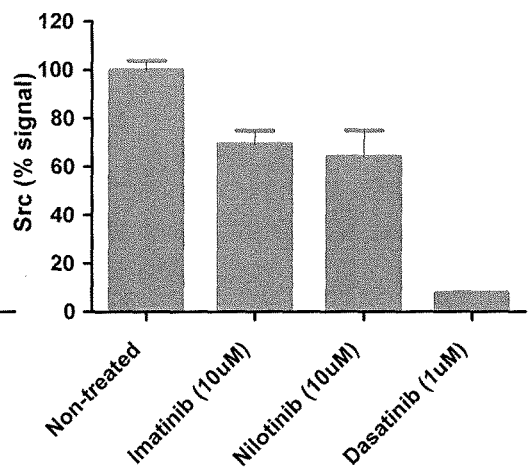
Figure 20A:
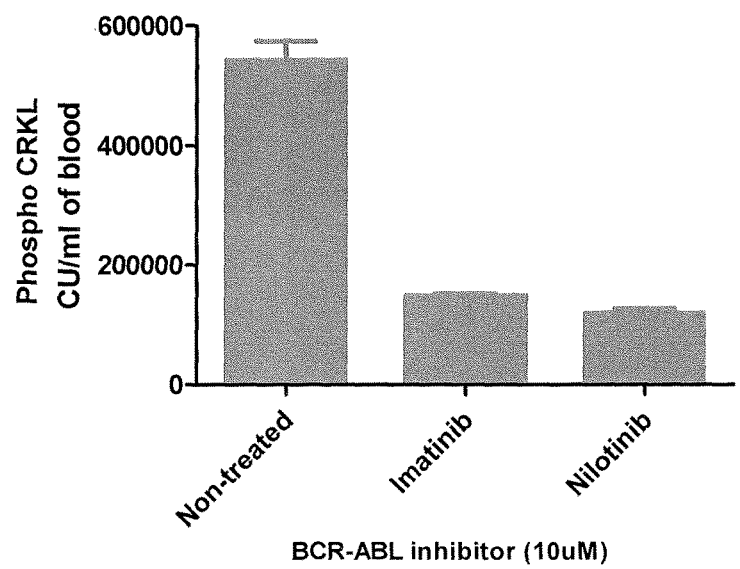
FIG. 20A-D show that phosphorylated CRKL levels can be detected and measured in several patients' blood samples that were also treated with tyrosine kinase inhibitors in vitro. BCR-ABL inhibitors such as imatinib and nilotinib can reduce CRKL levels only in blood samples from Patient 1, and not Patient 2.
Figure 20B:
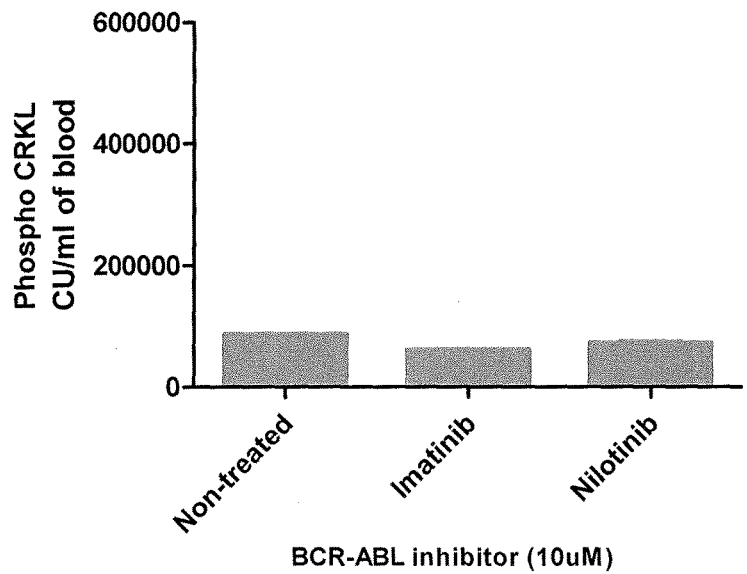
Figure 20C:
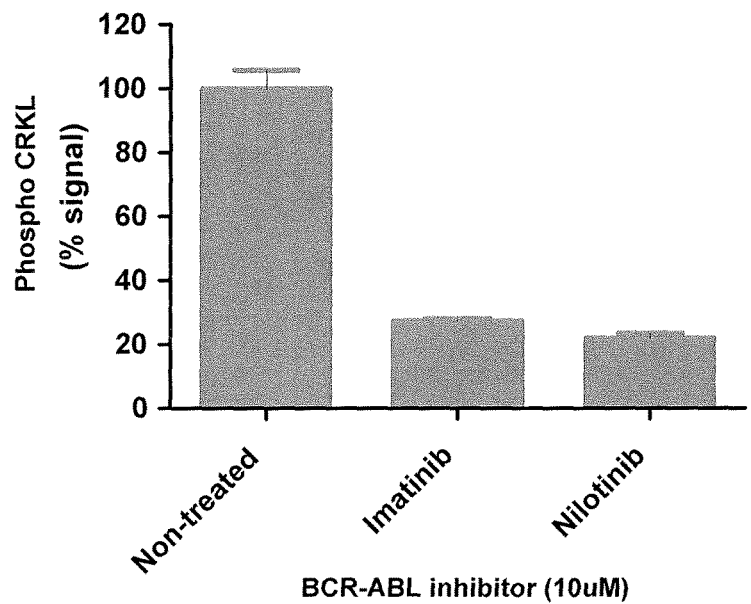
Figure 20D:
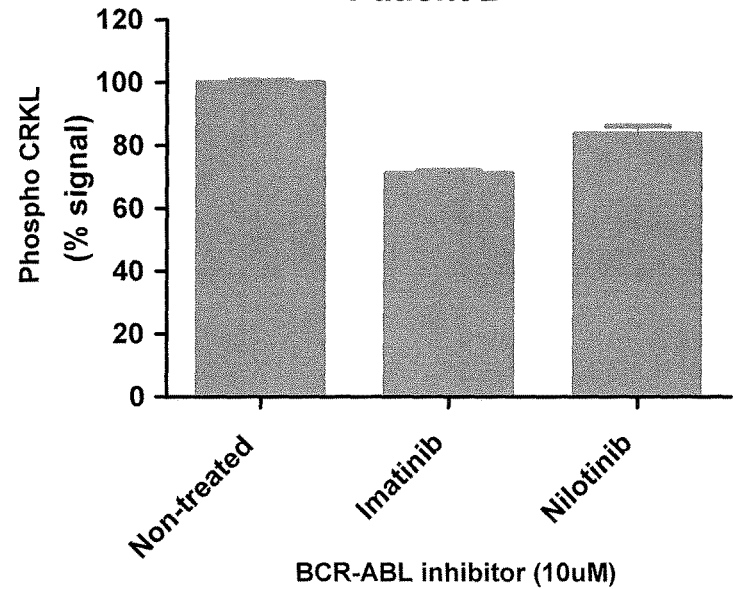
Figure 21A:
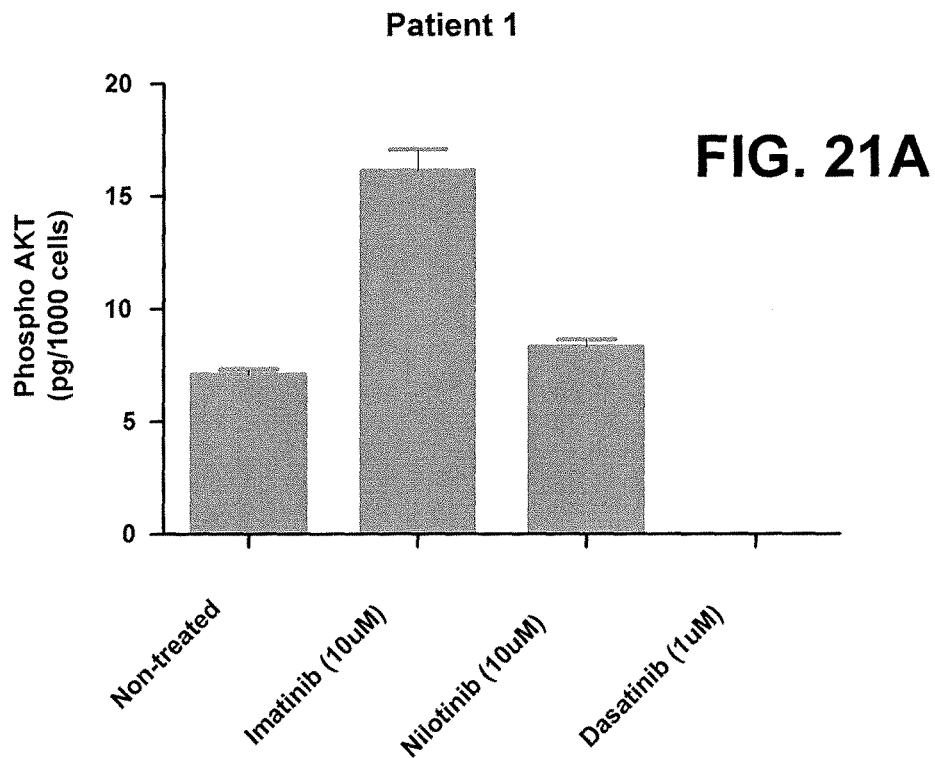
FIG. 21A-D illustrates that Patient 1 and Patient 2 do not similarly respond to imatinib and nilotinib. Activated AKT increased in samples from Patient 1 following imatinib treatment, and yet they decreased in samples from Patient 2. In response to nilotinib, AKT levels remain mostly unchanged in samples from Patient 1 as compared to non-treated samples, and they greatly decrease in samples from Patient 2.
Figure 21B:
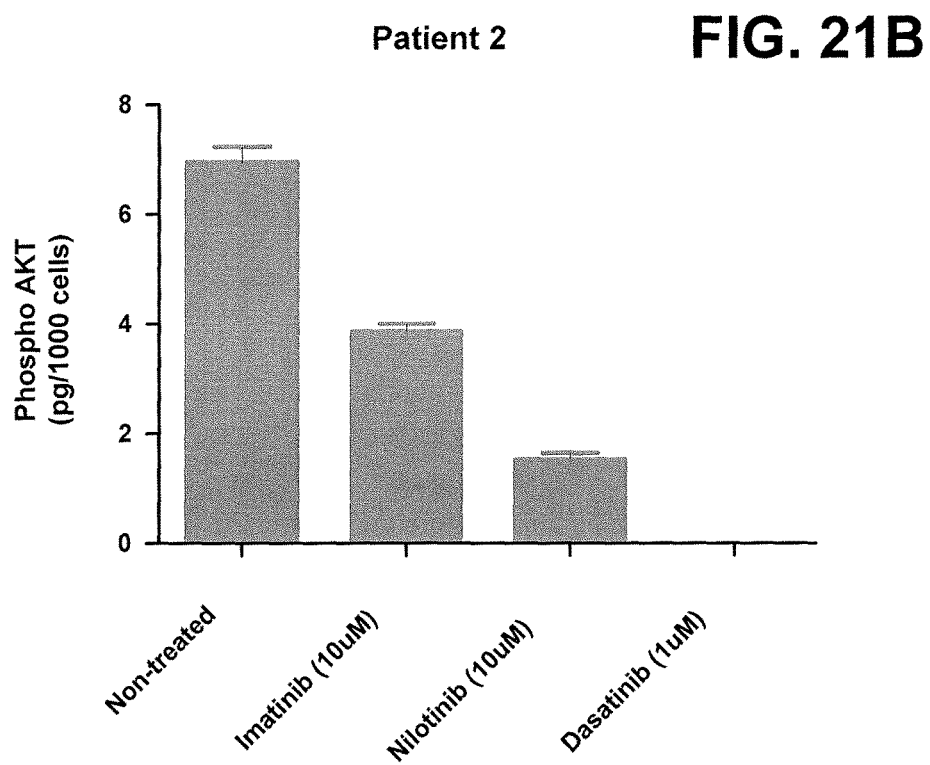
Figure 21C:
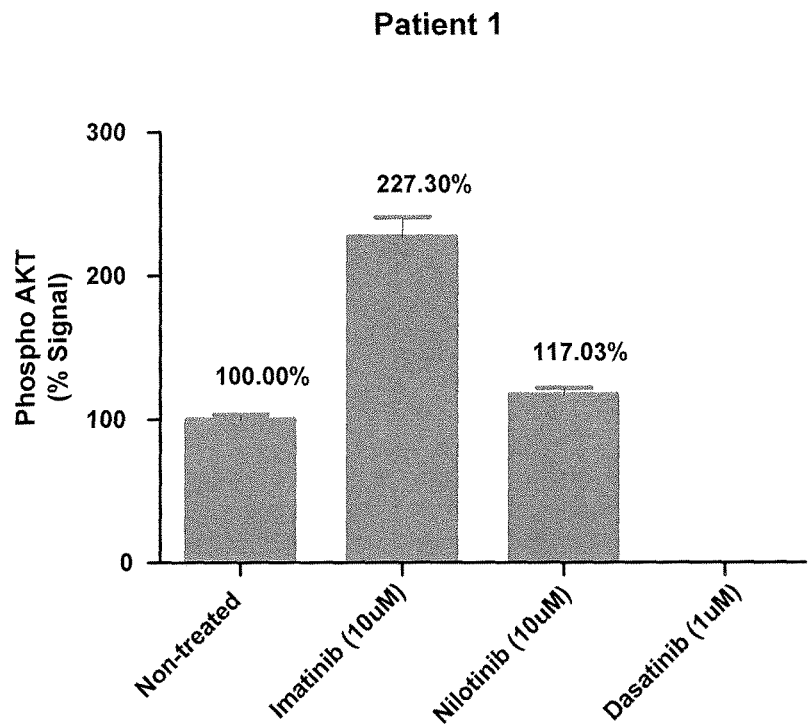
Figure 21D:
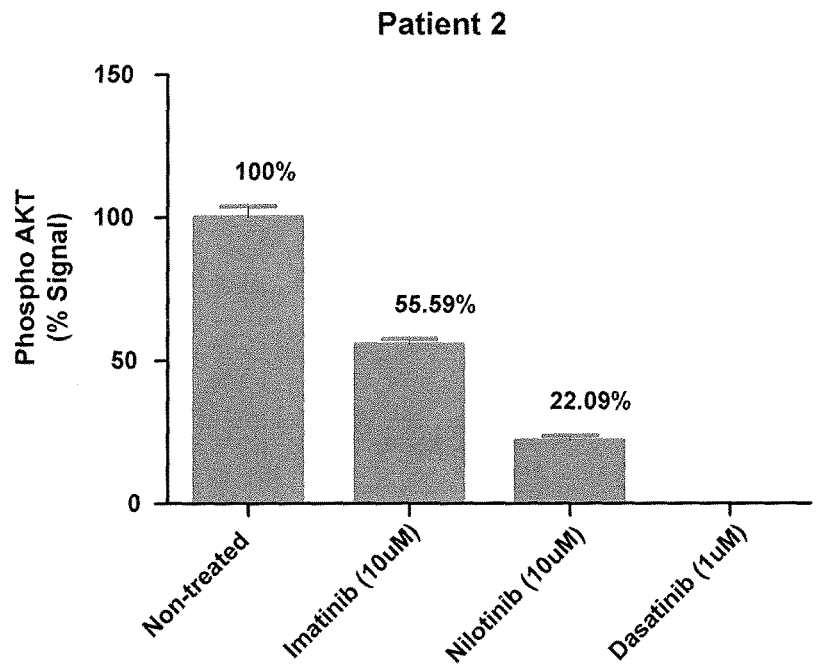

FIG. 18A-B show that phosphorylated BCR-ABL was detected and measured following an in vitro treatment of Patient 2's blood samples with different dosages of BCR-ABL inhibitors for 1.5 hours at 37° C. It also shows that nilotinib is more effective compared to imatinib at decreasing activated BCR-ABL in vitro-treated blood samples from Patient 2. Increasing the concentration of nilotinib (e.g., 0.1 µM, 1 µM. and 10 µM) decreased activated BCR-ABL, while varying imatinib concentration had less effect (FIG. 18B). Imatinib had very little effect on activated BCR-ABL levels in Patient 2. FIG. 19A-D shows that in vitro treatment of Patient 2's blood sample with dasatinib reduced the levels of activated AKT (B), STAT5 (C) and SRC (D). On the other hand, similar treatment with either imatinib or nilotinib treatment reduced only phosphorylated AKT (e.g., 55.54% in 10 µM imatinib treatment sample compared to 100% in non-treated sample).

Example 10

Comparison of Pathway Profiles of Blood Samples from Patients on Imatinib for Chronic Myelogenous Leukemia The example demonstrates that pathway profiles based upon the expression/activation profiling of analytes of signaling transduction pathway proteins (e.g., BCR-ABL, BCR, ABL, CRKL, AKT, SRC) in the subject's blood sample can be determined and compared to establish the efficacy of various therapeutic regimens. In a preferred embodiment, the presence and/or activation state of a BCR-ABL substrate such as CRKL, AKT, STAT5 and SRC can be measured using a proximity assay such as a Collaborative Proximity Immunoassay (COPIA) described in PCT Application No. PCT/US2010/042182, filed Jul. 15, 2010, and U.S. Patent Publication Nos. 2008/0261829, 2009/0035792, and 2010/0167945, the disclosures of which are herein incorporated by reference in their entirety for all purposes. In other embodiments, patients may be receiving inhibitor therapy such as treatment with tyrosine kinase inhibitors (e.g., imatinib mesylate (Gleevec®), nilotinib (Tasigna®), dasatinib (Sprycel®), bosutinib (SKI-606), gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), leflunomide (SU101), vandetanib (ZACTIMA™; ZD6474), ponatinib (AP24534), and combinations thereof). In other embodiments, patient blood samples can be treated with tyrosine kinase inhibitors in vitro for 1.5 hours at 37° C. After which, circulating tumor cells and/or leukocytes can be recovered from the blood sample using filtration methods described herein. The isolated cells can be lysed and used in a proximity assay (e.g., CEER and COPIA) that detects the activation state and/or total amount of one or a plurality of oncogenic fusion proteins (e.g., BCR-ABL) and/or signal transduction molecules (e.g., EGFR, HER-2, HER-3, HER-4, VEGFR-1, VEGFR-2, VEGFR-3, PDGFR, c-Met, c-KIT, IGF-IR, SHC, PI3K, CRKL, AKT, STAT5, SRC). The measured levels of these proteins can be compared between samples from the same patient or from others. The comparison of pathway profiles enable a clinician to select the most effective therapy for a patient with a BCR-ABL mediated disease.

FIG. 20A-D show that phosphorylated CRKL levels were detected and measured in blood samples that were also treated with tyrosine kinase inhibitors in vitro. In this experiment, the capture antibodies used in the proximity assays were diluted 1:10 or 1:50 to achieve the desired concentrations. Patient 1 showed higher levels of activated CRKL compared to Patient 2. BCR-ABL inhibitors such as imatinib and nilotinib reduced CRKL levels only in blood samples from Patient 1, and not Patient 2.

FIG. 21A-D illustrate that Patient 1 and Patient 2 do not respond similarly to imatinib and nilotinib. Activated AKT levels increase in samples from Patient 1 following imatinib treatment, and yet they decrease in samples from Patient 2. In response to nilotinib, AKT levels remain mostly unchanged in samples from Patient I, and they greatly decrease in samples from Patient 2.

Figure 22A:
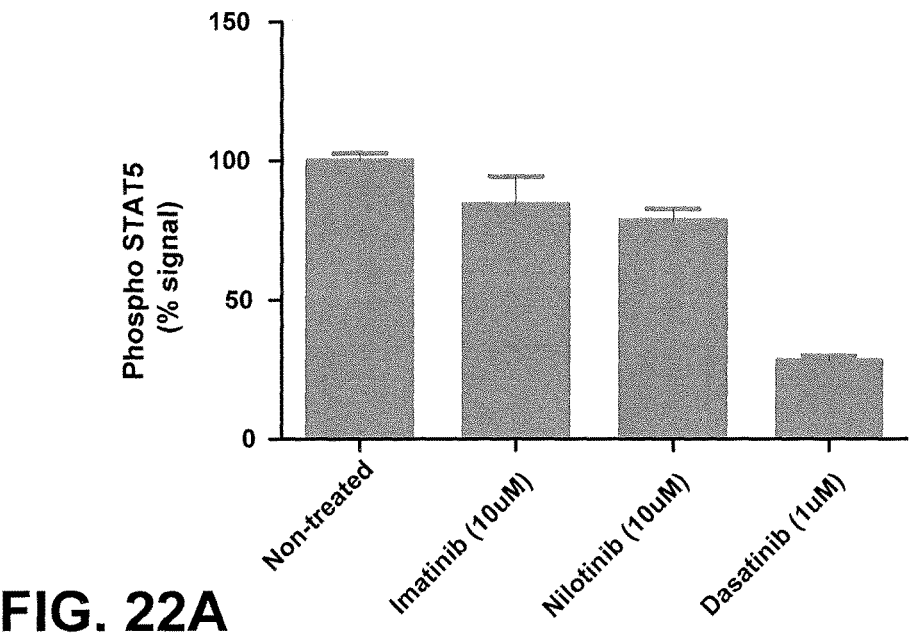
FIG. 22A-B show activated STAT5 profiles of in vitro-treated blood samples from Patient 1 (A) and Patient 2 (B). Dasatinib treatment decreased phospho-STAT5 levels in samples from Patient 1 and 2. Imatinib or nilotinib treatment did not change activated STAT5 to the same extent.
Figure 22B:
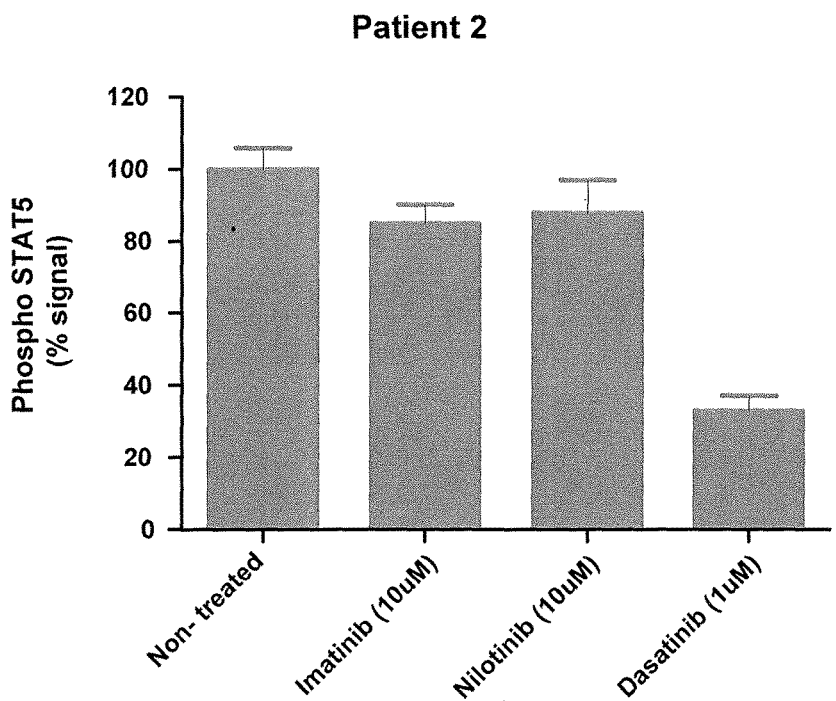
Figure 23A:
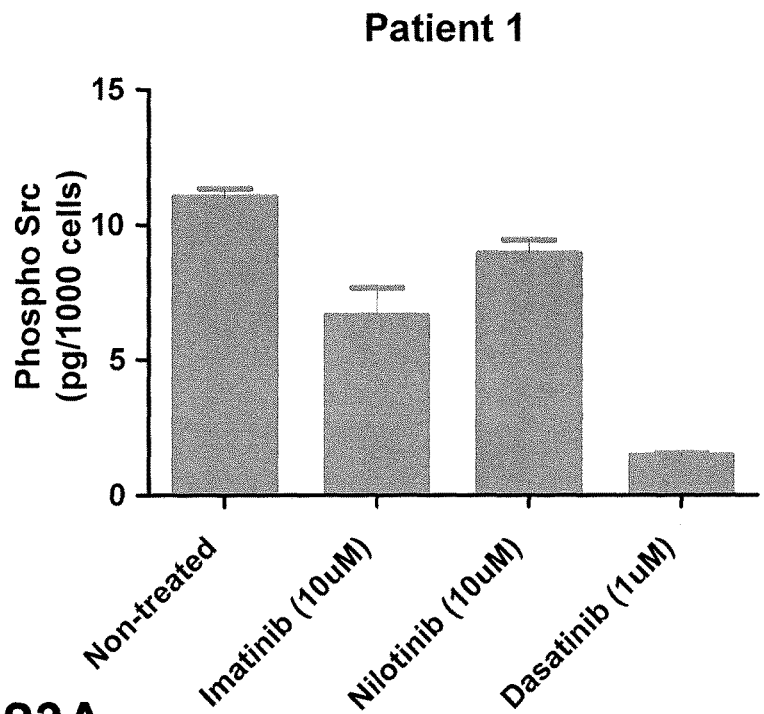
FIG. 23A-B show that samples from both Patient 1 and 2 have lower levels of phospho-SRC in response to imatinib, nilotinib and dasatinib.
Figure 23B:
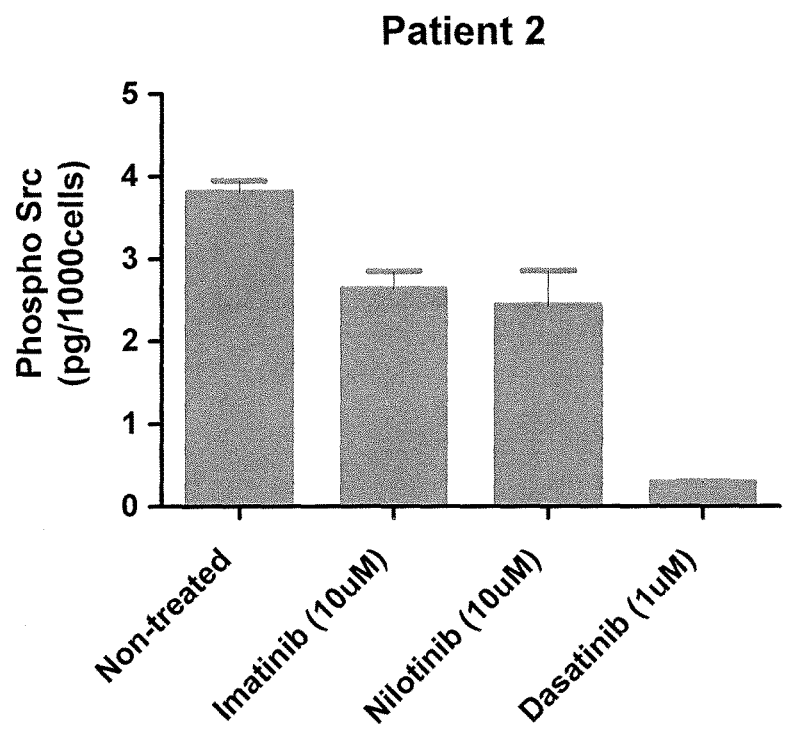
Figure 23C:
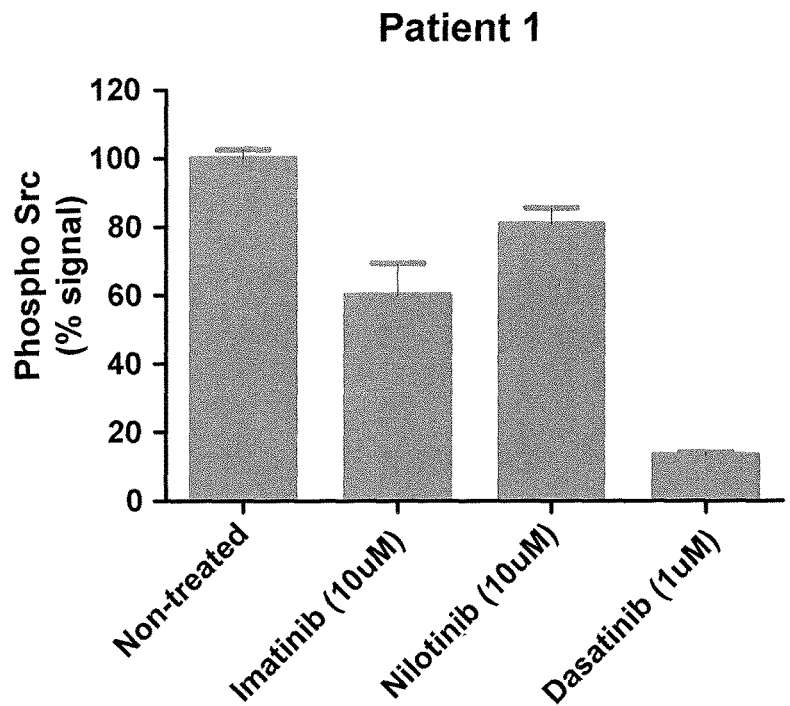
FIG. 23C-D illustrate phospho SRC levels as a percentage of phospho SRC signal recovered.
Figure 23D:
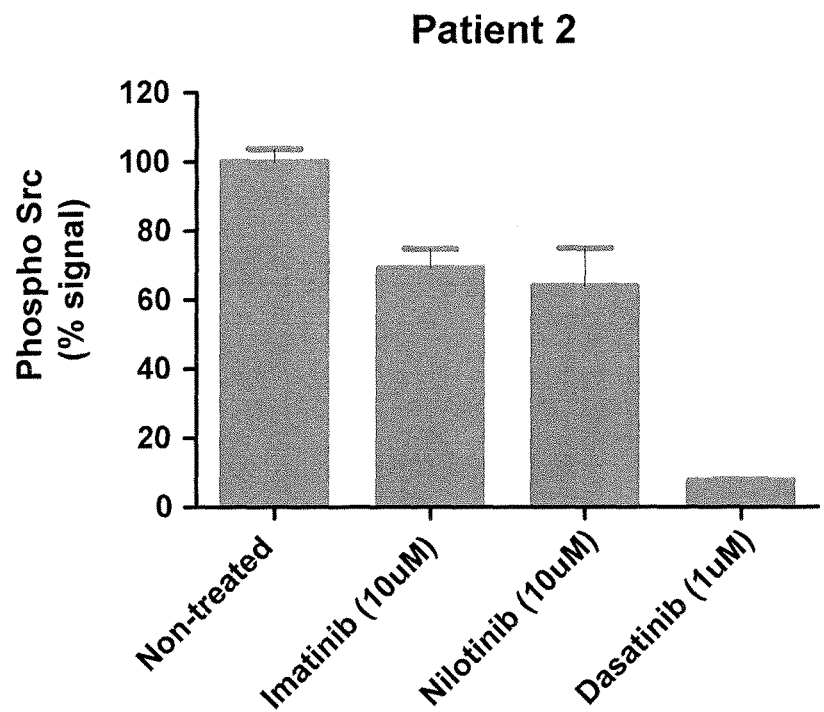

FIG. 22A-B show that in vitro dasatinib treatment can decrease phospho-STAT5 levels in samples from Patient 1 (A) and 2 (B). Activated STAT5 levels are similar in samples from either Patient 1 or Patient 2 that received no treatment, 10 µM imatinib and 10 µM nilotinib.

FIG. 23A-D show that samples from both Patient 1 and 2 have lower levels of phospho-SRC in response to imatinib, nilotinib and dasatinib. Dasatinib was more effective at decreasing phospho-SRC levels compared to imatinib and nilotinib in both Patient 1 and Patient 2 samples.

Example 11

Detecting and Monitoring Activation of BCR-ABL in CML Patients

This example illustrates the methods of the present invention of monitoring treatment response in a patient diagnosed with CML. This example illustrates that the methods can detect the expression and activation state of multiple proteins from a limited number of cells. This example shows that the methods for using the cell isolation apparatus of the present invention and the CEER immunoassay provides a more sensitive and quantitative analysis of functional target modulations, as compared to mRNA-based analysis.

Traditional methods for monitoring CML treatment response include cytogenetic testing, bone marrow aspiration smear evaluation, fluorescence in situ hybridization (FISH) of Ph chromosome, and real-time quantitative polymerase chain reaction (Q-PCR). Typically, cytogenetic testing or bone aspiration smear evaluation is performed at 3, 6, and 12 months of treatment or until CCyR attained. Currently, Q-PCR is the most sensitive test for treatment response. The present invention provides methods for monitoring in vivo modulations of BCR-ABL kinase inhibition that are more sensitive than Q-PCR and do not require the removal or dilution of drug in the patient's blood sample.

In this study, the levels of total and activated BCR-ABL were analyzed from CML patients using the methods of the present invention. FIG. 24 represents a table of patients evaluated in this study. The date of the diagnosis and the patient's course of treatment were recorded. Blood was drawn at various time points during the course of the study. Leukocytes and circulating tumor cells were isolated from the patient blood samples and lysed according to methods described herein. Cell lysate was processed and analyzed by methods described in Example 6. Modulations of the expression and activation of BCR-ABL and other signaling molecules (e.g., AKT, SRC, CRKL and STAT5) in the patient blood sample were determined using a proximity assay (e.g., COPIA or CEER). Detailed descriptions of a proximity assay such as a Collaborative Proximity Immunoassay (COPIA) described in PCT Application No. PCT/US2010/042182, filed Jul. 15, 2010, and US Patent Publication Nos. 2008/0261829, 2009/0035792, and 2010/0167945, the disclosures of which are herein incorporated by reference in their entirety for all purposes.

Monitoring CML Progression in Patients Following Drug Treatment.

FIG. 25 represents the total and activated BCR-ABL levels detected in patient samples using the methods of the present invention. Further details of the patient samples are described in this example.

Total BCR, ABL and BCR-ABL levels were determined from a blood sample from a normal, healthy subject. As expected, BCR-ABL levels were negative (see, FIG. 26).

Figure 27A:
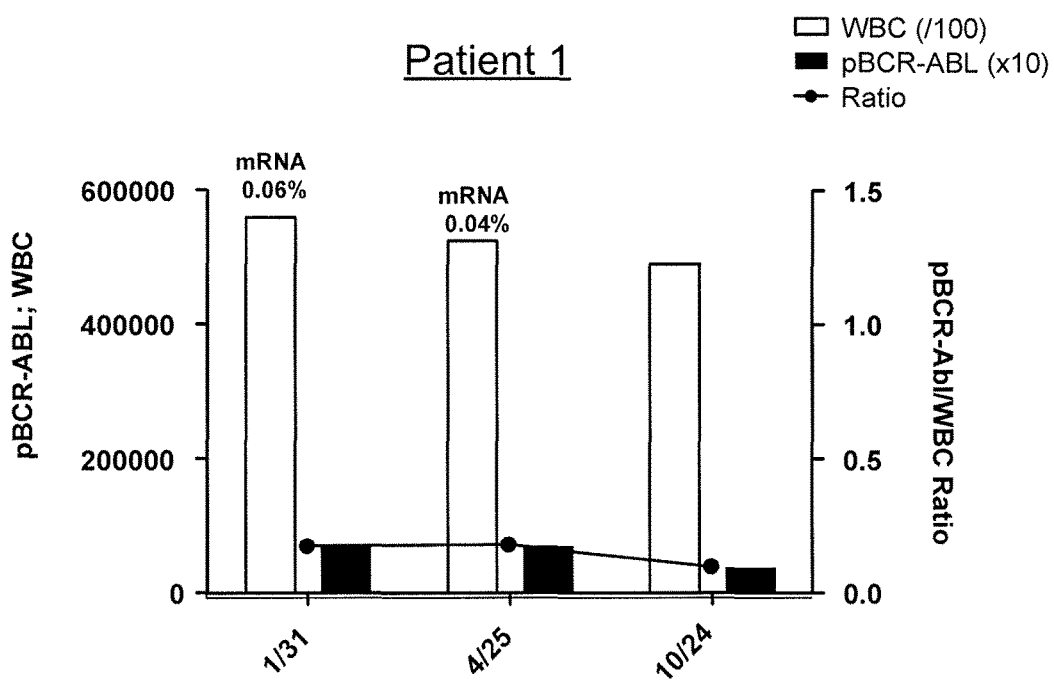
FIG. 27A-B illustrate the activated BCR-ABL levels of Patients 1 (A) and 7 (B) at multiple time points. WBC=white blood cell. pBCR-ABL=phospho-BCR-ABL. tBCR-ABL=total BCR-ABL. % P/T=phospho-BCR-ABL/tBCR-ABL in percentage.

Patient 1 was diagnosed with CML in December 2006 and received imatinib (Gleevec) treatment. To determine Patient 1's response to imatinib, total and activated BCR-ABL levels were analyzed at three time points (1/31, 4/25, and 10/24). Patient 1 had a phosphorylated BCR-ABL/white blood cell ratio of 0.130 at time point 1, a ratio of 0.133 at the time point 2 and a ratio of 0.078 at the third time point 3 (FIG. 27A). The change in phosphorylated BCR-ABL levels across the time points was not detect by mRNA expression assay as mRNA values were 0.04±0.01% and 0.04% at time point 2 and 3, respectively. RNA expression assay detects active tumor cells at three log reduction from a standard baseline value. The advantage of the CEER immuno-microarray is that it detects phospho-BCR-ABL at more than three logs reduction.

Figure 27B:
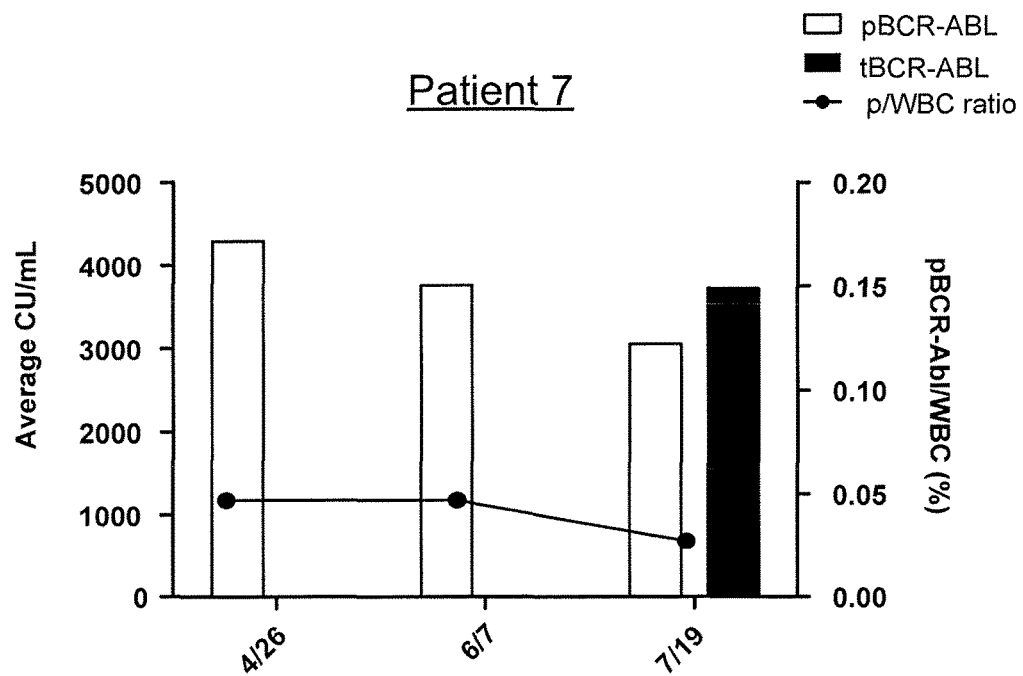

The results from Patient 7 show that mRNA levels of BCR-ABL levels were undetectable, yet total and activated BCR-ABL levels were detected using the CEER Immuno-microassay. The method of the present invention proved to be 10× more sensitive for detecting activated BCR-ABL than total BCR-ABL. In particular, CEER Immunoassay detects the expression and activation state of BCR-ABL in patients with an active tumor cell to total white blood cell ration of 0.05%, which corresponds to a greater than four log reduction from a standard baseline value. Patient 7 was diagnosed with CML in May and initiated imatinib treatment in April. Response to treatment was monitored at two time points post-treatment (e.g., June and February). The results show that phospho-BCR-ABL decreased with time (see, bar graph and line graph of FIG. 27B).

Figure 28A:
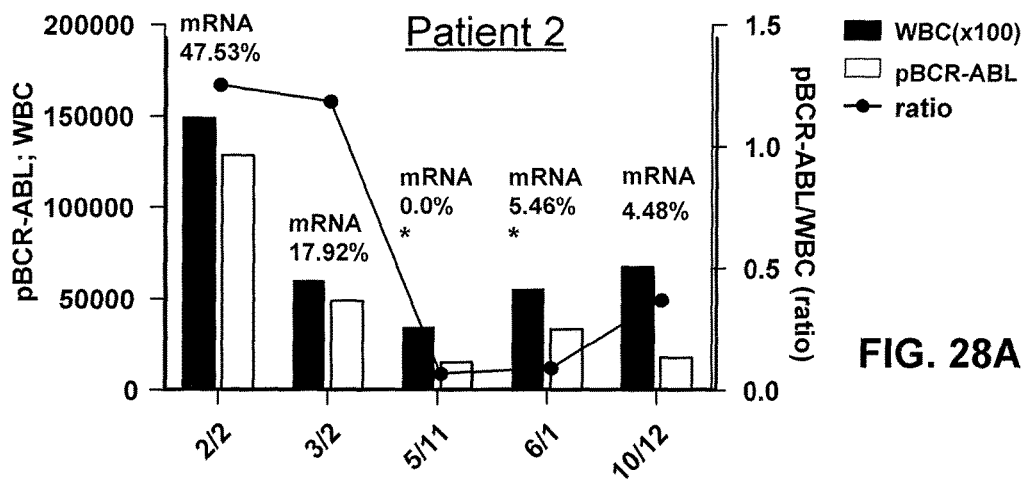
FIG. 28A-C illustrate the BCR-ABL profile of Patient 2 at multiple time points.
Figure 28B:
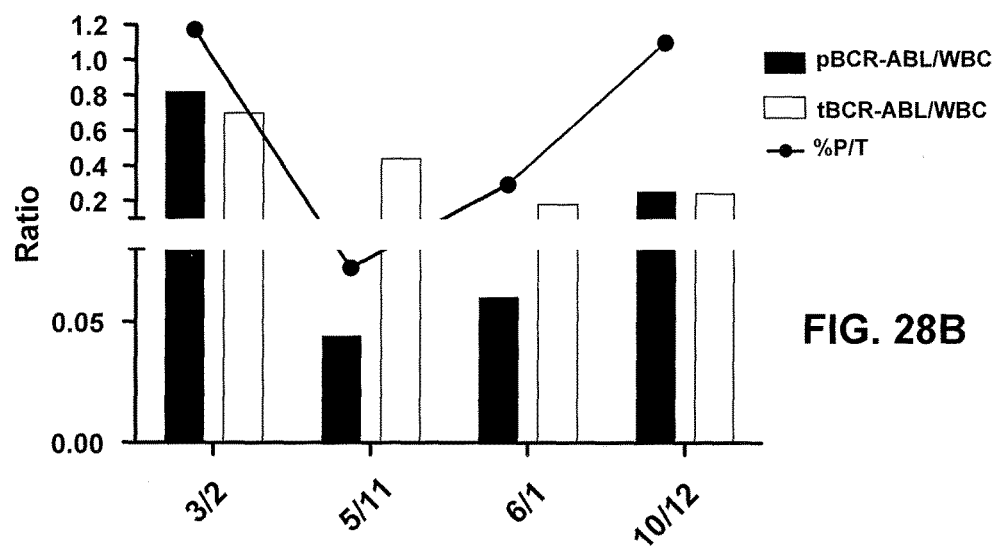
Figure 28C:
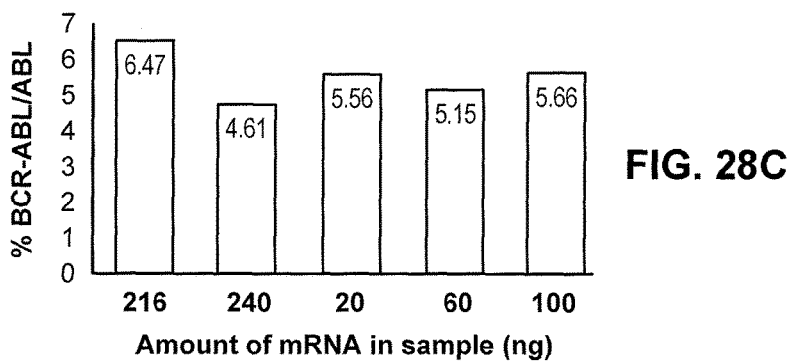

Patient 2 was diagnosed in January and received imatinib treatment in February Leukocytes and CTCs from the patient were isolated and lysed using the 96-well embodiment of the cell isolation apparatus from blood drawn on 2/2 and 3/2. The tube embodiment of the cell isolation apparatus of the present invention was used from blood drawn on 10/12 and 12/21. Using methods of the present invention, it was determined that Patient 2 expressed a lower level of activated BCR-ABL at the time point in May (see, e.g., bar graph and line graph of FIG. 28A, B). Yet, the level increased by October The results from the CEER Immunoassay correlates with the mRNA expression data. The accuracy of Q-PCR using standard methods (e.g., MolecularMD kit for BCR-ABL) and low levels of mRNA are highlighted in FIG. 28C. The % of BCR-ABL to ABL varied with amount of mRNA present in the sample.

Monitoring In Vitro Drug Response in Patient Samples.

To determine Patient 2's response to drug treatment in vitro, a blood sample was treated with various amounts of either imatinib or nilotinib and the total and activated state of BCR-ABL was assayed. The CEER immunoassay was able to detect the response to drug treatment in Patient 7's sample, thus demonstrating that this assay is a useful tool for determining the best therapy for a patient.

Figure 29A:
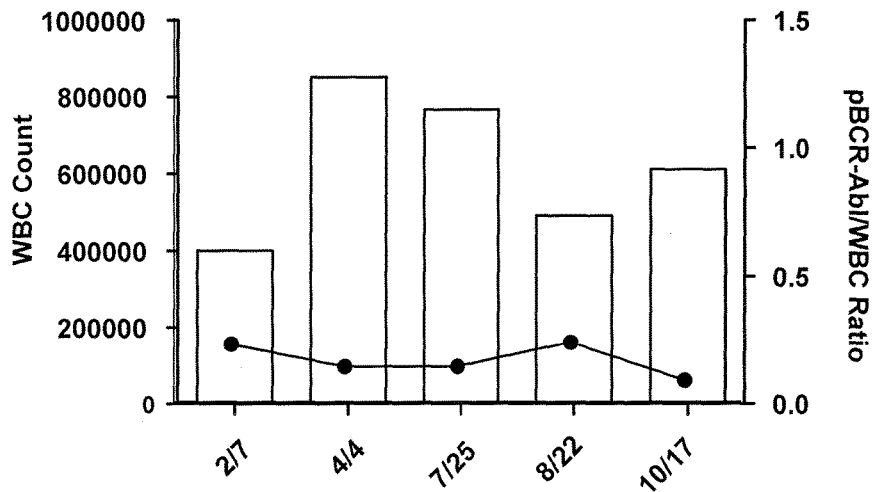
FIG. 29A-B illustrate the WBC count and pBCR-ABL/WBC ratio of Patient 3 at multiple time points (A).
Figure 29B:
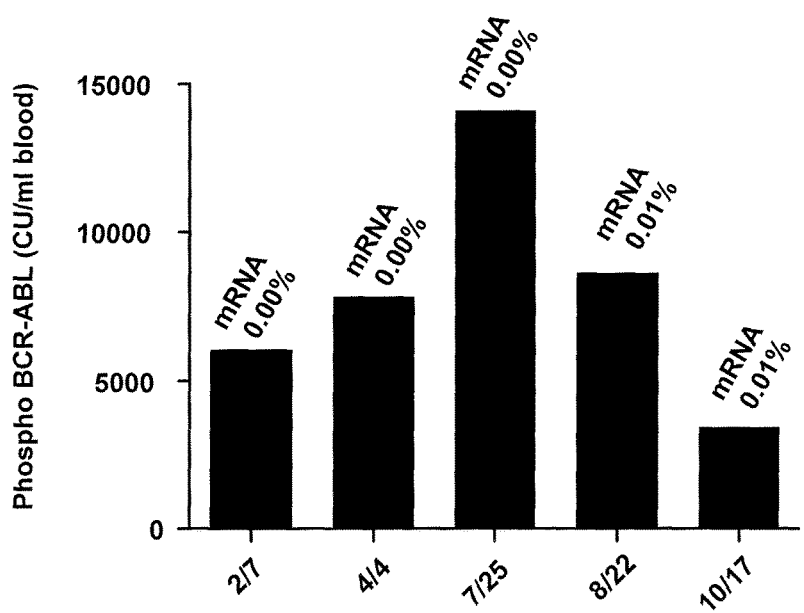

Patient 3 was diagnosed with CML and received dasatinib (Sprycel) treatment. Total and activated BCR-ABL levels were monitored at 5 time points (2/07 4/04/, 7/25, 8/22/and 10/17). The blood drawn on 2/07 and 4/04 were processed using the 96-well embodiment of the cell isolation apparatus and blood drawn in 7/25 and 8/22 were processed using the tube embodiment of the apparatus of the present invention. FIG. 29A shows that the pBCR/WBC ratio was lowest on 10/17. FIG. 29B illustrates that phospho-BCR-ABL level peaked in the sample from 7/25 and decreased to its lowest level in the 10/17 sample. Patient 3 responded to dasatinib and had lower levels of activated BCR-ABL at the last time point, as highlighted in FIG. 29A. The results of the CEER assay for phospho-BCR-ABL correlate with the mRNA expression data.

Figure 30A:
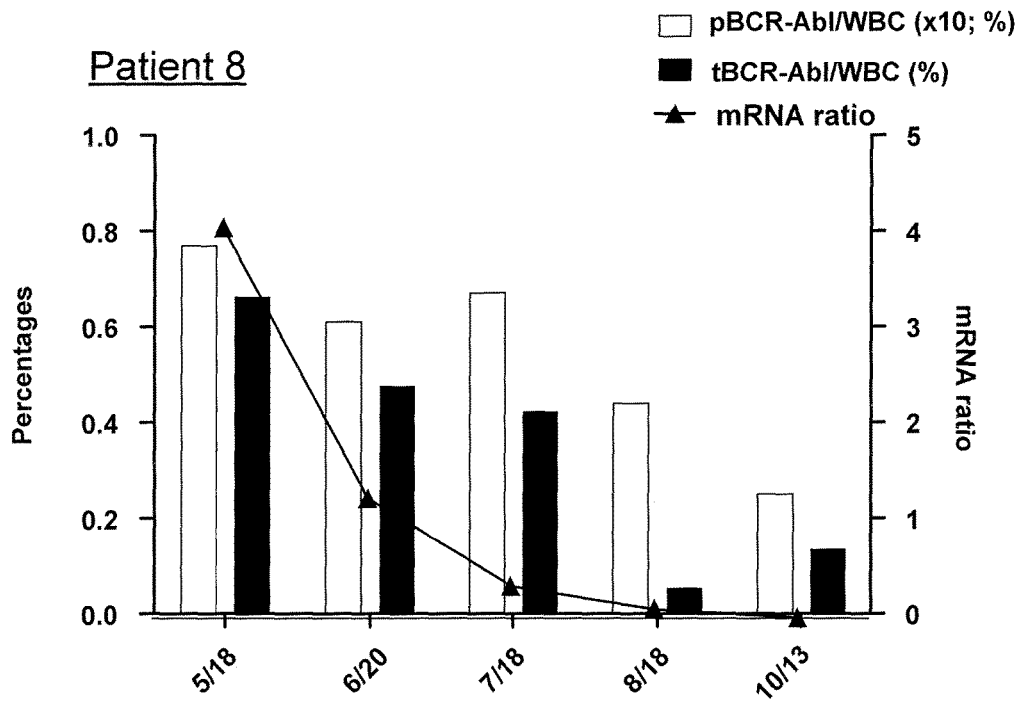
FIG. 30A-B illustrate the total and activated BCR-ABL levels of Patient 8 at multiple time points (A).
Figure 30B:
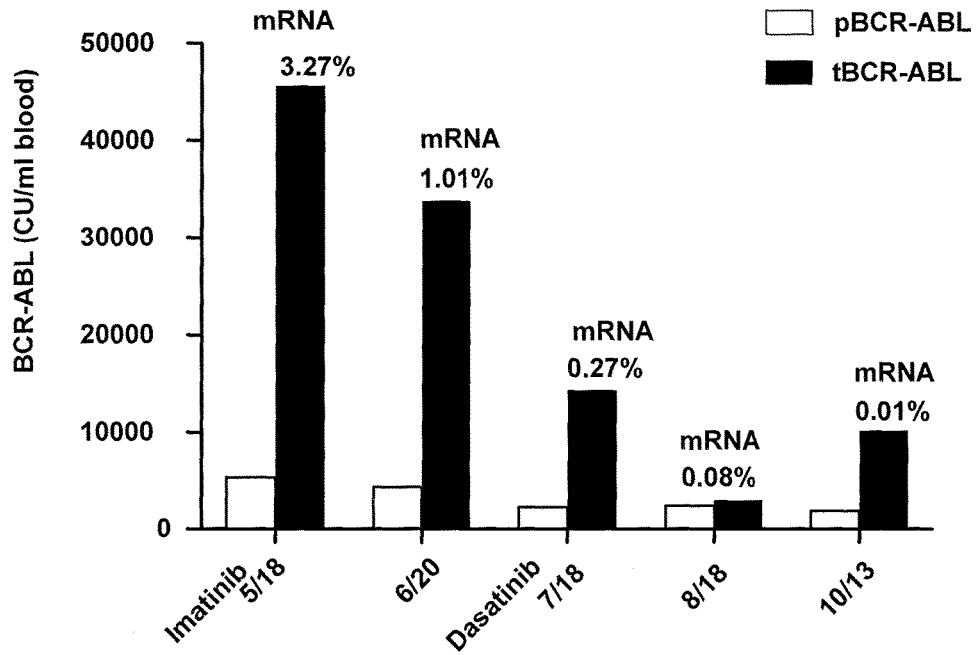

Patient 8 was diagnosed with CML on July 2007 and was changed to dasatinib treatment from imatinib on 05/25. Blood was drawn on 5/18 and 6/20 and processed using the 96-well embodiment of the cell isolation apparatus of the present invention. The tube embodiment of the present invention was used to isolate and lyse leukocytes and CTCs from blood drawn on 7/18, 08/18 and 10/13. FIG. 30A shows that the phospho BCR-ABL/WBC ratio decrease from 5/18 to 8/18, yet increased on 03/13. The phospho BCR-ABL/total BCR-ABL ratio increased while the patient was receiving dasatinib (FIG. 30B), possibly due to progression of CML.

Patient 18 responded to an initial treatment of nilotinib on 08/20, and then to a treatment of ponatinib on 08/22. All blood drawn from the patient in this study was processed using the tube embodiment of the cell isolation apparatus of the present invention. The results from methods of the present invention show that the pBCR-ABL/WBC ratio decreased during the course of therapy. The mRNA ratio as determined by standard methods known to those skilled in the art also shows a decrease in BCR-ABL during the measured time period.

Figure 31A:
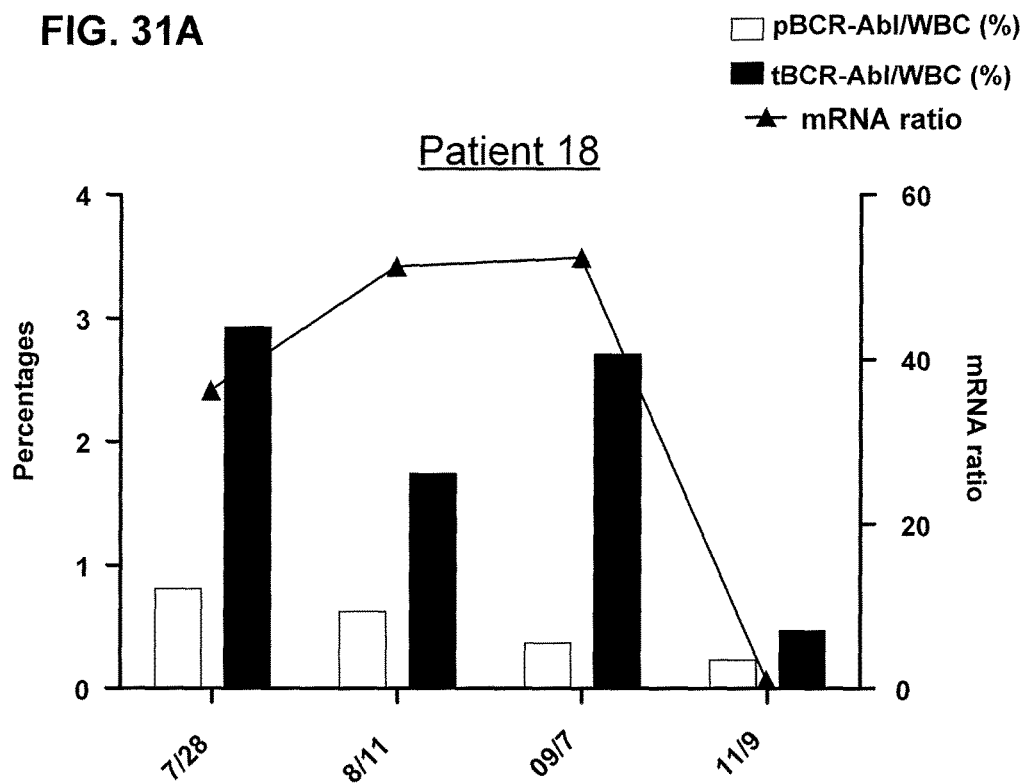
FIG. 31A-B illustrates the total and activated BCR-ABL levels in Patients 14 (B) and 18 (A) at multiple time points.
Figure 31B:
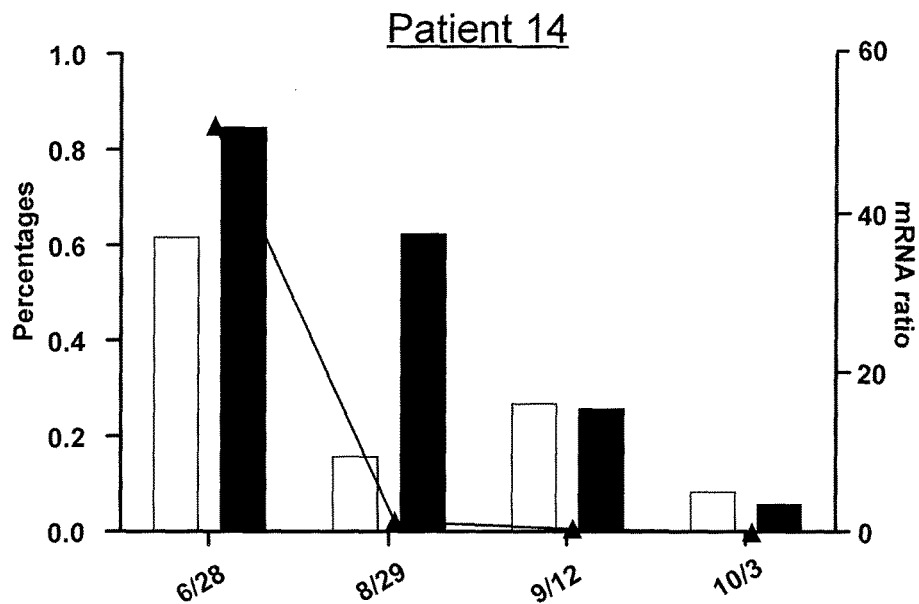
Figure 32A:
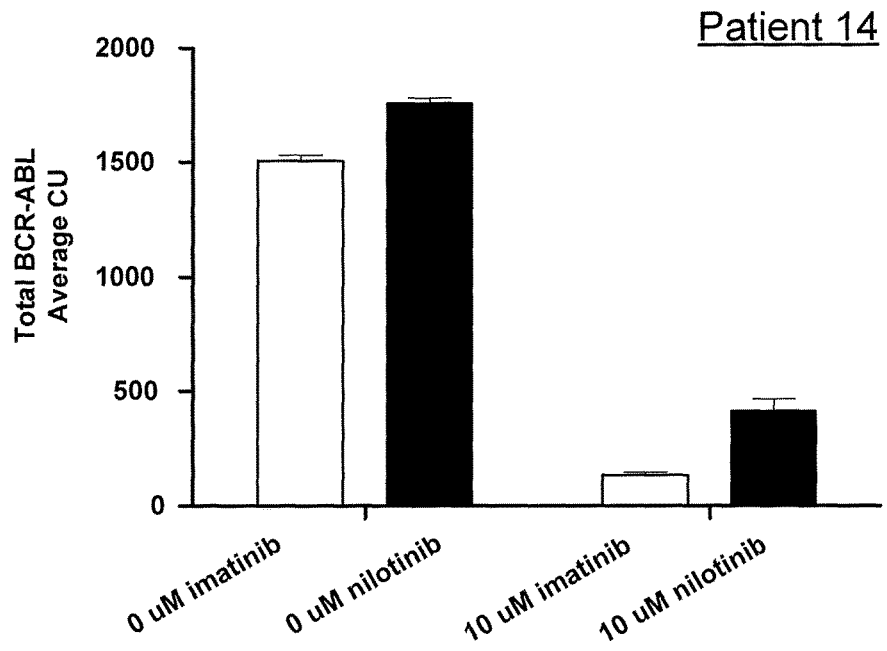
FIG. 32A-B shows Patient 14's response to in vitro treatment of imatinib or nilotinib. Total and phospho-BCR-ABL levels decreased upon drug treatment.
Figure 32B:
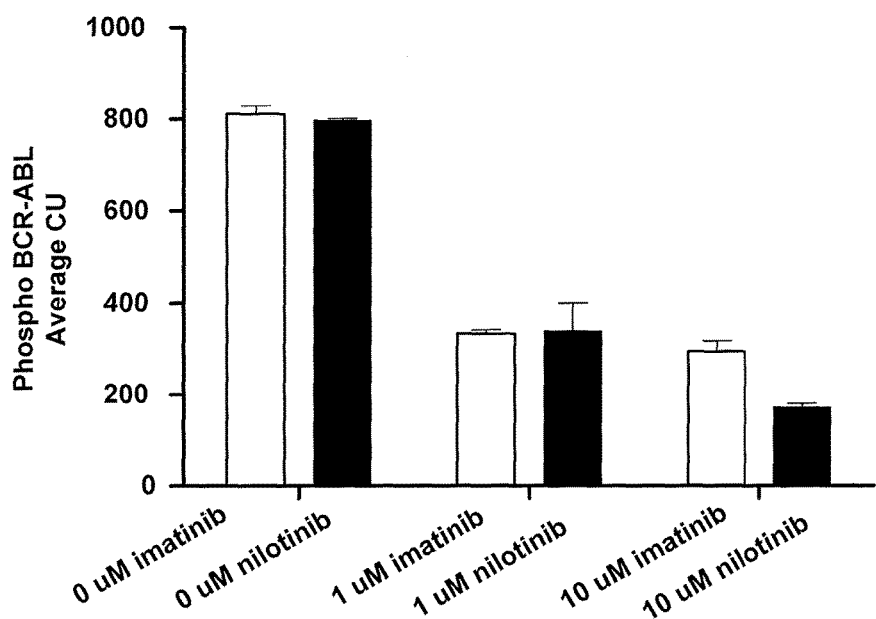

Patient 14 was diagnosed with CML in June and received hydroxyurea treatment on 6/28 and dasatinib in 08/29. Blood drawn on 8/29 and 10/03 was processed using the tube embodiment of the cell isolation apparatus of the present invention. FIG. 31B shows that the activated phospho-BCR-ABL level (pBCR-ABL/WBC ratio) decreased after the first time point (6/28) and was at its lowest at the last time point (October 20). A blood sample from patient 14 was in vitro treated with different concentrations of either imatinib or nilotinib. FIG. 32 A-B show that Patient 14's in vitro response to drug treatment lead to a reduction in phosphorylated BCR-ABL upon imatinib or nilotinib treatment.

CONCLUSION

This example illustrates the analysis of BCR-ABL expression and phosphorylation in cell lysates obtained from 20 CML patients. This example illustrates the use of methods of the present invention, including the cell isolation method and the CEER immunoassay. In particular, while blood cells and circulating tumor cells were isolated from a sample of patient's whole blood without removing or diluting the drug level in the blood. Different levels of BCR-ABL kinase inhibition was observed in patients receiving targeted treatment. This example also shows that the detection of BCR-ABL by the CEER immunoassay has a high level of functional sensitivity and is of clinical use for monitoring CML progression. The methods of the present invention can be used for screening and monitoring the efficacy of the drug which is a great benefit to CML patients receiving targeted therapy. Likewise, the methods can assist a clinician to determine the most effective treatment options for a patient.

All publications and patent applications cited in this specification including PCT Application No. PCT/US2010/053386, filed Oct. 20, 2010, are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An apparatus for isolating and separating leukocytes from red blood cells in a whole blood sample, said apparatus comprising:

a filtration device comprising an upper chamber, which is a cylindrical tube, a lower chamber, which is a cylindrical tube, and one or more stacked filter membranes between said upper and lower chambers, wherein said one or more stacked filter membranes are capable of retaining said leukocytes, wherein the inner diameters of the upper and lower chambers are similar as to create a cylindrical tube which allows liquids to pass therethrough, wherein said one or more stacked filter membranes is placed between screw threads of the upper chamber and lower chamber, which chambers are securely attached together; and a collection tube for collecting red blood cells from said whole blood sample, wherein said filtration device is placed on top of said collection tube, and wherein said red blood cells are separated from said leukocytes and collected in said collection tube following centrifugation.

2. The apparatus of claim 1, wherein said whole blood sample is loaded into said upper chamber of said filtration device.

3. The apparatus of claim 1, wherein said filtration device comprises two, three, or four stacked filter membranes.

4. The apparatus of claim 1, wherein said upper chamber further comprises a snap-cap lid attached thereto.

5. The apparatus of claim 4, wherein the snap-cap lid is tethered via a strap to the upper chamber.

6. The apparatus of claim 1, further comprising a second collection tube.

7. The apparatus of claim 6, wherein said second collection tube contains lysis buffer.

8. The apparatus of claim 1, wherein said whole blood sample is obtained from a subject having or suspected of having a hematological malignancy.

9. The apparatus of claim 8, wherein said hematological malignancy is chronic myelogenous leukemia (CML).

10. The apparatus of claim 8, wherein said subject is either receiving or not receiving therapy with a therapeutic agent.

11. The apparatus of claim 10, wherein said therapeutic agent is an anticancer drug.

12. The apparatus of claim 11, wherein said anticancer drug is selected from the group consisting of a tyrosine kinase inhibitor, chemotherapeutic agent, hormonal therapeutic agent, radiotherapeutic agent, monoclonal antibody, vaccine, and combinations thereof.

13. The apparatus of claim 12, wherein said tyrosine kinase inhibitor is selected from the group consisting of imatinib mesylate nilotinib, dasatinib, bosutinib, gefitinib, sunitinib, erlotinib, lapatinib, canertinib, semaxinib, vatalanib, sorafenib, leflunomide, vandetanib, and combinations thereof.

14. The apparatus of claim 1, wherein said leukocytes are selected from the group consisting of normal leukocytes, malignant leukocytes, diseased leukocytes, and combinations thereof.

15. The apparatus of claim 1, wherein said apparatus is a plurality of filtration devices.

16. The apparatus of claim 1, wherein said upper chamber is a cylindrical tube with male helical ridges or threads.

17. The apparatus of claim 16, wherein the threads of the upper chamber fit securely into female grooves of the lower chamber.

18. The apparatus of claim 1, a filtration device wherein the upper chamber and the lower chamber are screwed together.

19. A method for preparing a lysate of leukocytes from a whole blood sample without substantial dilution of a therapeutic agent, said method comprising:
(a) loading said whole blood sample into an apparatus of claim 1;
(b) centrifuging said apparatus to capture said leukocytes on said one or more stacked filter membranes and to separate said red blood cells into said collection tube; and
(c) lysing said leukocytes captured on said one or more stacked filter membranes with lysis buffer but without a wash step between steps (b) and (c) to thereby prepare a lysate of leukocytes.

20. The method of claim 19, further comprising replacing said collection tube with a second collection tube between steps (b) and (c).

21. The method of claim 20, further comprising centrifuging said apparatus containing said second collection tube after lysing said leukocytes in step (c) and collecting said lysate of leukocytes in said second collection tube.

22. The method of claim 19, wherein said whole blood sample is obtained from a subject receiving a therapeutic agent.

23. The method of claim 22, wherein said a therapeutic agent is an anticancer drug.

24. The method of claim 19, wherein said whole blood sample is incubated in vitro with a therapeutic agent prior to loading into said apparatus.

25. The method of claim 19, wherein the expression and/or activation level of at least one oncogenic fusion protein and/or signal transduction molecule is measured in said lysate of leukocytes.

26. The method of claim 25, wherein the at least one oncogenic fusion protein comprises BCR-ABL.

27. The method of claim 19, wherein said wherein said apparatus is a plurality of filtration devices.

* * * * *